US008440821B2

(12) United States Patent
Wischik et al.

(10) Patent No.: US 8,440,821 B2
(45) Date of Patent: May 14, 2013

(54) METHODS OF SYNTHESIS AND/OR PURIFICATION OF DIAMINOPHENOTHIAZINIUM COMPOUNDS

(75) Inventors: Claude Michel Wischik, Aberdeenshire (GB); John Mervyn David Storey, Aberdeenshire (GB); Colin Marshall, Aberdeenshire (GB); James Peter Sinclair, Aberdeenshire (GB); Thomas Craven Baddeley, Aberdeenshire (GB)

(73) Assignee: Wista Laboratories Ltd., Singapore (SG)

( * ) Notice: Subject to any disclaimer, the term of this patent is extended or adjusted under 35 U.S.C. 154(b) by 0 days.

(21) Appl. No.: 13/149,164

(22) Filed: May 31, 2011

(65) Prior Publication Data

US 2011/0294795 A1    Dec. 1, 2011

Related U.S. Application Data

(62) Division of application No. 12/373,216, filed as application No. PCT/GB2007/002570 on Jul. 10, 2007, now Pat. No. 7,956,183.

(60) Provisional application No. 60/819,627, filed on Jul. 11, 2006.

(51) Int. Cl.
C07D 279/28 (2006.01)

(52) U.S. Cl.
USPC ............ 544/37; 514/225.2; 514/225.8

(58) Field of Classification Search ............ 544/37
See application file for complete search history.

(56) References Cited

U.S. PATENT DOCUMENTS

| | | | |
|---|---|---|---|
| 3,395,018 A | 7/1968 | Read | |
| 7,956,183 B2 * | 6/2011 | Wischik et al. | 544/37 |
| 2003/0158204 A1 | 8/2003 | Galey | |
| 2005/0107607 A1 | 5/2005 | Vig | |

FOREIGN PATENT DOCUMENTS

| | | |
|---|---|---|
| DE | 1886 | 12/1877 |
| DE | 103147 | 6/1898 |
| DE | 113721 | 6/1899 |
| EP | 0510668 | 10/1992 |
| WO | WO 96/30766 | 10/1996 |
| WO | WO 01/62289 | 8/2001 |
| WO | WO 01/96322 | 12/2001 |
| WO | WO 02/055720 | 7/2002 |
| WO | WO 02/075318 | 9/2002 |
| WO | WO 2005/030676 | 4/2005 |
| WO | WO 2005/054217 | 6/2005 |
| WO | WO 2006/032879 | 3/2006 |
| WO | WO 2008/006979 | 1/2008 |

OTHER PUBLICATIONS

The International Preliminary Report on Patentability for PCT/GB2007/002570, dated Jan. 13, 2009. (8 pgs.).
The International Search Report for PCT/GB2007/002570, dated Dec. 19, 2007. (8 pgs.).
Cohn, G., "Ueber das Acetyl-Leukomethylenblau", Arch Pharm, vol. 237, 1899, pp. 385-390.
Gensler, Walter J., et al. "Hydrolysis and Autooxidation fo N-Benzoylleucomethylene Blue" J. Org. Chem, 1966, vol. 31(7), pp. 2324-2330.
Wainwright, Mark, "Methylene blue derivatives—suitable photoantimicrobials for blood product disinfection?" Int. J. Antimicrob. Agents, 2000, vol. 16, pp. 381-394.
Muller-Breitenkreutz, H. Mohr, "Hepatitis C and human immunodeficiency virus RNS degradation by methylene blue/light treatment of human plasma" J. Med. Virology, 1998, vol. 58, pp. 239-245.
Schirmer, H., et al., "Methylene blue as an antimaterial agent", Redox Report, vol. 8, 2003. pp. 272-275.
Tomlin, O.D., et al., "Synthesis and Properties of Phenothiazine Derivatives", Chemistry of Heterocyclic Compounds, 1996, vol. 32, No. 9, pp. 1105-1108.
Rengelshausen, J. et al., "Pharmacokinetic interaction of chloroquine and methylene blue combination against malaria", European Journal of Clinical Pharmacology, vol. 60, 2004, pp. 709-715.
Marshall, P.N., Lewis, S.M., "Metal contamination in commercial dyes," Stain Technology, vol. 50 (3), 1975 b, pp. 143-147.
Marshall, P.N., Lewis, S.M., "The purification of Methylene Blue and Azure B by solvent extraction and crystallisation," Stain Technology, vol. 50(6), 1975 a, pp. 375-381.
Lohr, W., Grubhoffer et al., "The azure dyes: their purification and physiochemical properties. Purification of Azure B," Stain Technology, vol. 50 (3), 1975, pp. 149-156.
Lillie, R.D., et al., "Zinc Chloride Methylene Blue, I. Biological Stain History, Physical Characteristics and Approximation of Azure B Content of Commercial Samples," Stain Technology, vol. 54, 1979, No. 1, pp. 33-39.
Leventis, N., et al., "Synthesis of Substituted Phenothiazine Analogues to Methylene Blue by Electrophilic and Nucleophilic Aromatic Substitutions in Tandem, A Mechanistic Perspective," Tetrahedron, 1997, vol. 53, No. 29, pp. 10083-10092.

(Continued)

Primary Examiner — Kahsay T Habte
(74) Attorney, Agent, or Firm — Foley & Lardner LLP

(57) ABSTRACT

Described is a method for the synthesis and/or purification of a high purity diaminophenothiazinium compound of the following formula:

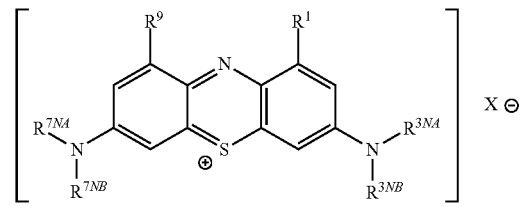

characterized by a purity of greater than 98% and less than 1% Azure B, 0.15% Azure A, 0.15% Azure C and 0.05% Methylene Violet Bernthsen (MVB), as impurities. Also described are related high purity compounds, compositions, and methods of using such compounds and compositions. The compounds and compositions are useful in the treatment of diseases caused by tau aggregation, such as Alzheimer's disease and other dementias, and infection.

30 Claims, 2 Drawing Sheets

OTHER PUBLICATIONS

Guttmann P, Ehrlich P. Über die Wirkung des Methylenblau bei Malaria., *Berl Klin Wochenschr* 1891; vol. 28, pp. 953-956.(plus translation).

Gilman, H., et al., "Some Derivatives of Phenothiazine," *Journal of the American Chemical Society*, 1944, vol. 66, pp. 888-893.

Fierz-David and Blangley, "F. Oxazine and Thiazine Dyes," in: *Fundamental Processes of Dye Chemistry*, published by Interscience (London, UK), 1949, pp. 308-314.

Drew, H.D.K., et al., "Derivatives of Methylene-blue," *Journal of the Chemical Society*, 1933, pp. 248-253.

Colour Index, vol. 4 (3rd Edition, 1971), p. 4470, Entry No. 52015.

Cohn, G., "Zur Kenntniss des Leukomethyleneblaus," *Chemische Berichte*, vol. 33, 1900, pp. 1567-1568.(plus translation).

Cohn, G., "Verfahren zur Darstellung von Acetylleukomethylenblau und -athyleneblau," *Chem. Zentralblatt*, vol. 70, II, 1899, p. 503. (plus translation).

Bernthsen, "Studien in der Methylenblaugruppe," *Justus Liebig's Annalen der Chemie, Band*, vol. 251, 1899, pp. 1-96. (plus partial translation).

Bernthsen, "Studien in der Methylenblaugruppe," *Justus Liebig's Annalen der Chemie, Band*, vol. 230, 1885b, pp. 137-211. (plus partial translation).

Bernthsen, "Studien in der Methylenblaugruppe," *Justus Liebig's Annalen der Chemie, Band*, vol. 230, 1885a, pp. 73-136. (plus partial translation).

* cited by examiner

METHODS OF SYNTHESIS AND/OR PURIFICATION OF DIAMINOPHENOTHIAZINIUM COMPOUNDS

CROSS REFERENCE TO RELATED APPLICATIONS

This application is a divisional of U.S. application Ser, No. 12/373,216; which is the U.S. National Phase of International Application No. PCT/GB2007/002570, filed Jul. 10, 2007, which was published in English on Jan. 17, 2008, as WO2008/007074; and which claims the benefit of United States provisional patent application No. 60/819,627, filed 11 Jul. 2006; the contents of which are incorporated herein by reference in their entirety.

RELATED APPLICATION

This application is related to U.S. provisional patent application No. 60/819,627 filed 11 Jul. 2006, the contents of which are incorporated herein by reference in their entirety.

TECHNICAL FIELD

This invention pertains generally to the field of chemical synthesis and purification, and more specifically to methods of synthesis and/or purification of certain 3,7-diamino-phenothiazin-5-ium compounds (referred to herein as "diaminophenothiazinium compounds") including Methylthioninium Chloride (MTC) (also known as Methylene Blue). The present invention also pertains to the resulting (high purity) compounds, compositions comprising them (e.g., tablets, capsules), and their use in methods of inactivating pathogens, and methods of medical treatment, prophylaxis, and diagnosis, etc., for example, a tauopathy; a disease of tau protein aggregation; Alzheimer's disease (AD); Pick's disease; Progressive Supranuclear Palsy (PSP); fronto-temporal dementia (FTD); FTD and parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD); mild cognitive impairment (MCI); skin cancer; melanoma; methemoglobinemia; a viral infection; a bacterial infection; a protozoal infection; a parasitic infection; malaria; visceral leishmaniasis; African sleeping sickness; toxoplasmosis; giardiasis; Chagas' disease; Hepatitis C virus (HCV) infection; human immunodeficiency virus (HIV) infection; West Nile virus (WNV) infection; a synucleinopathy; Parkinson's disease (PD); dementia with Lewy bodies (DLB); multiple system atrophy (MSA); drug-induced parkinsonism; and pure autonomic failure (PAF).

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Methylthioninium Chloride (MTC) (Also Known as Methylene Blue)

Methylthioninium Chloride (MTC) (also known as Methylene blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

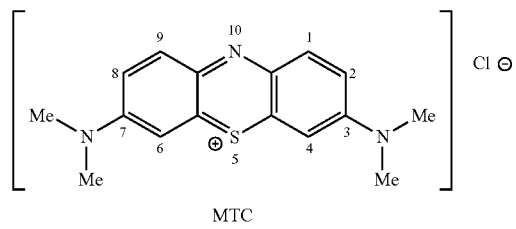

MTC

Methylthioninium Chloride (MTC) (also known as Methylene Blue), perhaps the most well known phenothiazine dye and redox indicator, has also been used as an optical probe of biophysical systems, as an intercalator in nanoporous materials, as a redox mediator, and in photoelectrochromic imaging.

See, for example, Colour Index (Vol. 4, 3rd edition, 1971) and Lillie et al., 1979, and references cited therein.

MTC may conveniently be considered to be an "oxidized form" when considered in respect of the corresponding 10H-phenothiazine compound, N,N,N',N'-tetramethyl-10H-phenothiazine-3,7-diamine, which may conveniently be considered to be a "reduced form" (also known as the "leuco" form).

Scheme 1

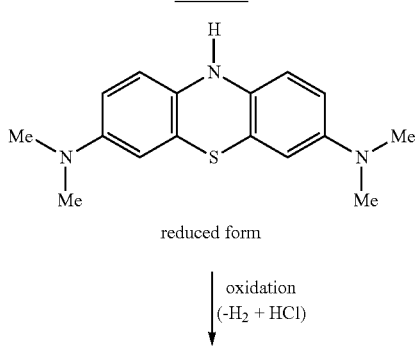

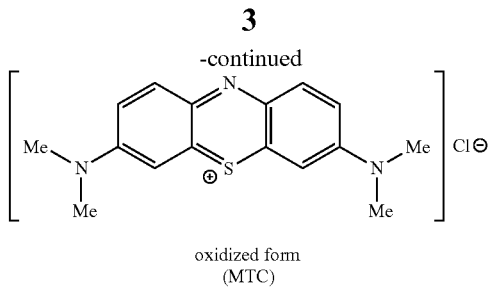

oxidized form
(MTC)

Synthesis and Purification

MTC was first described in a German Patent in 1877 (Badische Anilin- and Soda-Fabrik, 1877). In that patent, MTC was synthesized by nitrosylation of dimethylaniline, subsequent reduction to form N,N-dimethyl-1,4-diaminobenzene, and subsequent oxidative coupling in the presence of hydrogen sulphide ($H_2S$) and iron(III) chloride ($FeCl_3$).

Bernthsen described subsequent studies of MTC and methods for its synthesis (see Bernthsen, 1885a, 1885b, 1889).

Fierz-David and Blangley, 1949, also describes methods for the synthesis of MTC from dimethylaniline, as illustrated in the following scheme

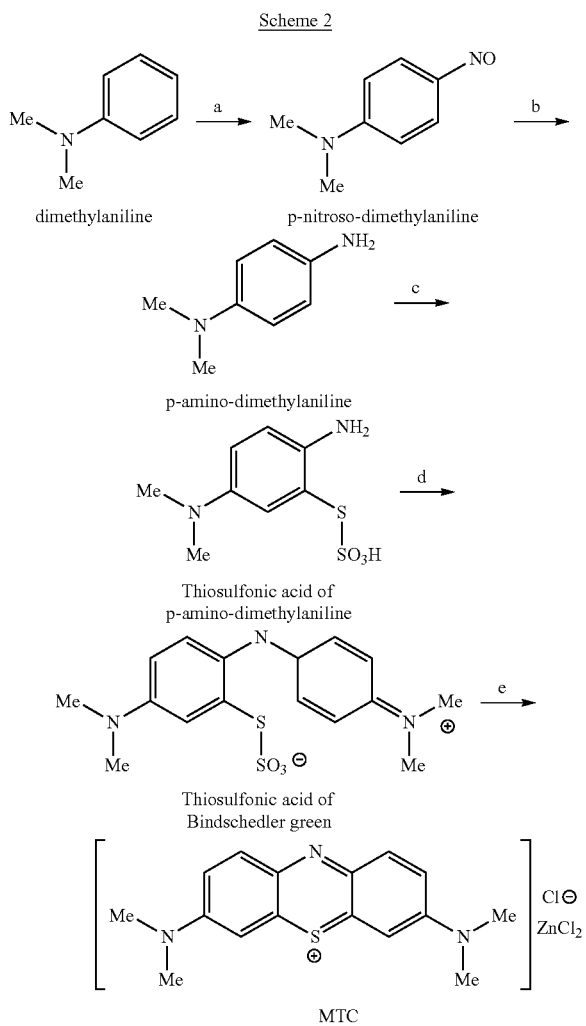

Scheme 2

In step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline in aqueous acid (HCl) solution using zinc dust solution. In steps (c), (d), and (e), the p-aminodimethylaniline is oxidized in aqueous acid solution with another molecule of dimethylaniline, and simultaneously a thiosulfonic acid group is introduced; the ring is then closed using manganese dioxide or copper sulfate. More specifically, a clear neutral solution of p-aminodimethylaniline is acidified ($H_2SO_4$), and a non-reducing zinc chloride solution is added ($ZnCl_2$ with $Na_2Cr_2O_7$). Aluminium thiosulfate ($Al_2(S_2O_3)_3$) and sodium thiosulfate ($Na_2S_2O_3$) are added. Sodium dichromate ($Na_2Cr_2O_7$) is added. The mixture is heated and aerated. Dimethylaniline is added. Sodium dichromate ($Na_2Cr_2O_7$) is added. The mixture is heated, and becomes dark greenish-blue in colour due to the formation of the thiosulfonic acid of Bindschedler green. Manganese dioxide or copper sulfate is added, and the mixture heated, and the dye precipitates from the concentrated zinc chloride solution.

Very similar synthesis methods are described in the Colour Index (Vol. 4, 3rd edition, 1971), p. 4470.

Masuya et al., 1992, describe certain phenothiazine derivatives, and methods for their preparation and use in photodynamic therapy of cancer and in immunoassays utilizing chemiluminescence. The compounds are prepared by routes similar to those discussed above.

Leventis et al., 1997, describe methods for the synthesis of certain methylthioninium bromide (MTB) analogs, which employ phenothiazine as a starting material and which add the desired 3,7-substituents by halogenation followed by amination. The authors assert that MTC is synthesized commercially by oxidation of N,N-dimethyl-p-phenylene diamine with $Na_2Cr_2O_7$ in the presence of $Na_2S_2O_3$, followed by further oxidation in the presence of N,N-dimethylaniline.

Marshall and Lewis, 1975a, describes the purification of commercial MTC and Azure B by solvent extraction and crystallisation. They assert that aqueous MTC/Azure B mixtures at a buffered pH of 9.5 can be separated by extraction with carbon tetrachloride. The carbon tetrachloride removes the Azure B while leaving the MTC in the aqueous layer. They further assert that low temperature crystallisation of MTC at a concentration of 0.25 N with hydrochloric acid removes metal contaminants. However, the organic purity analysis reported therein is based on thin-layer chromatography, which is not suitable for quantification. Also, the microanalysis for sulphated ash does not indicate a metal free sample. (The preferred technique in 1975 was atomic absorption.)

Marshall and Lewis, 1975b, describes the analysis of metal contaminants in commercial thiazine dyes by atomic absorption spectrophotometry. They report 38 samples with metal concentrations that vary widely between 0.02% and 25.35% of individual samples; the metals examined were iron, potassium, sodium and zinc. They also report that other metals may be present which were not analysed. Aluminium, chromium, manganese, and copper, are all involved in synthetic procedures for MTC and are almost certain to be present. Importantly, they report large variations in the metal content of commercial samples of MTC.

Lohr et al., 1975, describes the purification of Azure B by column chromatography, specifically by separation to isolate the desired product followed by ion exchange back to the chloride. They assert that other cationic dyes such as MTC can be purified by this method. However, column chromatography is not a suitable method for the purification of MTC on a large scale.

Fierz-David et al., 1949, describes the synthesis of the zinc chloride double salt of MTC and the removal of zinc by chelating with sodium carbonate followed by filtration to generate zinc free methylene blue. However, the authors acknowledge that this technique cannot be used on a large scale, because the yields are poor.

Cohn, 1899, describes methods for the synthesis of acetyl leuco-methylene blue and ethylene blue, apparently using acetic anhydride and zinc powder.

Storey et al., 2006, describe recent methods for the synthesis and purification of diaminophenothiazinium compounds such as MTC.

Uses

MTC is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria either singly (Guttmann & Ehrlich, 1891) or in combination with chloroquine (Schirmer et al. 2003; Rengelhausen et al. 2004). Malaria in humans is caused by one of four protozoan species of the genus *Plasmodium: P. falciparum, P. vivax, P. ovale,* or *P. malariae*. All species are transmitted by the bite of an infected female *Anopheles* mosquito. Occasionally, transmission occurs by blood transfusion, organ transplantation, needle-sharing, or congenitally from mother to fetus. Malaria causes 300-500 million infections worldwide and approximately 1 million deaths annually. Drug resistance, however is a major concern and is greatest for *P. falciparum*, the species that accounts for almost all malaria-related deaths. Drugs or drug combinations that are currently recommended for prophylaxis of malaria include chloroquine/proguanil hydrochloride, mefloquine, doxycycline and primaquine.

MTC (under the name Virostat® and subsequently Suvus®, from Bioenvision Inc., New York) has shown potent viricidal activity in vitro. Specifically MTC is effective against viruses such as Hepatitis C, HIV and West Nile Virus in laboratory tests. West Nile virus (WNV) is a potentially serious illness affecting the central nervous system. The large majority of infected people will show no visible symptoms or mild flu-like symptoms such as fever and headache. About one in 150 will develop severe symptoms including tremors, convulsions, muscle weakness, vision loss, numbness, paralysis or coma. Generally, WNV is spread by the bite of an infected mosquito, but can also spread through blood transfusions, organ transplants, breastfeeding or during pregnancy from mother to child.

Suvus® is also currently in clinical trials for the treatment of chronic Hepatitis C. Hepatitis C is a viral infection of the liver. The virus, HCV, is a major cause of acute hepatitis and chronic liver disease, including cirrhosis and liver cancer. HCV is spread primarily by direct contact with human blood. The major causes of HCV infection worldwide are use of unscreened blood transfusions, and re-use of needles and syringes that have not been adequately sterilized. The World Health Organization has declared hepatitis C to be a global health problem, with approximately 3% of the world's population infected with HCV and it varies considerably by region. The prevalence in the US is estimated at 1.3% or approximately 3.5 million people. Egypt has a population of approximately 62 million and contains the highest prevalence of hepatitis C in the world, estimated at over 20% of the nation's approximately 62 million people.

MTC, when combined with light, can prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compounds then bind to the nucleic acid of the viral or bacterial pathogen, preventing replication of the DNA or RNA. Because MTC designed to inactivate pathogens, it has the potential to reduce the risk of transmission of pathogens that would remain undetected by testing.

MTC and derivatives thereof (e.g., "diaminophenothiazinium compounds") have been found to be useful in the treatment of tauopathies (such as, for example, Alzheimer's disease) (see, for example, Wischik, C. M., et al., 1996, 2002a).

Oral and parenteral formulations of MTC are commercially available in the United States, usually under the name Urolene Blue®. However, these formulations contain substantial amounts of metal impurities. These impurities are highly undesirable, and many (e.g., including Al, Cr, Fe, Cu) exceed the safety limits set by European health agencies.

Consequently, there is a great need for higher purity (e.g., pharmaceutical grade purity, e.g., a purity safe for human consumption, e.g., with low or reduced organic and/or metal impurity content) diaminophenothiazinium compounds, including MTC.

The inventors have developed methods for the synthesis of diaminophenothiazinium compounds (including MTC), that yield products with extremely high purity and in particular, products with extremely low levels of undesired impurities (both organic and metal impurities) that meet (and often exceed) the safety limits set by European health agencies (e.g., the European Pharmacopoeia).

Without exaggeration, MTC prepared by the methods described herein is the purest available worldwide.

SUMMARY OF THE INVENTION

One aspect of the present invention pertains to a method of synthesis and/or purification of a diaminophenothiazinium compound (DAPTC), including, for example, methylthioninium chloride (MTC), as described herein.

Another aspect of the invention pertains to use of a method of synthesis and/or purification of a diaminophenothiazinium compound as described herein, as part of a method of manufacturing a medicament, for example, a medicament for use in the treatment or prophylaxis of a disease condition (e.g., a disease condition as described herein).

Another aspect of the invention pertains to a diaminophenothiazinium compound, as defined herein and including, for example, methylthioninium chloride (MTC), that is obtained by, or is obtainable by, a method of synthesis and/or purification as described herein and/or that has a purity as defined herein.

Another aspect of the invention pertains to a composition (e.g., a pharmaceutical composition, e.g., a tablet, a capsule) comprising a diaminophenothiazinium compound, as defined herein and including, for example, methylthioninium chloride (MTC), that is obtained by, or is obtainable by, a method of synthesis and/or purification as described herein, and/or that has a purity as defined herein.

Another aspect of the present invention pertains to a diaminophenothiazinium compound, as defined herein and including, for example, methylthioninium chloride (MTC), that is obtained by, or is obtainable by, a method of synthesis and/or purification as described herein, and/or that has a purity as defined herein, for use in a method of treatment (e.g., a method of treatment or prophylaxis, e.g., a method of treatment or prophylaxis of a disease condition, as described herein) of the human or animal body by therapy.

Another aspect of the present invention pertains to the use of a diaminophenothiazinium compound, as defined herein and including, for example, methylthioninium chloride (MTC), that is obtained by, or is obtainable by, a method of synthesis and/or purification as described herein, and/or that has a purity as defined herein, in the manufacture of a medicament for use in the treatment or prophylaxis of a disease condition (e.g., a disease condition as described herein).

Another aspect of the present invention pertains to a method of treatment or prophylaxis of a disease condition (e.g., a disease condition as described herein) in a patient, comprising administering to said patient a therapeutically-effective amount or a prophylactically-effective amount of a diaminophenothiazinium compound, as defined herein and including, for example, methylthioninium chloride (MTC), that is obtained by, or is obtainable by, a method of synthesis and/or purification as described herein, and/or that has a purity as defined herein.

In one embodiment, the disease condition is: a tauopathy; a disease of tau protein aggregation; Alzheimer's disease (AD); Pick's disease; Progressive Supranuclear Palsy (PSP); fronto-temporal dementia (FTD); FTD and parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD); mild cognitive impairment (MCI); skin cancer; melanoma; methemoglobinemia; a viral infection; a bacterial infection; a protozoal infection; a parasitic infection; malaria; visceral leishmaniasis; African sleeping sickness; toxoplasmosis; giardiasis; Chagas' disease; Hepatitis C virus (HCV) infection; human immunodeficiency virus (HIV) infection; West Nile virus (WNV) infection; a synucleinopathy; Parkinson's disease (PD); dementia with Lewy bodies (DLB); multiple system atrophy (MSA); drug-induced parkinsonism; or pure autonomic failure (PAF).

Another aspect of the invention pertains to a diaminophenothiazinium compound, as defined herein and including, for example, methylthioninium chloride (MTC), that is obtained by, or is obtainable by, a method of synthesis and/or purification as described herein, and/or that has a purity as defined herein, for use in a method of inactivating pathogens.

Another aspect of the present invention pertains to a method of inactivating pathogens that employs an effective amount of a diaminophenothiazinium compound, as defined herein and including, for example, methylthioninium chloride (MTC), that is obtained by, or is obtainable by, a method of synthesis and/or purification as described herein, and/or that has a purity as defined herein.

As will be appreciated by one of skill in the art, features and preferred embodiments of one aspect of the invention will also pertain to other aspects of the invention.

DETAILED DESCRIPTION

The Target Compounds

Figure 1:
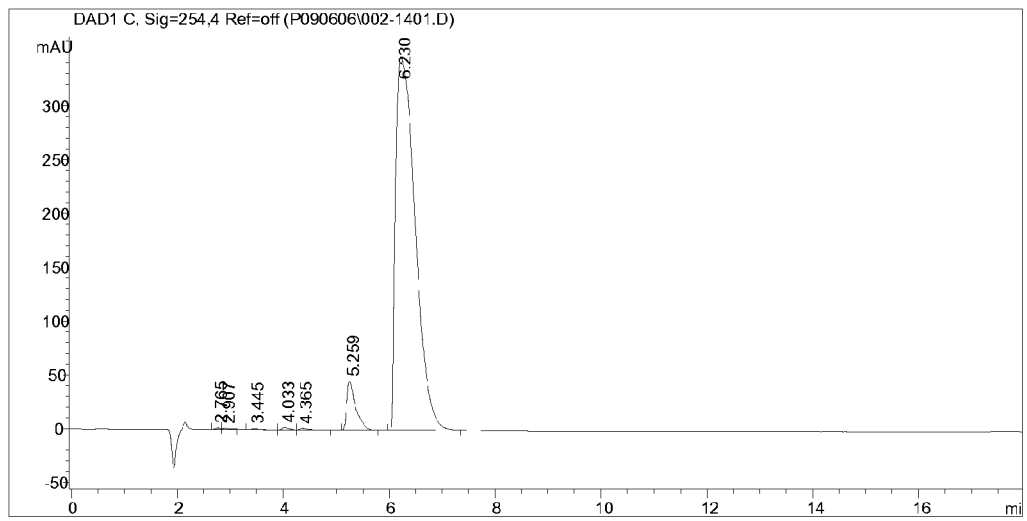
FIG. 1 is an HPLC chromatogram for the Medex™ starting material used in Synthesis 1. Peaks at the following retention times were observed: 2.765, 2.907, 3.445, 4.033, 4.365, 5.259, and 6.230 minutes.

In general, the present invention pertains to methods for the synthesis and/or purification of certain 3,7-diamino-phenothiazin-5-ium compounds of the following formula, collectively referred to herein as "diaminophenothiazinium compounds" (DAPTC):

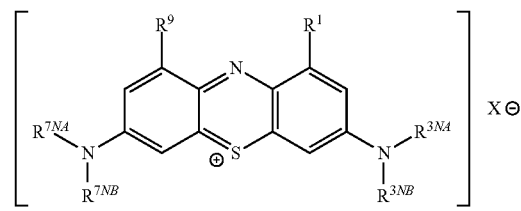

wherein:
each of $R^1$ and $R^9$ is independently selected from: —H; $C_{1-4}$alkyl; $C_{2-4}$alkenyl; and halogenated $C_{1-4}$alkyl;
each of $R^{3NA}$ and $R^{3NB}$ is independently selected from: $C_{1-4}$alkyl; $C_{2-4}$alkenyl; and halogenated $C_{1-4}$alkyl;
each of $R^{7NA}$ and $R^{7NB}$ is independently selected from: $C_{1-4}$alkyl; $C_{2-4}$alkenyl; and halogenated $C_{1-4}$alkyl; and
X is one or more anionic counter ions to achieve electrical neutrality.

The above structure is only one of many equivalent resonance structures, some of which are shown below, and all of which are intended to be encompassed by the above structure:

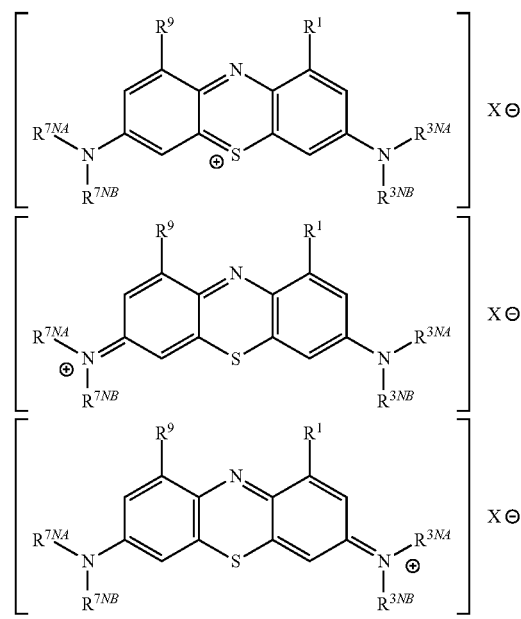

In one embodiment, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{1-4}$alkenyl groups, such as —CH=CH$_2$ (vinyl) and —CH$_2$—CH=CH$_2$ (allyl).

In one embodiment, the halogenated $C_{1-4}$alkyl groups are selected from: —CF$_3$, —CH$_2$CF$_3$, and —CF$_2$CF$_3$.

In one embodiment, each of $R^1$ and $R^9$ is independently —H, -Me, -Et, or —CF$_3$.

In one embodiment, each of $R^1$ and $R^9$ is independently —H, -Me, or -Et.

In one embodiment, each of $R^1$ and $R^9$ is independently —H.

In one embodiment, each of $R^1$ and $R^9$ is independently -Me.

In one embodiment, each of $R^1$ and $R^9$ is independently -Et.

In one embodiment, $R^1$ and $R^9$ are the same.

In one embodiment, $R^1$ and $R^9$ are different.

In one embodiment, each of $R^{3NA}$ and $R^{3NB}$ independently -Et, -nPr, -nBu, —CH$_2$—CH=CH$_2$, or —CF$_3$.

In one embodiment, each of $R^{3NA}$ and $R^{3NB}$ is independently -Me or -Et.

In one embodiment, each of $R^{3NA}$ and $R^{3NB}$ is independently -Me.

In one embodiment, each of $R^{3NA}$ and $R^{3NB}$ is independently -Et.

In one embodiment, $R^{3NA}$ and $R^{3NB}$ are the same.

In one embodiment, $R^{3NA}$ and $R^{3NB}$ are different.

In one embodiment, each of $R^{7NA}$ and $R^{7NB}$ independently -Me, -Et, -nPr, -nBu, —CH$_2$—CH=CH$_2$, or —CF$_3$.

In one embodiment, each of $R^{7NA}$ and $R^{7NB}$ is independently -Me or -Et.

In one embodiment, each of $R^{7NA}$ and $R^{7NB}$ is independently -Me.

In one embodiment, each of $R^{7NA}$ and $R^{7NB}$ is independently -Et.

In one embodiment, $R^{7NA}$ and $R^{7NB}$ are the same.

In one embodiment, $R^{7NA}$ and $R^{7NB}$ are different.

In one embodiment, $R^{3NA}$ and $R^{3NB}$ and $R^{7NA}$ and $R^{7NB}$ are the same.

In one embodiment, the groups —N($R^{3NA}$)($R^{3NB}$) and —N($R^{7NA}$)($R^{7NB}$) are the same.

In one embodiment, the groups —N($R^{3NA}$)($R^{3NB}$) and —N($R^{7NA}$)($R^{7NB}$) are independently selected from: —NMe$_2$, —NEt$_2$, —N(nPr)$_2$, —N(Bu)$_2$, —NMeEt, —NMe(nPr), and —N(CH$_2$CH=CH$_2$)$_2$.

In one embodiment, the groups —N($R^{3NA}$)($R^{3NB}$) and —N($R^{7NA}$)($R^{7NB}$) are independently selected from: —NMe$_2$ and —NEt$_2$.

In one embodiment, each of the groups —N($R^{3NA}$)($R^{3NB}$) and —N($R^{7NA}$)($R^{7NB}$) is independently —NMe$_2$.

In one embodiment, the groups —N($R^{3NA}$)($R^{3NB}$) and —N($R^{7NA}$)($R^{7NB}$) are as defined herein, with the proviso that neither group is —NMe$_2$.

In one embodiment, one or more of the carbon atoms is $^{11}$C or $^{13}$C.

In one embodiment, one or more of the carbon atoms is $^{11}$C.

In one embodiment, one or more of the carbon atoms is $^{13}$C.

In one embodiment, one or more of the nitrogen atoms is $^{15}$N.

In one embodiment, one or more or all of the carbon atoms of one or more or all of the groups $R^{3NA}$, $R^{3NB}$, $R^{7NA}$ and $R^{7NB}$ is $^{13}$C.

In one embodiment, each of the groups —N($R^{3NA}$)($R^{3NB}$) and —N($R^{7NA}$)($R^{7NB}$) is —N($^{13}$CH$_3$)$_2$.

In one embodiment, each of $R^1$ and $R^9$ is —H, and each of the groups —N($R^{3NA}$)($R^{3NB}$) and —N($R^{7NA}$)($R^{7NB}$) is —N($^{13}$CH$_3$)$_2$.

In one embodiment, each of $R^1$ and $R^9$ is —H; each of the groups —N($R^{3NA}$)($R^{3NB}$) and —N($R^{7NA}$)($R^{7NB}$) is —N($^{13}$CH$_3$)$_2$; and X$^-$ is Cl$^-$.

In one embodiment, X$^-$ is independently a halogen anion (i.e., halide) or nitrate anion.

In one embodiment, X$^-$ is independently a halogen anion (i.e., halide).

In one embodiment, X$^-$ is independently Cl$^-$, Br$^-$, or F, or NO$_3^-$.

In one embodiment, X$^-$ is independently Cl$^-$, Br, or F.

In one embodiment, X$^-$ is independently Cl$^-$.

In one embodiment, the compound is in the form of a mixed salt.

Examples of diaminophenothiazinium compounds (DAPTC) include the following:

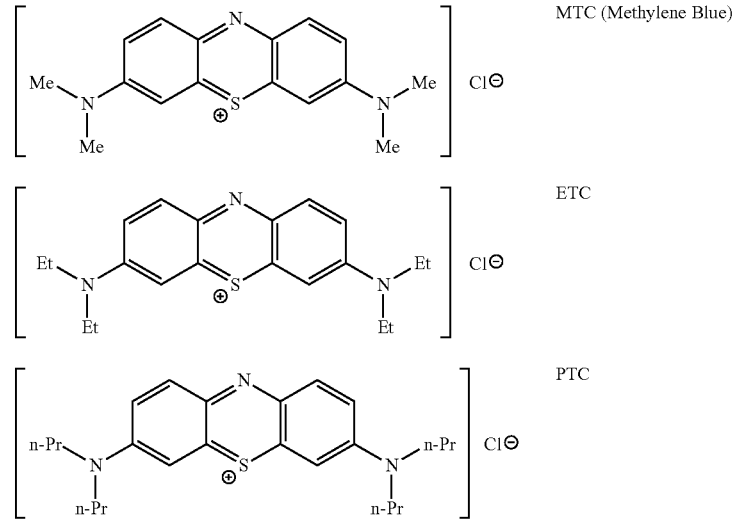

-continued
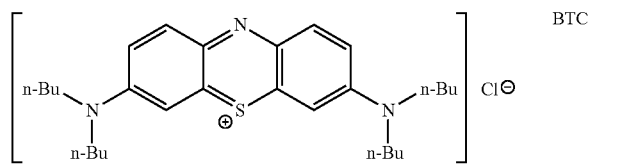 BTC
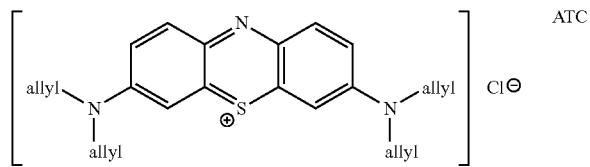 ATC
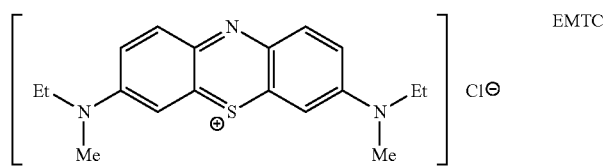 EMTC
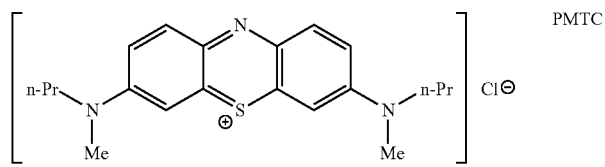 PMTC
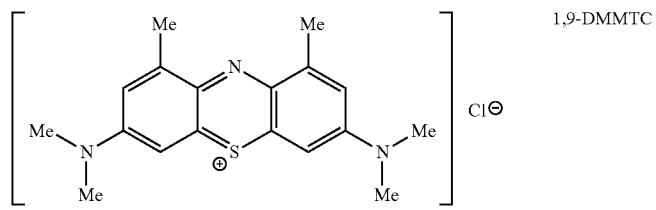 1,9-DMMTC
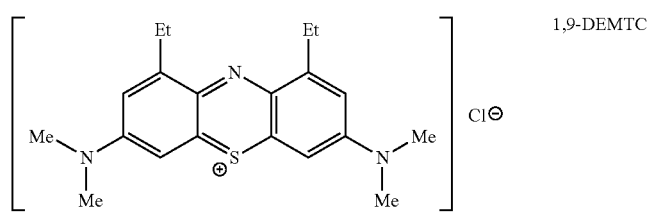 1,9-DEMTC
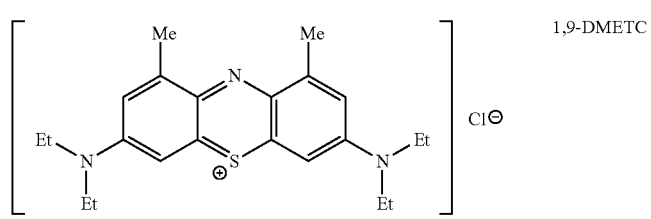 1,9-DMETC
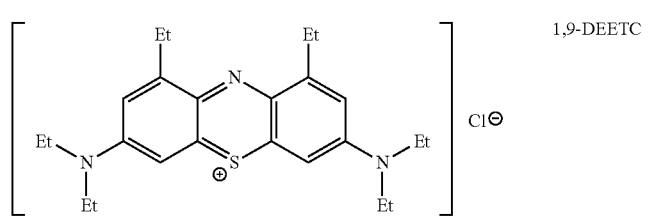 1,9-DEETC

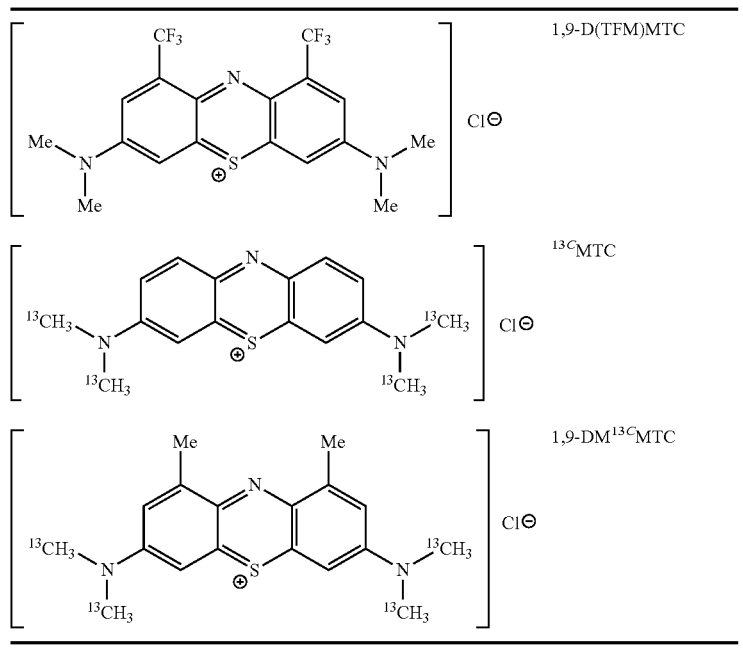

One especially preferred diaminophenothiazinium compound (DAPTC) is MTC:

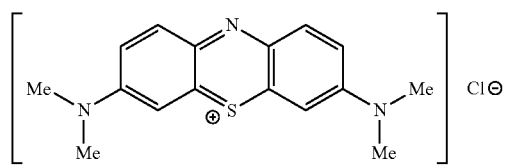

The Acylated Reagent Compound (ARC)

The methods of synthesis and/or purification of a diaminophenothiazinium compound (DAPTC), as defined herein and including, for example, methylthioninium chloride (MTC), proceed via an acylated reagent compound (e.g., an acetylated reagent compound) (ARC). The acylated reagent compound (ARC) is a compound of the following formula:

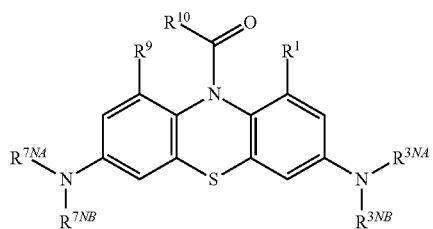

wherein:

$R^1$, $R^9$, $R^{3NA}$, $R^{3NB}$, $R^{7NA}$, and $R^{7NB}$ as defined above; and
$R^{10}$ is independently saturated aliphatic $C_{1-5}$alkyl, phenyl, p-methoxyphenyl, or p-nitrophenyl.

In one embodiment, $R^{10}$ is independently saturated aliphatic $C_{1-5}$alkyl.

In one embodiment, $R^{10}$ is independently saturated linear $C_{1-5}$alkyl.

In one embodiment, $R^{10}$ is independently -Me, -Et, -nPr, -nBu, or -nPe.

In one embodiment, $R^{10}$ is independently -Me (and the acylated reagent compound is an acetylated reagent compound).

The acylated reagent compounds may conveniently be referred to as "3,7-diamino-10-acyl-phenothiazine compounds."

When $R^{10}$ is -Me, the acylated (i.e., acetylated) reagent compounds may conveniently be referred to as "3,7-diamino-10-acetyl-phenothiazine compounds."

In an especially preferred embodiment, the acylated reagent compound (ARC) is 3,7-di(dimethylamino)-10-acetyl-phenothiazine, shown below:

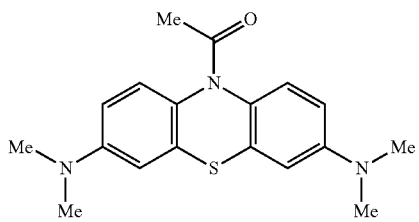 [SMILES: CC(=O)N1c2ccc(N(C)C)cc2Sc2cc(N(C)C)ccc21]

Such acetylated reagent compounds are known, and may be prepared, for example, from corresponding 3,7-diamino-phenothiazin-5-ium compounds, for example, from methylthioninium chloride (MTC), using the following synthesis scheme, which is also illustrated in the examples below, or by using an analogous scheme.

Scheme 3

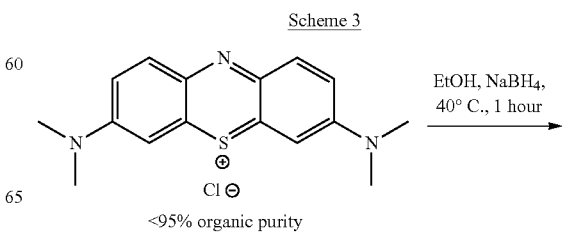

<95% organic purity

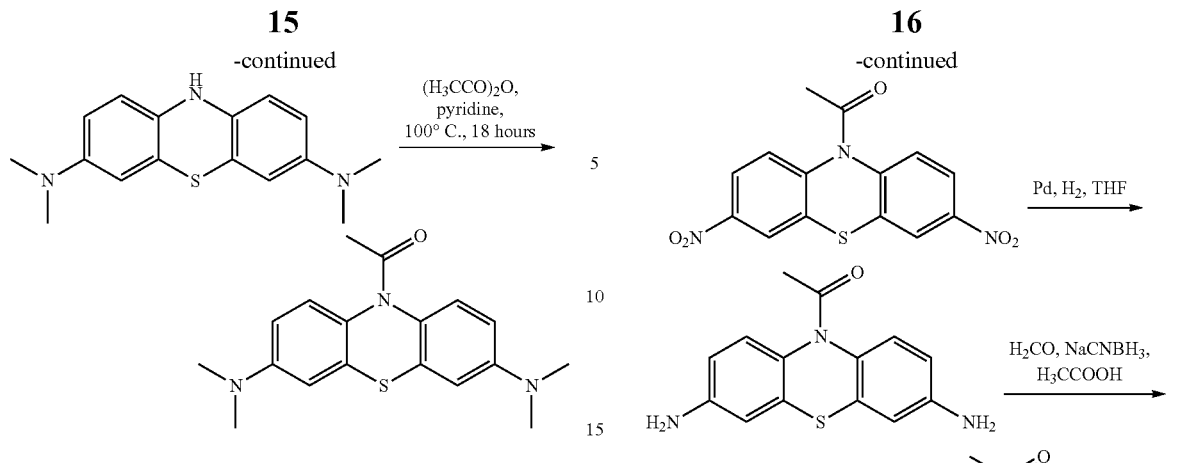

Acylated (e.g., acetylated) reagent compounds may also be obtained using the following synthesis scheme or an analogous scheme. See, for example, Cohn, G., 1900.

Scheme 4

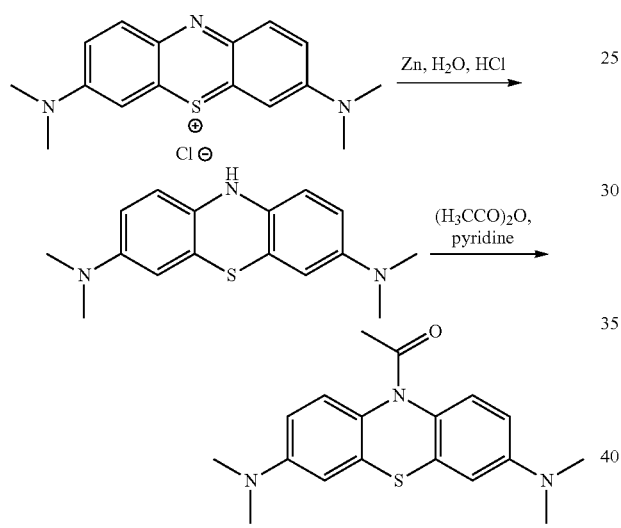

Alternative reducing agents for the first step above have also been used, including phenylhydrazine. See, for example, Drew et al., 1933.

Acylated (e.g., acetylated) reagent compounds may also be obtained using the following synthesis scheme or an analogous scheme. In regard to the first two steps of this synthesis scheme, see, for example, Tomilin et al., 1996.

Scheme 5

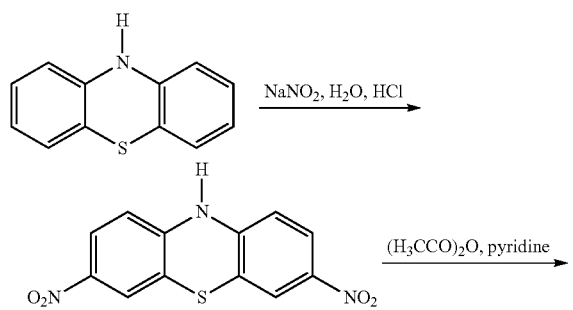

Acylated (e.g., acetylated) reagent compounds may also be obtained using the following synthesis scheme or an analogous scheme. In regard to the first step of this synthesis scheme, see, for example, Leventis et al., 1997.

Scheme 6

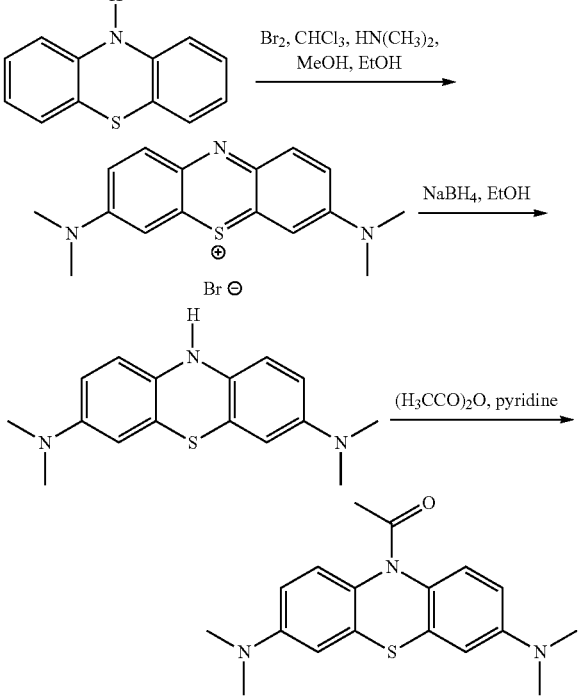

Acylated (e.g., acetylated) reagent compounds may also be obtained using the following synthesis scheme or an analogous scheme. In regard to the first step of this synthesis scheme, see, for example, Gilman et al., 1944.

Scheme 7

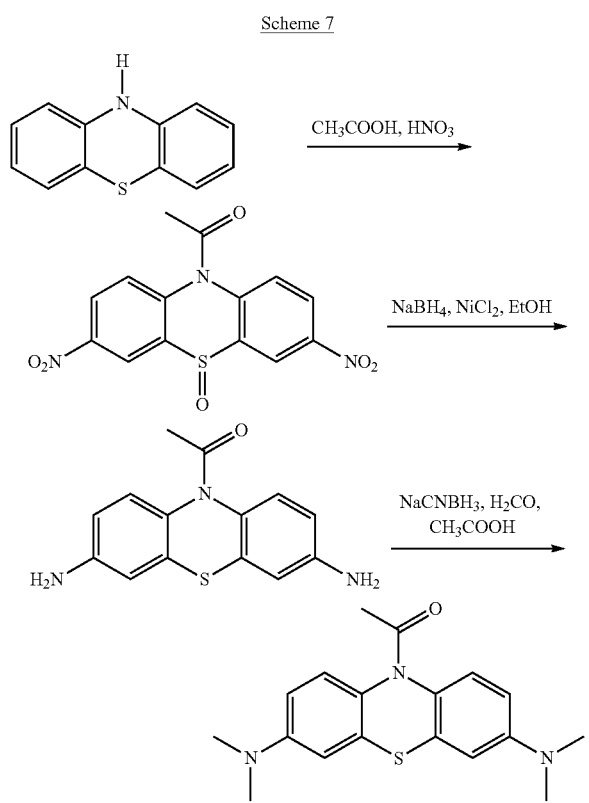

Whatever synthesis route is taken, an acylation (e.g., acetylation) step is involved, specifically, a step of acylating (e.g., acetylating) an upstream precursor of the acylated (e.g., acetylated) reagent compound, and, ultimately, an acylated (e.g., acetylated) reagent compound (ARC) is obtained.

The Non-Acylated Precursor of the Acylated Reagent Compound (NAPARC)

In one embodiment, the acylated reagent compound (ARC) (e.g., the acetylated precursor of the acetylated reagent compound) is obtained from a corresponding non-acylated precursor of the acylated reagent compound (NAPARC) (e.g., a corresponding non-acetylated precursor of the acetylated reagent compound).

In one embodiment, the non-acylated precursor of the acylated reagent compound (NAPARC) (e.g., the acetylated precursor of the acetylated reagent compound) is a compound of the following formula, wherein $R^1$, $R^9$, $R^{3NA}$, $R^{3NB}$, $R^{7NA}$, and $R^{7NB}$ are as defined herein:

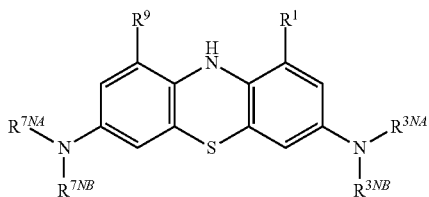

In an especially preferred embodiment, the non-acylated precursor of the acylated reagent compound (NAPARC) is 3,7-di(dimethylamino)-10H-phenothiazine, shown below:

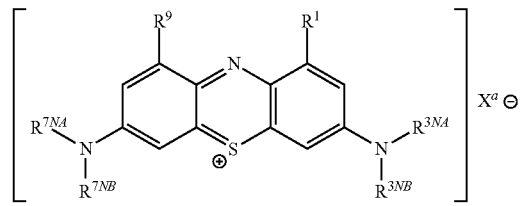

The Oxidized Precursor of the Non-Acylated Precursor of the Acylated Reagent Compound (OPNAPARC)

In one embodiment, the non-acylated precursor of the acylated reagent compound (NAPARC) (e.g., a non-acetylated precursor of the acetylated reagent compound) is obtained from a corresponding oxidized precursor of the non-acylated precursor of the acylated reagent compound (OPNAPARC) (e.g., a corresponding oxidized precursor of the non-acetylated precursor of the acetylated reagent compound).

In one embodiment, the oxidized precursor of the non-acylated precursor of the acylated reagent compound (OPNAPARC) (e.g., the oxidized precursor of the acetylated precursor of the acetylated reagent compound) is a compound of the following formula, wherein $R^1$, $R^9$, $R^{3NA}$, $R^{3NB}$, $R^{7NA}$, and $R^7$ are as defined herein, and wherein $X^a$ is as defined for X, and may be the same as or different than X:

$$\left[\begin{array}{c} R^9 \quad R^1 \\ R^{7NA}\!\!-\!\!N \qquad\qquad N\!\!-\!\!R^{3NA} \\ R^{7NB} \qquad\qquad R^{3NB} \end{array}\right] X^a \ominus$$

In an especially preferred embodiment, the oxidized precursor of the non-acylated precursor of the acylated reagent compound (OPNAPARC) is methyl thioninium chloride (MTC), shown below:

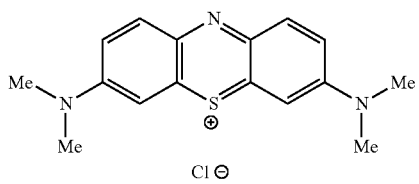 [SMILES: CN(C)c1ccc2nc3ccc(N(C)C)cc3[s+]c2c1 ; [Cl-]]

Upstream Precursors

In an alternative approach, the acylation step is performed further upstream, to give an acylated upstream precursor of the acylated reagent compound (AUPARC) (e.g., an acetylated precursor of the acetylated reagent compound) from a corresponding non-acylated upstream precursor of the acylated reagent compound (NAUPARC) (e.g., a corresponding non-acetylated upstream precursor of the acetylated reagent compound).

The Non-Acylated Upstream Precursor of the Acylated Reagent Compound (NAUPARC)

For example, in one embodiment, the non-acylated upstream precursor of the acylated reagent compound (e.g., the non-acylated upstream precursor of the acetylated reagent compound) falls within one of the following classes of compounds, wherein $R^1$ and $R^9$ are as defined above:

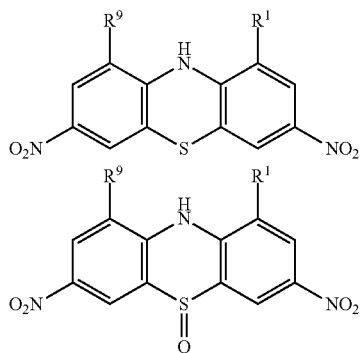

In one preferred embodiment, the non-acylated upstream precursor of the acylated reagent compound (NAUPARC) (e.g., the non-acetylated upstream precursor of the acetylated reagent compound) is a compound of the following formula, wherein $R^1$ and $R^9$ are as defined herein:

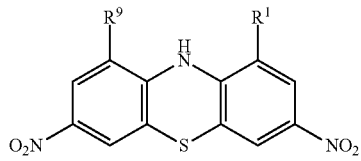

An example of a preferred non-acylated upstream precursor of the acylated reagent compound (NAUPARC) is 3,7-dinitro-10H-phenothiazine, shown below:

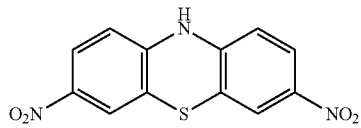 [SMILES: O=[N+]([O-])c1ccc2c(c1)Sc1cc([N+](=O)[O-])ccc1N2]

The Acylated Upstream Precursor of the Acylated Reagent Compound (AUPARC)

In one preferred embodiment, the acylated upstream precursor of the acylated reagent compound (AUPARC) (e.g., the acetylated upstream precursor of the acetylated reagent compound) is a compound of the following formula, wherein $R^1$, $R^9$, and $R^{10}$ as defined herein:

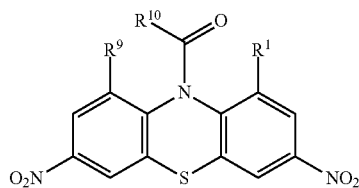

An example of a preferred upstream acylated precursor of the acylated reagent compound (AUPARC) is 3,7-dinitro-10-acetyl-phenothiazine, shown below:

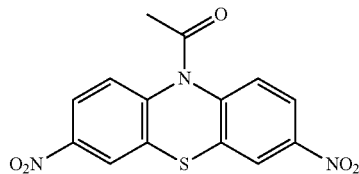 [SMILES: CC(=O)N1c2ccc([N+](=O)[O-])cc2Sc2cc([N+](=O)[O-])ccc21]

Acylated Compounds Generally

Without wishing to be bound by any particular theory, the inventors believe that the use of an acylation step (e.g., an acetylation step), and the formation of an acylated reagent compound (ARC) (e.g., an acetylated reagent compound) or an acylated upstream precursor of the acylated reagent compound (AUPARC) (e.g., an acetylated upstream precursor of the acetylated reagent compound), facilitates the easy removal of many undesired impurities and by-products, and leads, ultimately, to an acylated reagent compound (ARC) (e.g., an acetylated reagent compound) with higher purity, which, in turn, leads to a target diaminophenothiazinium compound (DAPTC) with a higher purity.

For example, Azure B is an undesired impurity often found in samples of methylthioninium chloride (MTC). Commercially available Medex™ contains more than 5% by weight of Azure B (see analysis details below). Removal of Azure B from mixtures of MTC and Azure B is particularly difficult. However, when such a mixture is used as a starting material, and an acetylation step is employed, acetylation of the Azure B leads to a di-acetylated water-soluble by-product that may easily be separated from the desired organic-soluble acetylated reagent compound, for example, by washing with water and recrystallisation. For example, the synthesis and precipitation of the desired acetylated reagent compound, optionally followed by recrystallisation of the precipitated desired acetylated reagent compound, readily achieves removal of much or most or all of the undesired Azure B (presumably in the form of the di-acetylated Azure B by-product) and other organic impurities from the desired acetylated reagent compound.

Azure A and Azure C, among other impurities, are similarly reduced by the same mechanism.

Scheme 8

Azure B      Difficult to separate      MTC

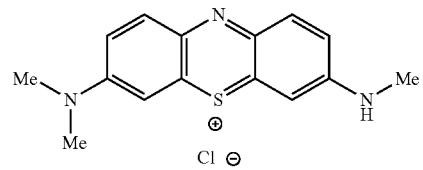 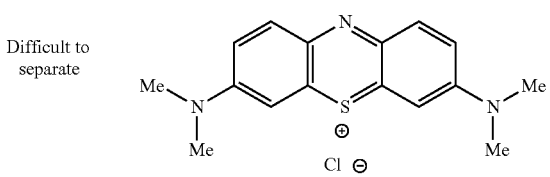

↓ reduction      ↓ reduction

21

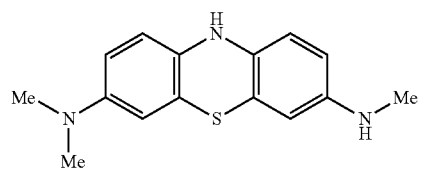

↓ acetylation

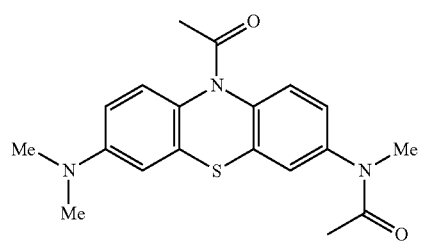

Easy to separate

22

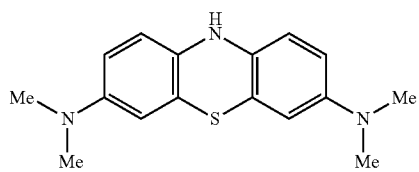

↓ acetylation

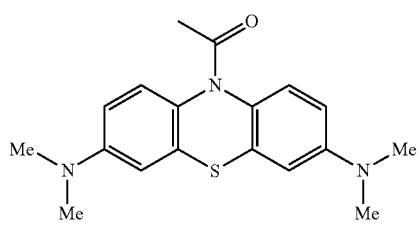

"an acetylated reagent compound"

Methods Generally

For convenience, many of methods described herein may be illustrated using a preferred example as represented in the following scheme.

Scheme 9

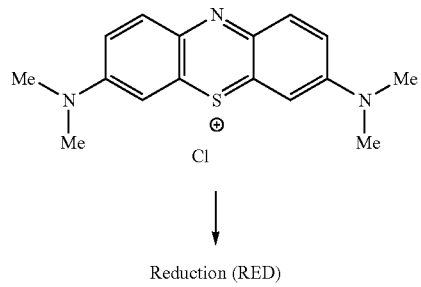

Reduction (RED)

↓

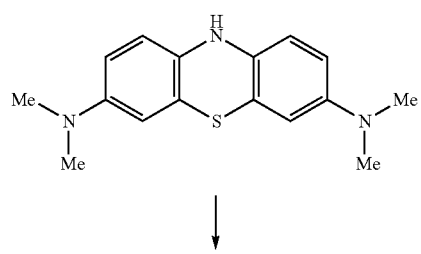

↓

Optional Purification (PUR$^{RED\text{-}AC1}$)

Acylation (AC1) ↘

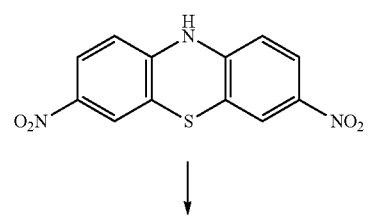

Acylation (AC2)

↓

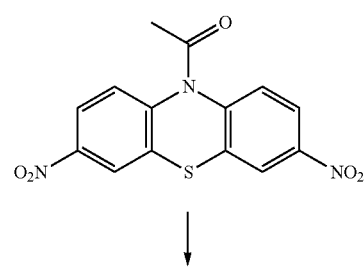

↓

Optional Purification (PUR$^{AC2\text{-}CON}$)

↙ Conversion (CON)

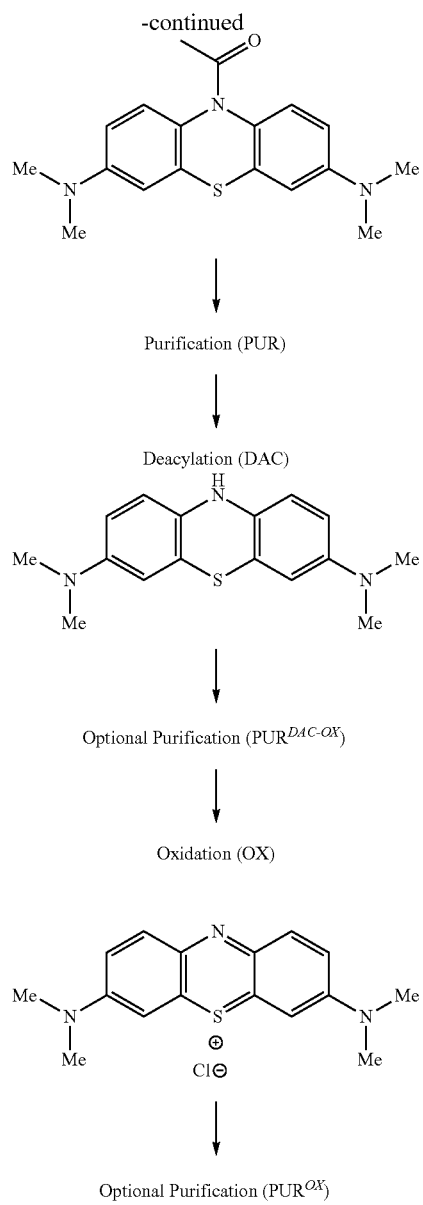

Purification (PUR)

Deacylation (DAC)

Optional Purification (PUR$^{DAC-OX}$)

Oxidation (OX)

Optional Purification (PUR$^{OX}$)

Synthesis and/or Purification of Diaminophenothiazinium Compounds—A

Thus, one aspect of the present invention pertains to a method for the synthesis and/or purification of a diaminophenothiazinium compound (DAPTC), as defined herein and including, for example, methylthioninium chloride (MTC), which method comprises at least the following steps, in order:

purifying (PUR) a corresponding acylated reagent compound (ARC);

deacylating (DAC) said acylated reagent compound (ARC) to give a corresponding deacylated compound; and oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which method comprises at least the following steps, in order:

purifying (PUR) a corresponding acetylated reagent compound;

deacylating (DAC) said acetylated reagent compound to give a corresponding deacetylated compound; and oxidizing (OX) said deacetylated compound to give said diaminophenothiazinium compound.

In one embodiment, the method is as illustrated by the following scheme, in which $R^1$, $R^9$, $R^{10}$, $R^{3NA}$, $R^{3NB}$, $R^{7NA}$, $R^{7NB}$, and X are as defined herein.

Scheme 10

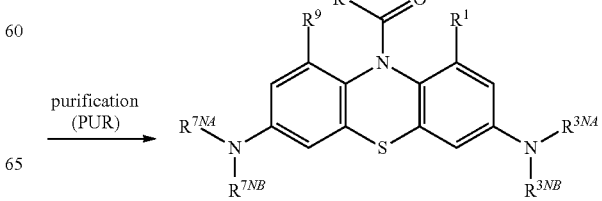

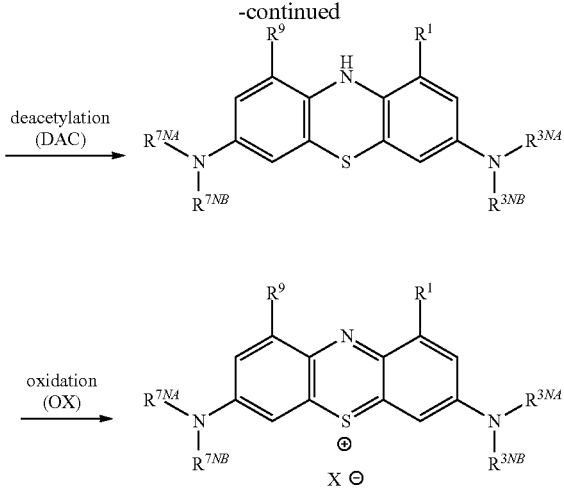

Thus, in one embodiment, the method is a method for the synthesis and/or purification of a diaminophenothiazinium compound (DAPTC), as defined herein and including, for example, methylthioninium chloride (MTC), which method comprises at least the following steps, in order:

purifying (PUR) a corresponding acylated reagent compound (ARC) of the following formula:

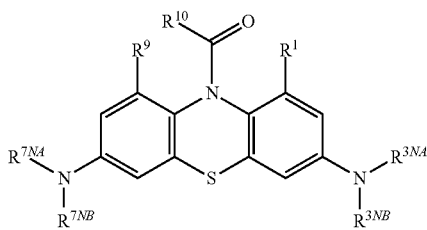

deacylating (DAC) said acylated reagent compound (ARC) to give a corresponding deacylated compound of the following formula:

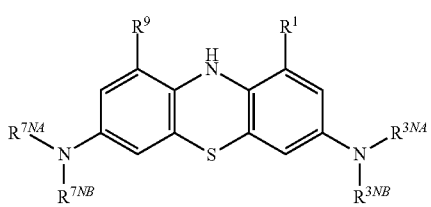

and oxidizing (OX) said deacylated compound to give said diaminophenothiazinium compound (DAPTC).

For example, in one embodiment ("acetyl"), the method is a method for the synthesis and/or purification of a diaminophenothiazinium compound (DAPTC), as defined herein and including, for example, methylthioninium chloride (MTC), which method comprises at least the following steps, in order:

purifying (PUR) a corresponding acetylated reagent compound of the following formula:

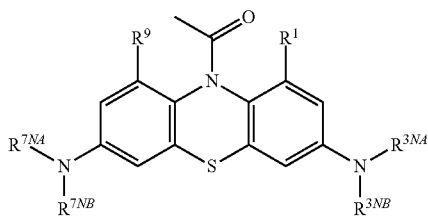

deacylating (DAC) said acetylated reagent compound to give a corresponding deacetylated compound of the following formula:

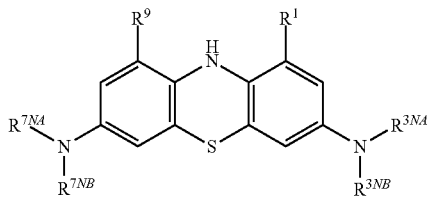

and oxidizing (OX) said deacetylated compound to give said diaminophenothiazinium compound (DAPTC).

For the avoidance of doubt, the word "corresponding" in the phrases "corresponding acylated reagent compound" and "corresponding decylated compound" is intended to mean "corresponding to the target diaminophenothiazinium compound," and so the groups $R^1$, $R^9$, $R^{3NA}$, $R^{3NB}$, $R^{7NA}$, $R^{7NB}$ of the acylated reagent compound and the decylated compound, if present, are the same as the corresponding groups $R^1$, $R^9$, $R^{3NA}$, $R^{3NB}$, $R^{7NA}$, $R^{NB}$ of the target diaminophenothiazinium compound.

The acylated (e.g., acetylated) reagent compound used in said purifying (PUR) step may be obtained from any source or may be obtained using any method of synthesis, for example, using a method of synthesis as described herein.

In a preferred embodiment, the method is a method for the synthesis and/or purification of methylthioninium chloride (MTC), which method comprises at least the following steps, in order:

purifying (PUR) 3,7-di(dimethylamino)-10-acetyl-phenothiazine;

deacylating (DAC) said 3,7-di(dimethylamino)-10-acetyl-phenothiazine to give 3,7-di(dimethylamino)-10H-phenothiazine; and oxidizing (OX) said 3,7-di(dimethylamino)-10H-phenothiazine to give said methylthioninium chloride (MTC).

An example of this embodiment is illustrated in the following scheme.

Scheme 11

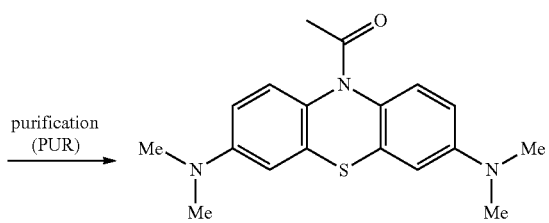

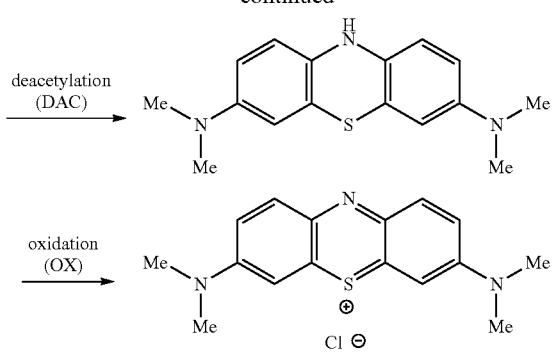

Synthesis and/or Purification of Diaminophenothiazinium Compounds—A+B

In one embodiment, the acylated reagent compound (ARC) used in said purifying (PUR) step is obtained by acylating the non-acylated (e.g., $N^{10}$-unsubstituted) precursor of the corresponding acylated reagent compound (NAPARC).

For example, in one embodiment, where $R^{10}$ is -Me, the acetylated reagent compound used in said purifying (PUR) step is obtained by acetylating the non-acetylated (e.g., $N^{10}$-unsubstituted) precursor of the corresponding acetylated reagent compound.

Thus, in one embodiment, the method further comprises the following step, before said purifying (PUR) step:

acylating (AC1) a corresponding non-acylated precursor of said acylated reagent compound (NAPARC) to give said acylated reagent compound (ARC).

For example, in one embodiment ("acetyl"), the method further comprises the following step, before said purifying (PUR) step:

acylating (AC1) a corresponding non-acetylated precursor of said acetylated reagent compound to give said acetylated reagent compound.

In one embodiment, the method further comprises the following step, before said purifying (PUR) step:

acylating (AC1) a corresponding non-acylated precursor of an acylated reagent compound (NAPARC) to give said acylated reagent compound (ARC), wherein said non-acylated precursor (NAPARC) is a compound of the following formula:

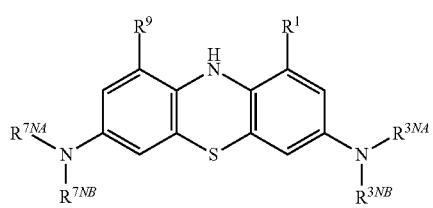

For example, in one embodiment ("acetyl"), the method further comprises the following step, before said purifying (PUR) step:

acylating (AC1) a corresponding non-acetylated precursor of said acetylated reagent compound to give said acetylated reagent compound, wherein said non-acetylated precursor is a compound of the following formula:

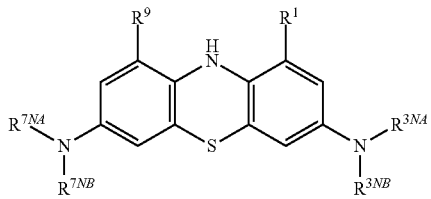

Thus, in one embodiment, the method is a method for the synthesis and/or purification of a diaminophenothiazinium compound (DAPTC), as defined herein and including, for example, methylthioninium chloride (MTC), which method comprises at least the following steps, in order:

acylating (AC1) a corresponding non-acylated precursor of a corresponding acylated reagent compound (NAPARC) to give a corresponding acylated reagent compound (ARC);

purifying (PUR) said acylated reagent compound (ARC);

deacylating (DAC) said acylated reagent compound (ARC) to give a corresponding deacylated compound; and oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which method comprises at least the following steps, in order:

acylating (AC1) a corresponding non-acetylated precursor of a corresponding acetylated reagent compound to give said acetylated reagent compound;

purifying (PUR) said acetylated reagent compound;

deacylating (DAC) said acetylated reagent compound to give a corresponding deacetylated compound; and oxidizing (OX) said deacetylated compound to give said diaminophenothiazinium compound (DAPTC).

In one embodiment, the method is as illustrated by the following scheme, in which $R^1$, $R^9$, $R^{10}$, $R^{3NA}$, $R^{3NB}$, $R^{7NA}$, $R^{7NB}$, and X are as defined herein.

Scheme 12

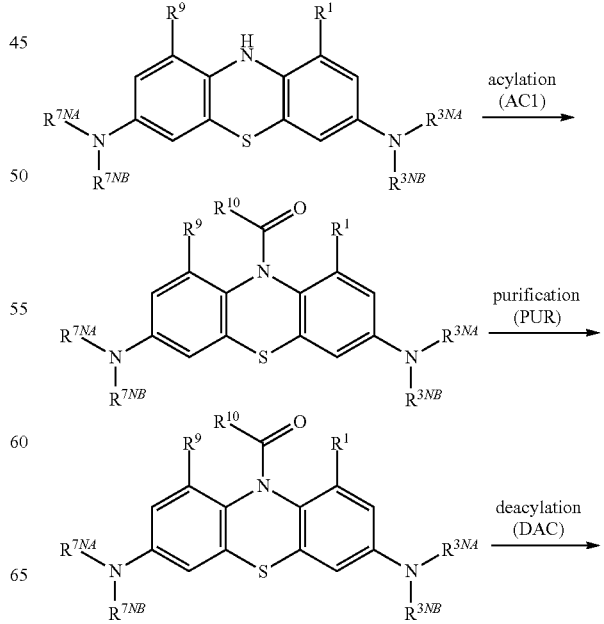

-continued

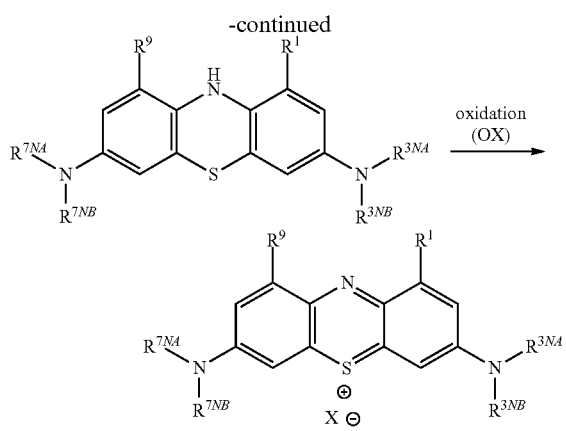

Thus, in one embodiment, the method is a method for the synthesis and/or purification of a diaminophenothiazinium compound, as defined herein and including, for example, methylthioninium chloride (MTC), which comprises at least the following steps, in order:

acylating (AC1) a corresponding non-acylated precursor of a corresponding acylated reagent compound (NAPARC) to give said corresponding acylated reagent compound (ARC), wherein said non-acylated precursor (NAPARC) is a compound of the following formula:

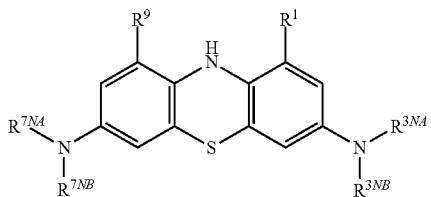

and wherein said acylated reagent compound (ARC) is a compound of the following formula:

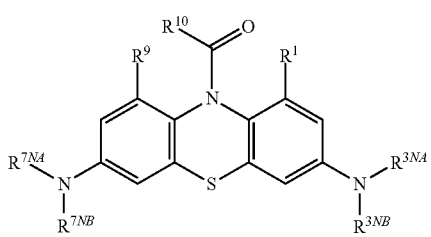

purifying (PUR) said acylated reagent compound (ARC);
deacylating (DAC) said purified acylated reagent compound (ARC) to give a corresponding deacylated compound of the following formula:

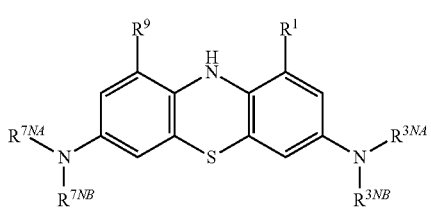

and
oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which comprises at least the following steps, in order:

acylating (AC1) a corresponding non-acetylated precursor of a corresponding acetylated reagent compound to give said acetylated reagent compound;
wherein said non-acetylated precursor is a compound of the following formula:

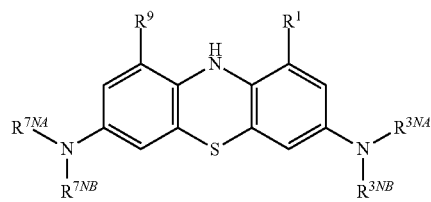

wherein said acetylated reagent compound is a compound of the following formula:

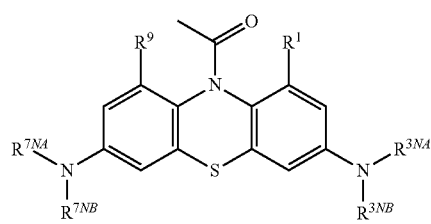

purifying (PUR) said acetylated reagent compound;
deacylating (DAC) said purified acetylated reagent compound to give a corresponding deacetylated compound of the following formula:

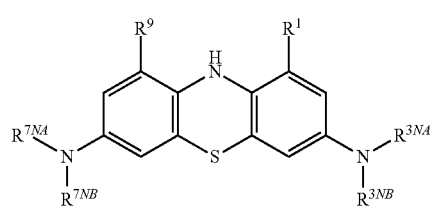

and
oxidizing (OX) said deacetylated compound to give said diaminophenothiazinium compound (DAPTC).

For the avoidance of doubt, the word "corresponding" in the phrases "corresponding non-acylated precursor of a corresponding acylated reagent compound," "corresponding acylated reagent compound" and "corresponding decylated compound" is intended to mean "corresponding to the target diaminophenothiazinium compound," and so the groups $R^1$, $R^9$, $R^{3NA}$, $R^{3NB}$, $R^{7NA}$, $R^{7NB}$ of the non-acylated precursor, the acylated reagent compound, and the decylated compound, if present, are the same as the corresponding groups $R^1$, $R^9$, $R^{3NA}$, $R^{3NB}$, $R^{7NA}$, $R^{7NB}$ of the target diaminophenothiazinium compound.

The non-acylated (e.g., non-acetylated) (e.g., $N^{10}$-unsubstituted) precursor of an acylated (e.g., acetylated) reagent compound used in said acylating (AC1) step may be obtained from any source or may be obtained using any method of synthesis, for example, using a method as described herein.

In a preferred embodiment, the method is a method for the synthesis and/or purification of methylthioninium chloride (MTC), which method comprises at least the following steps, in order:

acylating (AC1) 3,7-di(dimethylamino)-10H-phenothiazine to give 3,7-di(dimethylamino)-10-acetyl-phenothiazine;

purifying (PUR) said 3,7-di(dimethylamino)-10-acetyl-phenothiazine;

deacylating (DAC) said 3,7-di(dimethylamino)-10-acetyl-phenothiazine to give 3,7-di(dimethylamino)-10H-phenothiazine; and oxidizing (OX) said 3,7-di(dimethylamino)-10H-phenothiazine to give said methylthioninium chloride (MTC).

An example of this embodiment is illustrated in the following scheme.

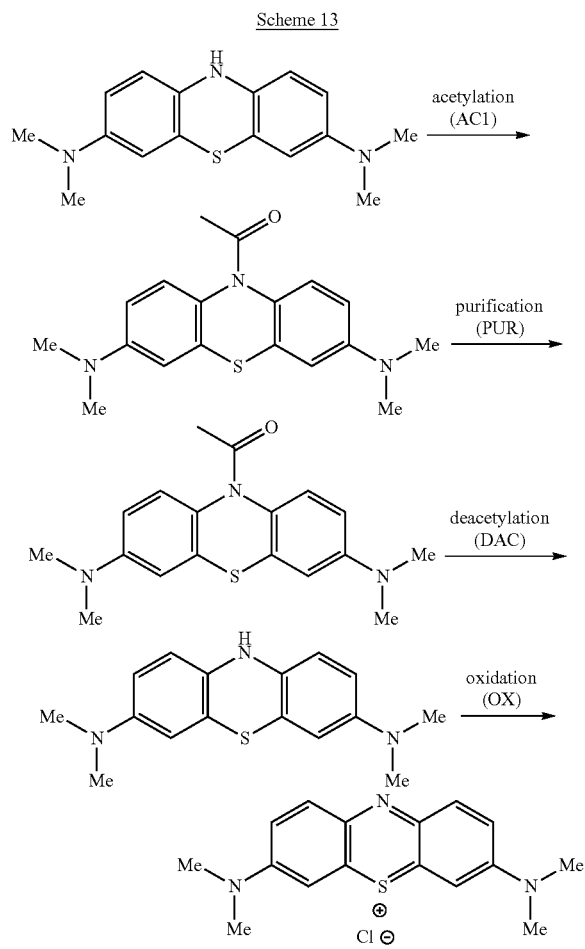

Synthesis and/or Purification of Diaminophenothiazinium Compounds—A+B+C

In one embodiment, the acylated (e.g., acetylated) reagent compound used in said acylating (AC1) step is obtained by reducing a corresponding diaminophenothiazinium compound.

Thus, in one embodiment, the method further comprises the following step, before said acylating (AC1) step:

reducing (RED) a corresponding oxidized precursor of said non-acylated precursor of said acylated reagent compound (OPNAPARC) to give said non-acylated precursor of said acylated reagent compound.

For example, in one embodiment ("acetyl"), the method further comprises the following step, before said acylating (AC1) step:

reducing (RED) a corresponding oxidized precursor of said non-acetylated precursor of said acetylated reagent compound to give said non-acetylated precursor of said acetylated reagent compound.

In one embodiment, the method further comprises the following step, before said acylating (AC1) step:

reducing (RED) a corresponding oxidized precursor of said non-acylated precursor of said acylated reagent compound (OPNAPARC) to give said non-acylated precursor of said acylated reagent compound (NAPARC), wherein said oxidized precursor (OPNARC) is a compound of the following formula, wherein $X^a$ is as defined for X, and may be the same as or different than X:

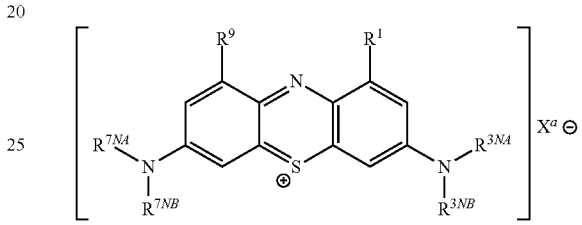

For example, in one embodiment ("acetyl"), the method further comprises the following step, before said acylating (AC1) step:

reducing (RED) a corresponding oxidized precursor of said non-acetylated precursor of said acetylated reagent compound to give said non-acetylated precursor of said acetylated reagent compound, wherein said oxidized precursor is a compound of the following formula, wherein $X^a$ is as defined for X, and may be the same as or different than X:

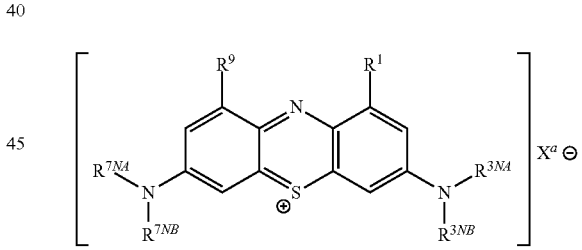

Thus, in one embodiment, the method is a method for the synthesis and/or purification of a diaminophenothiazinium compound, as defined herein and including, for example, methylthioninium chloride (MTC), which method comprises at least the following steps, in order:

reducing (RED) a corresponding oxidized precursor of a corresponding non-acylated precursor of a corresponding acylated reagent compound (OPNAPARC) to give said corresponding non-acylated precursor of said acylated reagent compound (NAPARC);

acylating (AC1) said non-acylated precursor (NAPARC) to give said acylated reagent compound (ARC);

purifying (PUR) said acylated reagent compound (ARC);

deacylating (DAC) said acylated reagent compound (ARC) to give a corresponding deacylated compound; and oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which method comprises at least the following steps, in order:

reducing (RED) a corresponding oxidized precursor of a corresponding non-acetylated precursor of a corresponding acetylated reagent compound to give said non-acetylated precursor of said acetylated reagent compound;

acylating (AC1) said non-acetylated precursor of said acetylated reagent compound to give said acetylated reagent compound;

purifying (PUR) said acetylated reagent compound;

deacylating (DAC) said acetylated reagent compound to give a corresponding deacetylated compound; and oxidizing (OX) said deacetylated compound to give said diaminophenothiazinium compound (DAPTC).

In one embodiment, the method is as illustrated by the following scheme, in which $R^1$, $R^9$, $R^{10}$, $R^{3NA}$, $R^{3NB}$, $R^{7NA}$, $R^{7NB}$, and X are as defined herein, and $X^a$ is as defined for X, and may be the same as or different than X. In one embodiment, $X^a$ and X are the same.

Scheme 14

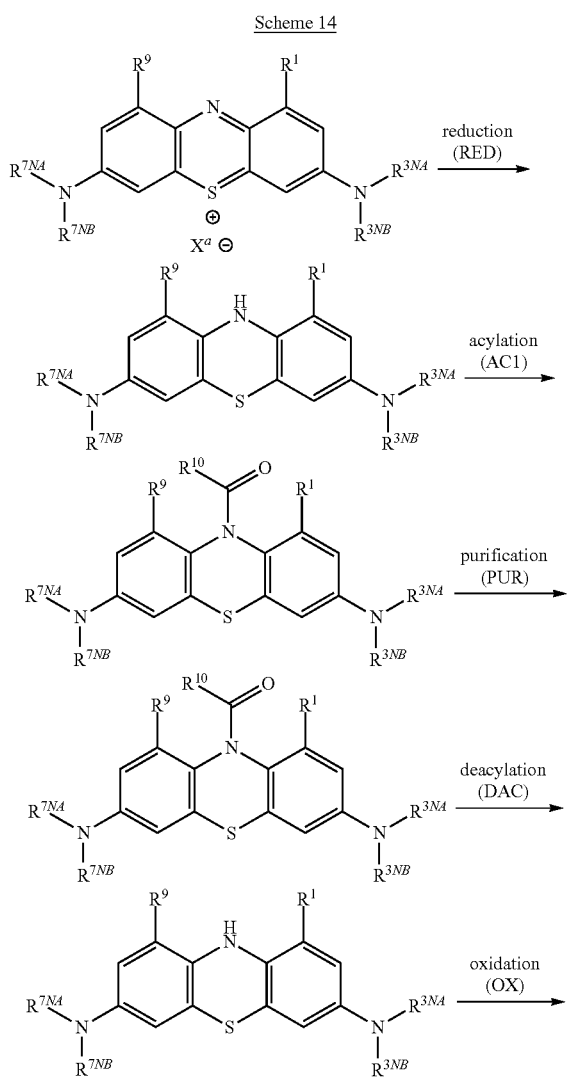

Thus, in one embodiment, the method is a method for the synthesis and/or purification of a diaminophenothiazinium compound, as defined herein and including, for example, methylthioninium chloride (MTC), which method comprises at least the following steps, in order:

reducing (RED) a corresponding oxidized precursor of a corresponding non-acylated precursor of a corresponding acylated reagent compound (OPNAPARC) to give said non-acylated precursor of said acylated reagent compound (NAPARC), wherein said oxidized precursor (OPNAPARC) is a compound of the following formula:

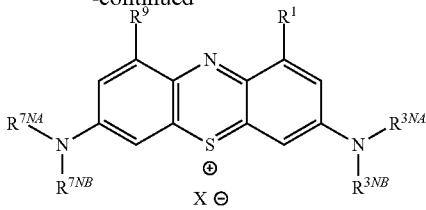

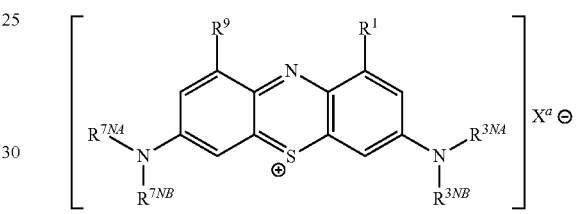

and wherein said non-acylated precursor (NAPARC) is a compound of the following formula:

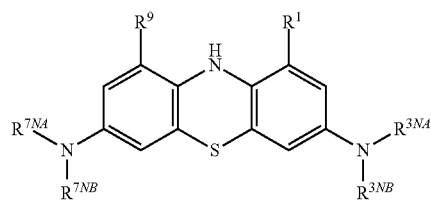

acylating (AC1) said non-acylated precursor of said acylated reagent compound (NAPARC) to give said acylated reagent compound (ARC), wherein said acylated reagent compound (ARC) is a compound of the following formula:

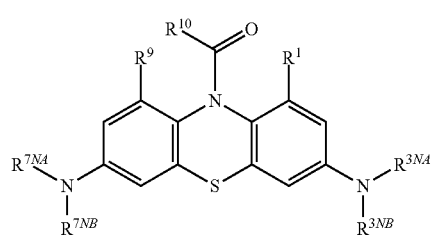

purifying (PUR) said acylated reagent compound (ARC);

deacylating (DAC) said acylated reagent compound (ARC) to give a corresponding deacylated compound of the following formula:

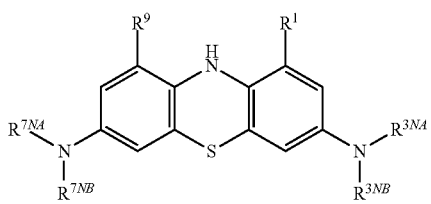

and oxidizing (OX) said deacylated compound to give said diaminophenothiazinium compound (DAPTC).

For example, in one embodiment ("acetyl"), the method comprises at least the following steps, in order:

reducing (RED) a corresponding oxidized precursor of a corresponding non-acetylated precursor of a corresponding acetylated reagent compound to give said non-acetylated precursor of said acetylated reagent compound;

wherein said oxidized precursor is a compound of the following formula:

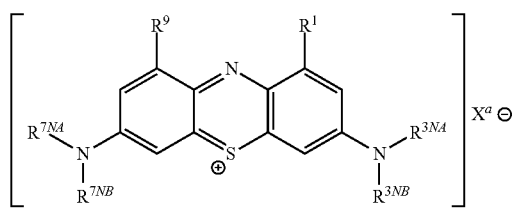

wherein said non-acetylated precursor is a compound of the following formula:

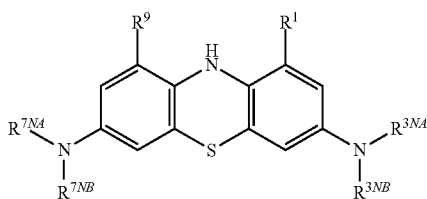

acylating (AC1) said non-acetylated precursor of said acetylated reagent compound to give said acetylated reagent compound, wherein said acetylated reagent compound is a compound of the following formula:

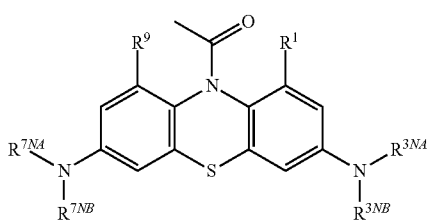

purifying (PUR) said acetylated reagent compound;

deacylating (DAC) said acetylated reagent compound to give a corresponding deacetylated compound of the following formula:

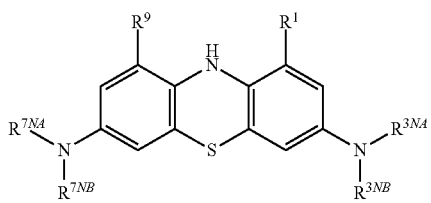

and oxidizing (OX) said deacetylated compound to give said diaminophenothiazinium compound (DAPTC).

Corresponding oxidized precursor of a corresponding non-acetylated precursor of a corresponding acetylated reagent compound.

For the avoidance of doubt, the word "corresponding" in the phrases "a corresponding oxidized precursor of a corresponding non-acetylated precursor of a corresponding acetylated reagent compound," "corresponding non-acylated precursor of a corresponding acylated reagent compound," "corresponding acylated reagent compound" and "corresponding decylated compound" is intended to mean "corresponding to the target diaminophenothiazinium compound," and so the groups $R^1$, $R^9$, $R^{3NA}$, $R^{3NB}$, $R^{7NA}$, $R^{7NB}$ of the oxidized precursor, the non-acylated precursor, the acylated reagent compound, and the decylated compound, if present, are the same as the corresponding groups $R^1$, $R^9$, $R^{3NA}$, $R^{3NB}$, $R^{7NA}$, $R^{7NB}$ of the target diaminophenothiazinium compound.

The oxidized precursor of the non-acylated precursor of the acylated reagent compound (OPNAPARC) (e.g., the oxidized precursor of the non-acetylated precursor of an acetylated reagent compound) used in said reducing (RED) step may be obtained from any source or may be obtained using any method of synthesis, for example, using a method as described herein.

In a preferred embodiment, the method is a method for the synthesis and/or purification of methylthioninium chloride (MTC), which method comprises at least the following steps, in order:

reducing (RED) methylthioninium chloride (MTC) to give 3,7-di(dimethylamino)-10H-phenothiazine;

acylating (AC1) said 3,7-di(dimethylamino)-10H-phenothiazine to give 3,7-di(dimethylamino)-10-acetyl-phenothiazine;

purifying (PUR) said 3,7-di(dimethylamino)-10-acetyl-phenothiazine;

deacylating (DAC) said 3,7-di(dimethylamino)-10-acetyl-phenothiazine to give 3,7-di(dimethylamino)-10H-phenothiazine; and oxidizing (OX) said 3,7-di(dimethylamino)-10H-phenothiazine to give said methylthioninium chloride (MTC).

An example of this embodiment is illustrated in the following scheme.

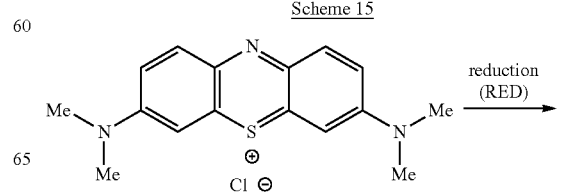

Scheme 15

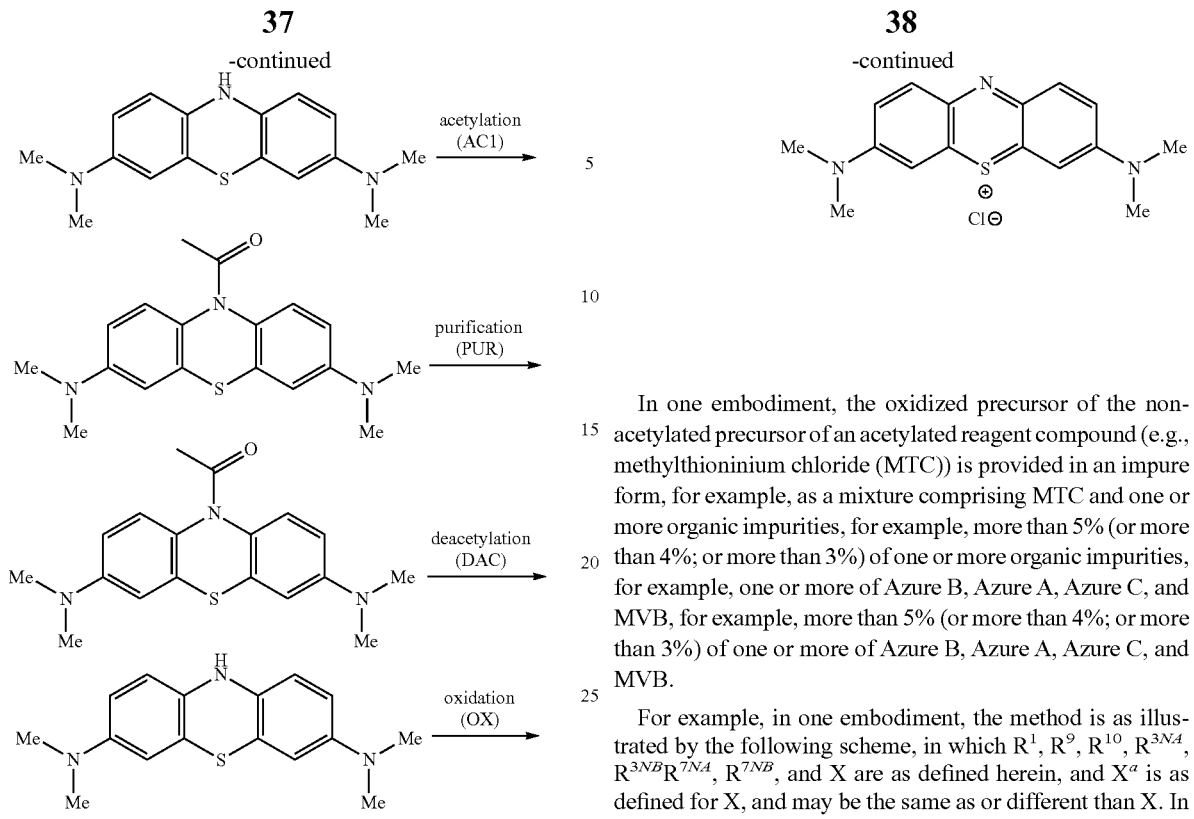

In one embodiment, the oxidized precursor of the non-acetylated precursor of an acetylated reagent compound (e.g., methylthioninium chloride (MTC)) is provided in an impure form, for example, as a mixture comprising MTC and one or more organic impurities, for example, more than 5% (or more than 4%; or more than 3%) of one or more organic impurities, for example, one or more of Azure B, Azure A, Azure C, and MVB, for example, more than 5% (or more than 4%; or more than 3%) of one or more of Azure B, Azure A, Azure C, and MVB.

For example, in one embodiment, the method is as illustrated by the following scheme, in which $R^1$, $R^9$, $R^{10}$, $R^{3NA}$, $R^{3NB}$ $R^{7NA}$, $R^{7NB}$, and X are as defined herein, and $X^a$ is as defined for X, and may be the same as or different than X. In one embodiment, $X^a$ and X are the same.

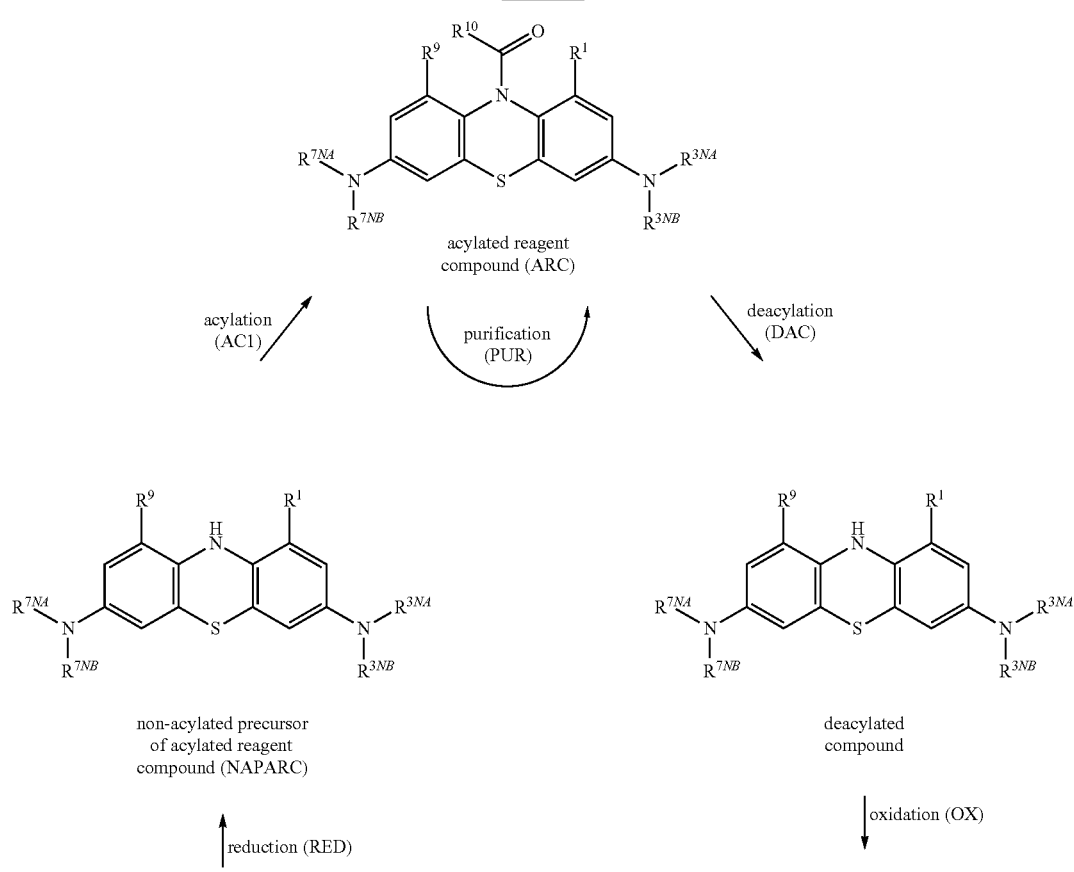

-continued

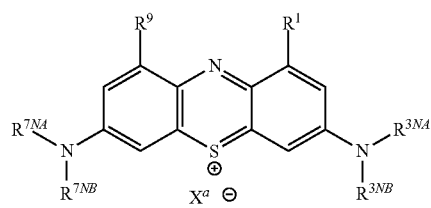

Crude Starting Material
oxidized precursor
of non-acylated precursor
of acylated reagent
compound (OPNAPARC)

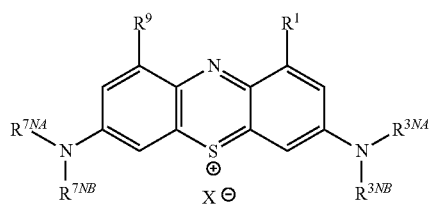

Ultrapure Product

Synthesis and/or Purification of Diaminophenothiazinium Compounds—A+D

In one embodiment, the acylated reagent compound (ARC) used in said purifying (PUR) step is obtained by converting (CON) an acylated upstream precursor of the acylated reagent compound (AUPARC) to the acylated reagent compound (ARC).

For example, in one embodiment, where $R^{10}$ is -Me, the acetylated reagent compound used in said purifying (PUR) step is obtained by converting (CON) an acetylated upstream precursor of the corresponding acetylated reagent compound to the acetylated reagent compound.

Thus, in one embodiment, the method further comprises the following step, before said purifying (PUR) step:

converting (CON) a corresponding acylated upstream precursor of said acylated reagent compound (AUPARC) to said corresponding acylated reagent compound (ARC).

For example, in one embodiment, the method further comprises the following step, before said purifying (PUR) step:

converting (CON) a corresponding acetylated upstream precursor of said acetylated reagent compound to said corresponding acetylated reagent compound.

In one embodiment, the method further comprises the following step, before said purifying (PUR) step:

converting (CON) a corresponding acylated upstream precursor of said acylated reagent compound (AUPARC) to said corresponding acylated reagent compound (ARC), wherein said acylated upstream precursor of said acylated reagent compound (AUPARC) is a compound of the following formula:

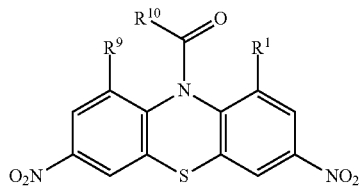

For example, in one embodiment ("acetyl"), the method further comprises the following step, before said purifying (PUR) step:

converting (CON) a corresponding acetylated upstream precursor of said acetylated reagent compound to said corresponding acetylated reagent compound, wherein said acetylated upstream precursor of said acetylated reagent compound is a compound of the following formula:

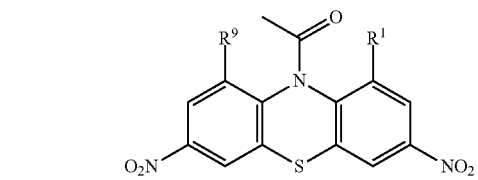

Thus, in one embodiment ("acetyl"), the method is a method for the synthesis and/or purification of a diaminophenothiazinium compound, as defined herein and including, for example, methylthioninium chloride (MTC), which method comprises at least the following steps, in order:

converting (CON) a corresponding acylated upstream precursor of a corresponding acylated reagent compound (AUPARC) to said acylated reagent compound (ARC);

purifying (PUR) said acylated reagent compound (ARC), deacylating (DAC) said acylated reagent compound (ARC) to give a corresponding deacylated compound; and oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which method comprises at least the following steps, in order:

converting (CON) a corresponding acetylated upstream precursor of a corresponding acetylated reagent compound to said acetylated reagent compound;

purifying (PUR) said acetylated reagent compound, deacylating (DAC) said acetylated reagent compound to give a corresponding deacetylated compound; and oxidizing (OX) said deacetylated compound to give said diaminophenothiazinium compound (DAPTC).

In one embodiment, the method is as illustrated by the following scheme, in which $R^1$, $R^9$, $R^{10}$, $R^{3NA}$, $R^{3NB}$, $R^{7NA}$, $R^{7NB}$, and X are as defined herein.

Scheme 17

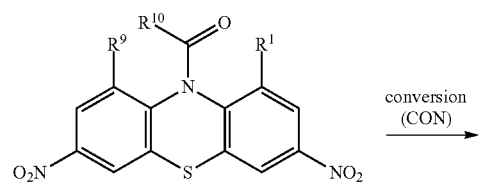

-continued

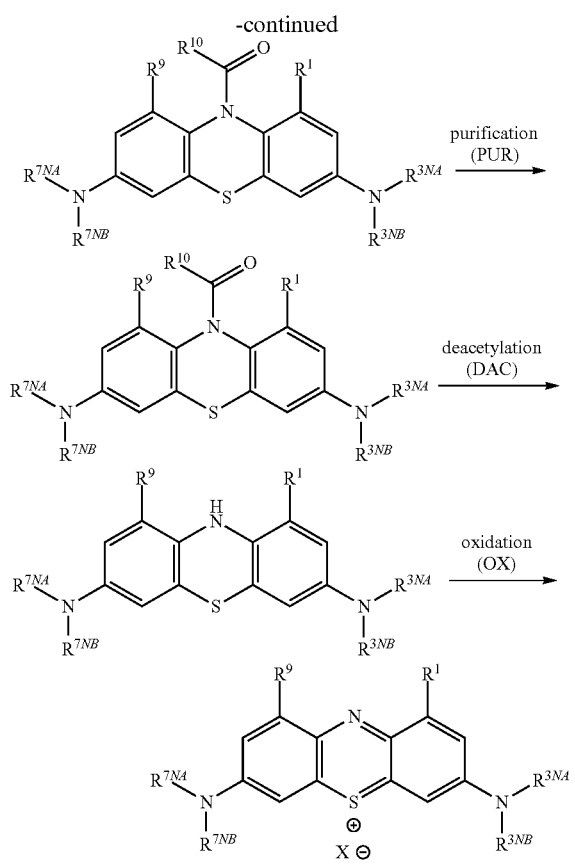

Thus, in one embodiment, the method is a method for the synthesis and/or purification of a diaminophenothiazinium compound, as defined herein and including, for example, methylthioninium chloride (MTC), which method comprises at least the following steps, in order:

converting (CON) a corresponding acylated upstream precursor of a corresponding acylated reagent compound (AU-PARC) to said acylated reagent compound (ARC), wherein said acylated upstream precursor (AUPARC) is a compound of the following formula:

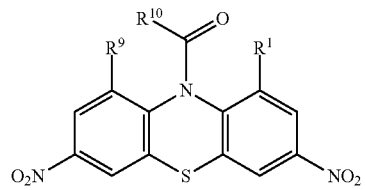

and wherein said acylated reagent compound (ARC) is a compound of the following formula:

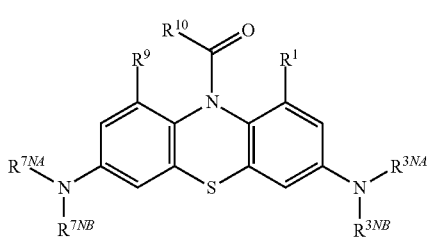

purifying (PUR) said acylated reagent compound (ARC);
deacylating (DAC) said acylated reagent compound (ARC) to give a corresponding deacylated compound of the following formula:

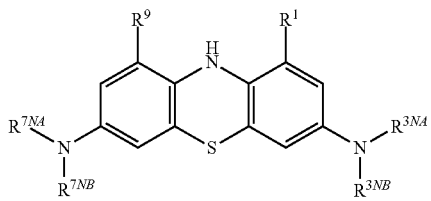

and
oxidizing (OX) said deacylated compound to give said diaminophenothiazinium compound (DAPTC).

For example, in one embodiment ("acetyl"), the method is a method for the synthesis and/or purification of a diaminophenothiazinium compound, as defined herein and including, for example, methylthioninium chloride (MTC), which method comprises at least the following steps, in order:

converting (CON) a corresponding acetylated upstream precursor of a corresponding acetylated reagent compound to said acetylated reagent compound, wherein said acetylated upstream precursor of a corresponding acetylated reagent compound (AUPARC) is a compound of the following formula:

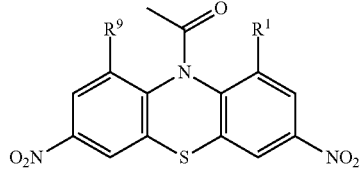

wherein said acetylated reagent compound is a compound of the following formula:

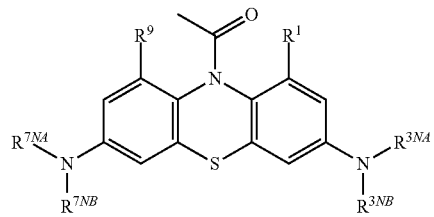

purifying (PUR) said acetylated reagent compound;
deacylating (DAC) said acetylated reagent compound to give a corresponding deacetylated compound of the following formula:

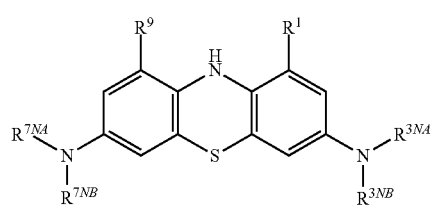

and oxidizing (OX) said deacetylated compound to give said diaminophenothiazinium compound (DAPTC).

For the avoidance of doubt, the word "corresponding" in the phrases "a corresponding acylated upstream precursor of a corresponding acylated reagent compound," "a corresponding acylated reagent compound," and "a corresponding deacylated compound" is intended to mean "corresponding to the target diaminophenothiazinium compound," and so the groups $R^1$, $R^9$, $R^{3NA}$, $R^{3NB}$, $R^{7NA}$, and $R^{7NB}$ of the acylated upstream precursor, the acylated reagent compound, and the deacylated compound, if present, are the same as the corresponding groups $R^1$, $R^9$, $R^{3NA}$, $R^{3NB}$, $R^{7NA}$, $R^{7NB}$ of the target diaminophenothiazinium compound.

In a preferred embodiment, the method is a method for the synthesis and/or purification of methylthioninium chloride (MTC), which method comprises at least the following steps, in order:

converting (CON) 3,7-dinitro-10-acetyl-phenothiazine to 3,7-di(dimethylamino)-10-acetyl-phenothiazine;

purifying (PUR) said 3,7-di(dimethylamino)-10-acetyl-phenothiazine;

deacylating (DAC) said 3,7-di(dimethylamino)-10-acetyl-phenothiazine to give 3,7-di(dimethylamino)-10H-phenothiazine; and oxidizing (OX) said 3,7-di(dimethylamino)-10H-phenothiazine to give said methylthioninium chloride (MTC).

An example of this embodiment is illustrated in the following scheme.

Scheme 18

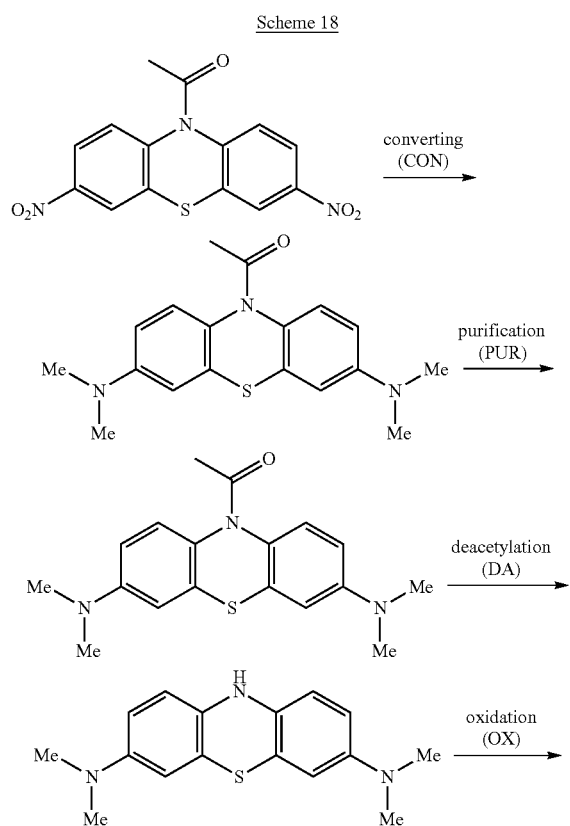

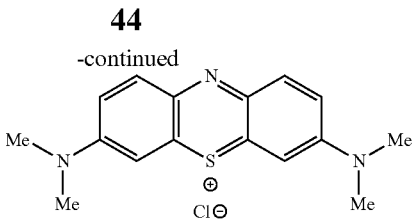

Synthesis and/or Purification of Diaminophenothiazinium Compounds—A+D+E

In one embodiment, the acylated upstream precursor of a corresponding acylated reagent compound (AUPARC) used in said purifying (PUR) step is obtained by acylating the non-acylated (e.g., $N^{10}$-unsubstituted) upstream precursor of the corresponding acylated reagent compound (NAUPARC).

For example, in one embodiment, where $R^{10}$ is -Me, the acetylated upstream precursor of a corresponding acetylated reagent compound used in said purifying (PUR) step is obtained by acetylating the non-acetylated (e.g., $N^{10}$-unsubstituted) upstream precursor of the corresponding acetylated reagent compound.

Thus, in one embodiment, the method further comprises the following step, before said purifying (PUR) step:

acylating (AC2) a corresponding non-acylated upstream precursor of the corresponding acylated reagent compound (NAUPARC) to give said acylated upstream precursor of said corresponding acylated reagent compound (AUPARC).

For example, in one embodiment ("acetyl"), the method further comprises the following step, before said purifying (PUR) step:

acylating (AC2) a corresponding non-acetylated upstream precursor of the corresponding acetylated reagent compound to give said acetylated upstream precursor of said corresponding acetylated reagent compound.

In one embodiment, the method further comprises the following step, before said purifying (PUR) step:

acylating (AC2) a corresponding non-acylated upstream precursor of a corresponding acylated reagent compound (NAUPARC) to give said acylated upstream precursor (AUPARC), wherein said non-acylated upstream precursor (NAUPARC) is a compound of the formula:

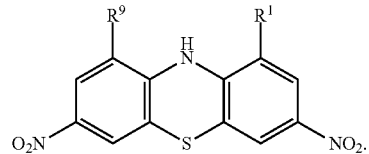

For example, in one embodiment ("acetyl"), the method further comprises the following step, before said purifying (PUR) step:

acylating (AC2) a corresponding non-acetylated upstream precursor of a corresponding acetylated reagent compound to give said acetylated upstream precursor of said corresponding acetylated reagent compound, wherein said non-acetylated upstream precursor is a compound of the formula:

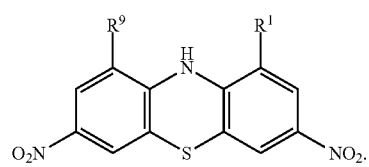

Thus, in one embodiment, the method is a method for the synthesis and/or purification of a diaminophenothiazinium compound (DAPTC), as defined herein and including, for example, methylthioninium chloride (MTC), which method comprises at least the following steps, in order:

acylating (AC2) a corresponding non-acylated upstream precursor of a corresponding acylated reagent compound (NAUPARC) to give said acylated upstream precursor of said corresponding acylated reagent compound (AUPARC);

converting (CON) said acylated upstream precursor (AUPARC) to said corresponding acylated reagent compound (ARC);

purifying (PUR) said acylated reagent compound (ARC);

deacylating (DAC) said acylated reagent compound (ARC) to give a corresponding deacylated compound; and oxidizing (OX) said deacylated compound to give said diaminophenothiazinium compound (DAPTC).

In one embodiment ("acetyl"), the method is a method for the synthesis and/or purification of a diaminophenothiazinium compound (DAPTC), as defined herein and including, for example, methylthioninium chloride (MTC), which method comprises at least the following steps, in order:

acylating (AC2) a corresponding non-acetylated upstream precursor of a corresponding acetylated reagent compound (NAUPARC) to give said acetylated upstream precursor of said corresponding acetylated reagent compound (AUPARC);

converting (CON) said acetylated upstream precursor (AUPARC) to said corresponding acetylated reagent compound (ARC);

purifying (PUR) said acetylated reagent compound (ARC);

deacylating (DAC) said acetylated reagent compound (ARC) to give a corresponding deacetylated compound; and oxidizing (OX) said deacetylated compound to give said diaminophenothiazinium compound (DAPTC).

In one embodiment, the method is as illustrated by the following scheme, in which $R^1$, $R^9$, $R^{10}$, $R^{3NA}$, $R^{3NB}$, $R^{7NA}$, $R^{7NB}$, and X are as defined herein.

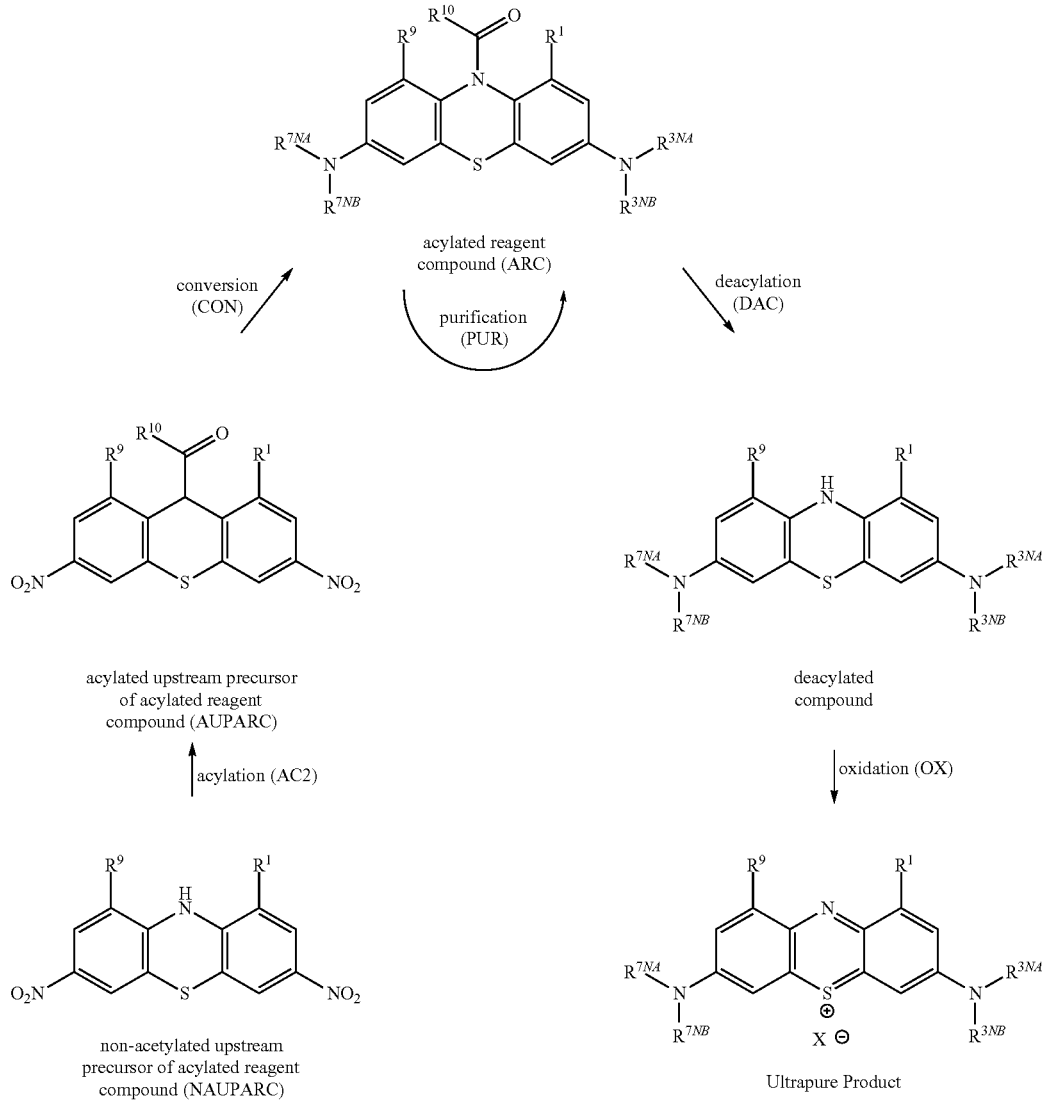

Scheme 19

Thus, in one embodiment, the method is a method for the synthesis and/or purification of a diaminophenothiazinium compound (DAPTC), as defined herein and including, for example, methylthioninium chloride (MTC), which method comprises at least the following steps, in order:

acylating (AC2) a corresponding non-acylated upstream precursor of a corresponding acylated reagent compound (NAUPARC) to give said acylated upstream precursor (AUPARC), wherein said non-acylated upstream precursor (NAUPARC) is a compound of the formula:

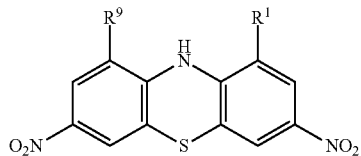

and wherein said acylated upstream precursor (AUPARC) is a compound of the following formula:

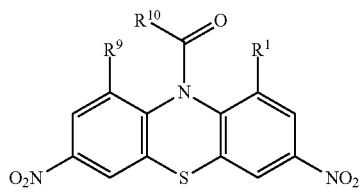

converting (CON) said acylated upstream precursor (AUPARC) to said acylated reagent compound (ARC), wherein said acylated reagent compound (ARC) is a compound of the following formula:

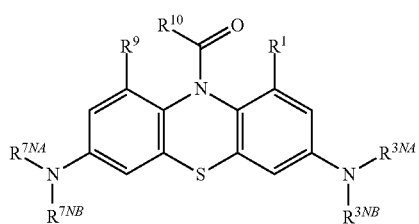

purifying (PUR) said acylated reagent compound (ARC);
deacylating (DAC) said acylated reagent compound (ARC) to give a corresponding deacylated compound of the following formula:

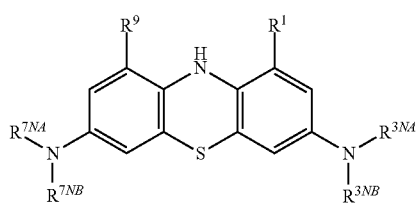

oxidizing (OX) said deacylated compound to give said diaminophenothiazinium compound (DAPTC).

Thus, in one embodiment ("acetyl"), the method is a method for the synthesis and/or purification of a diaminophenothiazinium compound (DAPTC), as defined herein and including, for example, methylthioninium chloride (MTC), which method comprises at least the following steps, in order:

acylating (AC2) a corresponding non-acetylated upstream precursor of a corresponding acetylated reagent compound to give said acetylated upstream precursor of said corresponding acetylated reagent compound, wherein said non-acetylated upstream precursor is a compound of the formula:

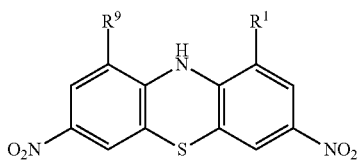

and wherein said acetylated upstream precursor (AUPARC) is a compound of the following formula:

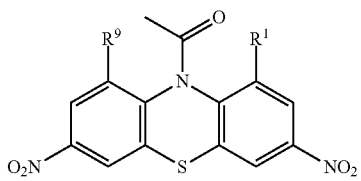

converting (CON) said acetylated upstream precursor (AUPARC) to said acetylated reagent compound (ARC),
wherein said acetylated upstream precursor (AUPARC) is a compound of the following formula:

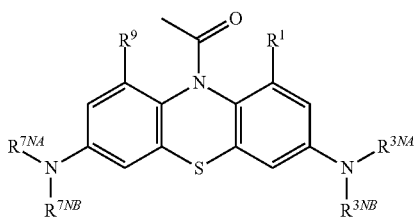

purifying (PUR) said acetylated reagent compound;
deacylating (DAC) said acetylated reagent compound (ARC) to give a corresponding deacetylated compound of the following formula:

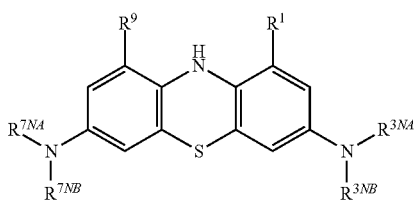

oxidizing (OX) said deacetylated compound to give said diaminophenothiazinium compound (DAPTC).

For the avoidance of doubt, the word "corresponding" in the phrases "a corresponding non-acetylated upstream precursor of a corresponding acetylated reagent compound," "a corresponding acylated upstream precursor of a corresponding acylated reagent compound," "a corresponding acylated reagent compound," and "a corresponding deacylated compound" is intended to mean "corresponding to the target diaminophenothiazinium compound," and so the groups $R^1$, $R^9$, $R^{3NA}$, $R^{3NB}$, $R^{7NA}$, and $R^{7NB}$ of the non-acylated upstream precursor, the acylated upstream precursor, the acylated reagent compound, and the deacylated compound, if present, are the same as the corresponding groups $R^1$, $R^9$, $R^{3NA}$, $R^{3NB}$, $R^{7NA}$, and $R^{7NB}$ of the target diaminophenothiazinium compound.

The non-acylated (e.g., acetylated) upstream precursor of the acylated (e.g., acetylated) reagent compound used in said converting (CON) step may be obtained from any source or may be obtained using any method of synthesis, for example, using a method of synthesis as described herein.

In a preferred embodiment, the method is a method for the synthesis and/or purification of methylthioninium chloride (MTC), which method comprises at least the following steps, in order:

acylating (AC2) 3,7-dinitro-10H-phenothiazine to give 3,7-dinitro-10-acetyl-phenothiazine;

converting (CON) said 3,7-dinitro-10-acetyl-phenothiazine to 3,7-di(dimethylamino)-10-acetyl-phenothiazine;

purifying (PUR) said 3,7-di(dimethylamino)-10-acetyl-phenothiazine;

deacylating (DAC) said 3,7-di(dimethylamino)-10-acetyl-phenothiazine to give 3,7-di(dimethylamino)-10H-phenothiazine; and oxidizing (OX) said 3,7-di(dimethylamino)-10H-phenothiazine to give said methylthioninium chloride (MTC).

An example of this embodiment is illustrated in the following scheme.

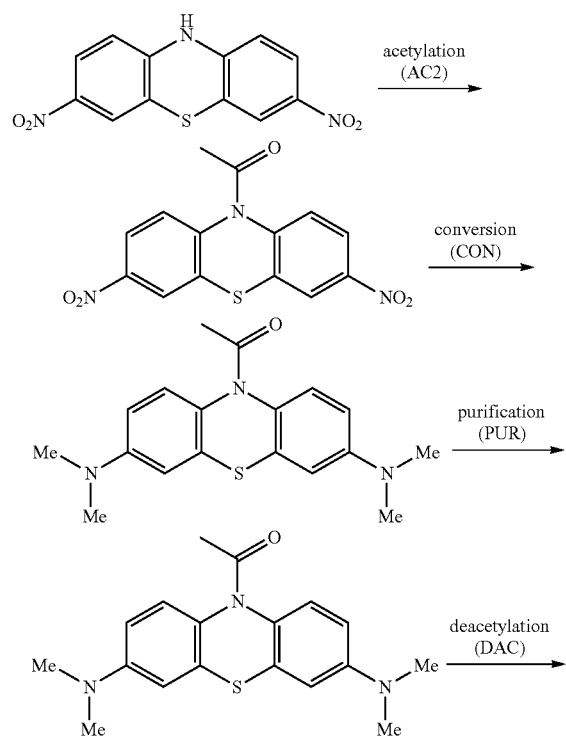

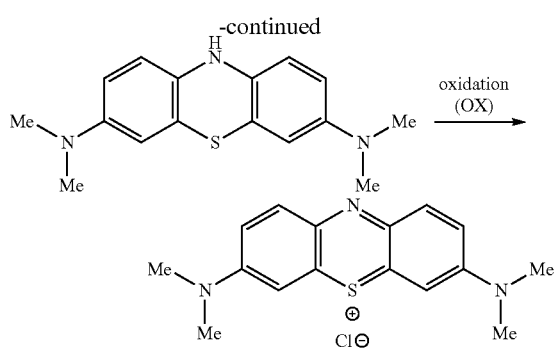

Optional Additional Purification Steps

Optionally, after said reducing (RED) step, and before said acylating (AC1) step, said non-acylated precursor obtained in said reducing (RED) step is purified ($PURR^{RED-AC1}$). This is preferred.

Alternatively, said reducing (RED) step and said acylating (AC1) step are performed in sequence and without isolation or purification of said non-acylated precursor obtained in said reducing (RED) step. In this way, both steps may be performed in a "one-pot" procedure.

Optionally, after said deacylating (DAC) step, and before said oxidizing (OX) step, said deacylated compound obtained in said deacylating (DAC) step is purified ($PUR^{DAC-OX}$). However, this is not preferred.

Alternatively, said deacylating (DAC) step and said oxidizing (OX) step are performed in sequence and without isolation or purification of said deacylated compound obtained in said deacylating (DAC) step. In this way, both steps may be performed in a "one-pot" procedure. This is preferred.

Optionally, after said oxidizing (OX) step, said diaminophenothiazinium compound obtained in said oxidizing (OX) step is purified ($PUR^{OX}$). This purification step is discussed in more detail below.

Optionally, after said acylating (AC2) step, and before said converting (CON) step, said acylated upstream precursor obtained in said acylating (AC2) is purified ($PUR^{AC2-CON}$).

The Reducing (RED) Step

The reducing (RED) step may be performed using any suitable reducing reagents and/or conditions.

In one embodiment, the reducing (RED) step is by reaction with one or more reducing reagents, under reducing step conditions.

In one embodiment, the one or more reducing reagents include sodium borohydride ($NaBH_4$).

In one embodiment, the one or more reducing reagents include methylhydrazine ($MeNHNH_2$).

In one embodiment, the one or more reducing reagents include hydrazine ($NH_2NH_2$) and/or hydrazine hydrate ($NH_2NH_2.H_2O$).

In one embodiment, the reducing step conditions include a reaction temperature for a reaction time.

In one embodiment, the reaction temperature is about 10-70° C.

In one embodiment, the reaction temperature is about 30-50° C.

In one embodiment, the reaction temperature is about 40° C.

In one embodiment, the reaction time is about 10 minutes to 6 hours.

In one embodiment, the reaction time is about 10 minutes to 1 hour.

In one embodiment, the reaction time is about 20 minutes to 3 hours.

In one embodiment, the reaction time is about 20 minutes to 40 minutes.

In one embodiment, the reaction time is about 1 hour.

In one embodiment, the reaction time is about 30 minutes.

In one embodiment, the reducing step conditions include the use of a reducing step solvent.

In one embodiment, the reducing step solvent is ethanol.

In one embodiment, the reducing step solvent is acetonitrile.

In one embodiment, the reducing step conditions include the use of an inert atmosphere.

In one embodiment, the inert atmosphere is argon (e.g., dry argon).

In one embodiment, the inert atmosphere is nitrogen (e.g., dry nitrogen).

For example, in one embodiment, the diaminophenothiazinium compound (~27 mmol), ethanol (75 cm$^3$) and sodium borohydride (~53 mmol) are combined under an atmosphere of argon, and the resulting mixture is heated at ~40° C. for ~1 hour with stirring. The resulting suspension is then cooled to ~5° C. and filtered under argon, washed with ethanol (~20 cm$^3$), and dried under vacuum to give desired reduced product.

For example, in one embodiment, the diaminophenothiazinium compound (~27 mmol), acetonitrile (50 cm$^3$) and sodium borohydride (~35 mmol) are combined under an atmosphere of argon, and the resulting mixture is heated at ~65° C. for ~20 minutes with stirring. The resulting suspension is then cooled to ~5° C. to give desired reduced product.

In another example, methylhydrazine (~59 mmol; ~54 mmol) is used instead of sodium borohydride.

In another example, hydrazine monohydrate (~120 mmol; ~59 mmol) is used instead of sodium borohydride.

The Acylating (AC1) Step and the Acylating (AC2) Step

The acylating (AC1) step and the acylating (AC2) step may be performed using any suitable acylating (e.g., acetylating) reagents and/or conditions.

In one embodiment, the acylating (AC1) step and the acylating (AC2) step is by reaction with one or more acylating reagents, under acylating step conditions.

In one embodiment, the acylating (AC1) step is an acetylating step.

In one embodiment, the acylating (AC2) step is an acetylating step.

In one embodiment, the one or more acylating reagents include acetic anhydride ($CH_3CO)_2O$.

In one embodiment, the acylating step conditions include the use of an acylating step solvent.

In one embodiment, the acylating step solvent is a basic solvent.

In one embodiment, the acylating step solvent is pyridine.

In one embodiment, the acylating step solvent is N,N-diisopropylethylamine.

In one embodiment, the acylating step conditions include a reaction temperature for a reaction time.

In one embodiment, the reaction temperature is about 90-150° C.

In one embodiment, the reaction temperature is about 110-130° C.

In one embodiment, the reaction temperature is about 120° C.

In one embodiment, the reaction temperature is about 80-110° C.

In one embodiment, the reaction temperature is about 80-100° C.

In one embodiment, the reaction temperature is about 90° C.

In one embodiment, the reaction time is about 30 minutes to 30 hours.

In one embodiment, the reaction time is about 12 hours to 24 hours.

In one embodiment, the reaction time is about 12 hours to 18 hours.

In one embodiment, the reaction time is about 18 hours.

In one embodiment, the reaction time is about 30 minutes to 4 hours.

In one embodiment, the reaction time is about 1 hour to 3 hours.

In one embodiment, the reaction time is about 2 hours.

For example, in one embodiment, the reduced compound (~20 mmol), added acetic anhydride (~40 cm$^3$) and pyridine (~10 cm$^3$) are combined, and the resulting mixtures is heated at ~120° C. for ~18 hours with stirring. The mixture is then cooled and then poured carefully over ice-water while stirring to give a solid, which is filtered, washed with water (~100 cm$^3$), and dried in an oven at ~60° C. to give the desired acetylated reagent compound.

For example, in one embodiment, the reduced compound (~20 mmol), added acetic anhydride (~25 cm$^3$), and N,N-diisopropylethylamine (~9 cm$^3$) are combined, and the resulting mixtures is heated at ~90° C. for ~2 hours with stirring. The mixture is then cooled and had water (50 cm$^3$) added while stirring to give a solid, which is filtered, washed with water (4×6 cm$^3$), and dried in an oven at ~60° C. to give the desired acetylated reagent compound.

The Purification (PUR) Step

The purification (PUR) step may be performed using any suitable means of purification.

In one embodiment, the purification (PUR) step comprises precipitation (e.g., of a reaction product) to form a precipitate, followed by collection of the precipitate (e.g., by filtration).

Optionally, the purification (PUR) step further comprises the subsequent step of washing of the precipitate one or more (e.g., 1, 2, 3, 4) times, for example, with a suitable washing solvent.

In one embodiment, the purification (PUR) step comprises precipitation (e.g., of a reaction product), followed by collection of the precipitate (e.g., by filtration), followed by washing of the precipitate one or more (e.g., 1, 2, 3, 4) times, for example, with a suitable washing solvent.

Optionally, the purification further comprises, after collecting the precipitate and/or after washing the precipitate, a step of drying the precipitate or the washed precipitate, for example, drying in an oven and/or drying under vacuum.

In one embodiment, the purification (PUR) step comprises precipitation (e.g., of a reaction product), collection of the precipitate (e.g., by filtration), followed by drying of the washed precipitate.

In one embodiment, the purification (PUR) step comprises precipitation (e.g., of a reaction product), collection of the precipitate (e.g., by filtration), followed by washing of the precipitate one or more (e.g., 1, 2, 3, 4) times, for example, with a suitable washing solvent, followed by drying of the washed precipitate.

In one embodiment, the purification (PUR) step comprises, or further comprises, recrystallisation.

In one embodiment, the recrystallisation comprises: adding the compound to a suitable solvent; heating the mixture to dissolve (preferably fully dissolve) the compound; cooling the heated mixture or allowing the heated mixture to cool so as to allow the compound to precipitate; and collecting the precipitate (e.g., by filtration).

Optionally, the recrystallisation further comprises the subsequent step of washing the precipitate one or more (e.g., 1, 2, 3, 4) times, for example, with a suitable washing solvent, for example, the same solvent used to dissolve the compound.

For example, in one embodiment, the recrystallisation is performed by adding the compound (e.g., 3,7-dimethylamino-10-acetyl-phenothiazine) (~20 mmol) to ethanol (~25 cm$^3$), heating the mixture to ~78° C., cooling the heated mixture to ~5° C. so as to allow the compound to precipitate, and filtering the mixture to collect the precipitate. The precipitate is then washed with ethanol (e.g., 3×6 cm$^3$). The washed precipitate is then dried in an oven at ~60° C. for ~3 hours.

In one embodiment, the purification (PUR) step is, or further comprises, a step of treatment with activated charcoal (also known as activated carbon); for example, adding activated charcoal, followed by filtering to remove the charcoal. This step may be performed, for example, using a solution of the compound in a suitable solvent.

In one embodiment, the step of treatment with activated charcoal comprises: adding the compound to a suitable solvent to dissolve (preferably fully dissolve) the compound; adding activated charcoal to the mixture; filtering the mixture to remove the charcoal.

The resulting filtrate may be used in a subsequent step, for example, the deacylation (DAC) step.

Optionally, this step of treatment with activated charcoal may be performed, for example, in combination with recrystallisation.

For example, in one embodiment, the purification (PUR) step is, or comprises: adding the compound to a suitable solvent; heating the mixture to dissolve (preferably fully dissolve) the compound; adding activated charcoal to the mixture; filtering the mixture to remove the charcoal; cooling the heated mixture or allowing the heated mixture to cool so as to allow the compound to precipitate; and collecting the precipitate (e.g., by filtration).

For example, in one embodiment, the recrystallisation is performed by adding the compound (e.g., 3,7-dimethylamino-10-acetyl-phenothiazine) (~20 mmol) to ethanol (~100 cm$^3$), heating the mixture to ~78° C. until all of the compound has dissolved, adding activated charcoal (~1 g), filtering to remove the charcoal; cooling the heated mixture to ~5° C. so as to allow the compound to precipitate, and filtering the mixture to collect the precipitate. The precipitate is then washed with ethanol (e.g., once, with ~20 cm$^3$). The washed precipitate is then dried in an oven at ~60° C. for ~3 hours.

The Converting (CON) Step

The converting (CON) step may be performed using any suitable reagents and/or conditions.

In one embodiment, the converting (CON) step is by reaction with one or more converting reagents, under converting step conditions.

In one embodiment, the converting (CON) step comprises (i) a nitro reduction step and (ii) a subsequent amino alkylation step.

For example, in one embodiment, the step of: converting (CON) 3,7-dinitro-10-acetyl-phenothiazine to 3,7-di(dimethylamino)-10-acetyl-phenothiazine comprises the steps of:

(i) reducing 3,7-dinitro-10-acetyl-phenothiazine to give 3,7-diamino-10-acetyl-phenothiazine and subsequently (ii) methylating 3,7-diamino-10-acetyl-phenothiazine to give 3,7-di(dimethylamino)-10-acetyl-phenothiazine.

In one embodiment, the nitro reduction step is by reaction with one or more nitro reduction reagents, under nitro reduction step conditions.

In one embodiment, the one or more nitro reduction reagents include palladium.

In one embodiment, the one or more nitro reduction reagents include palladium and hydrogen.

In one embodiment, the nitro reduction step is by reaction with palladium and hydrogen.

In one embodiment, the nitro reduction step conditions include a reaction temperature for a reaction time.

In one embodiment, the reaction temperature is about 40-100° C.

In one embodiment, the reaction temperature is about 50-70° C.

In one embodiment, the reaction temperature is about 60° C.

In one embodiment, the reaction time is about 1 to 36 hours.

In one embodiment, the reaction time is about 12 to 24 hours.

In one embodiment, the reaction time is about 18 hours.

In one embodiment, the nitro reduction step conditions include the use of a nitro reduction step solvent.

In one embodiment, the nitro reduction step solvent is tetrahydrofuran.

For example, in one embodiment, a mixture of acylated upstream precursor (e.g., 3,7-dinitro-10-acetyl-phenothiazine) (~6 mmol), palladium 10% on dry carbon (~0.2 g) and tetrahydrofuran (~20 cm$^3$) is heated to 60° C. under an atmosphere of hydrogen and stirred at this temperature for ~18 hours. The mixture is cooled to room temperature, poured over celite filter aid, and washed with tetrahydrofuran (~10 cm$^3$). The THF filtrate is acidified with hydrochloric acid (~10 M, ~4 cm$^3$) to precipitate the product as a solid. The suspension is filtered to give the desired compound, which is dried at ~60° C. for ~3 hours.

In one embodiment, the amino alkylation step is by reaction with one or more amino alkylation reagents, under amino alkylation step conditions.

In one embodiment, the one or more amino alkylation reagents include sodium cyano borohydride (NaCNBH$_3$) and paraformaldehyde ((H$_2$CO)$_n$).

In one embodiment, the amino alkylation step is by reaction with sodium cyano borohydride (NaCNBH$_3$) and paraformaldehyde ((H$_2$CO)$_n$).

In one embodiment, the amino alkylation step conditions include a reaction temperature for a reaction time.

In one embodiment, the reaction temperature is about 20-80° C.

In one embodiment, the reaction temperature is about 30-70° C.

In one embodiment, the reaction temperature is about 50° C.

In one embodiment, the reaction time is about 10 minutes to 6 hours.

In one embodiment, the reaction time is about 1 to 3 hours.

In one embodiment, the reaction time is about 2 hours.

In one embodiment, the amino alkylation step conditions include the use of an amino alkylation step solvent.

In one embodiment, the amino alkylation step solvent is acetic acid.

For example, in one embodiment, an acid salt of a nitro-reduced acylated upstream precursor (e.g., 3,7-diamino-10-acetyl-phenothiazine dihydrochloride) (~7.5 mmol) is dissolved in water and sodium hydroxide solution added to obtain a precipitate. The solid is filtered to give the free amine, which is dissolved in acetic acid (~20 cm$^3$), and p-formaldehyde (~150 mmol) and sodium cyanoborohydride (~75 mmol) is added. The mixture is stirred at ~50° C. for ~2 hours, after which water (~50 cm³) is added and the solid is filtered to give crude product, which is crystallized from ethanol.

The Deacylating (DAC) Step

The deacylating (DAC) step may be performed using any suitable deacylating reagents and/or conditions.

In one embodiment, the deacylating (DAC) step is by reaction with one or more deacylating reagents, under deacylating step conditions.

In one embodiment, the one or more deacylating reagents include a Bronsted acid.

In one embodiment, the one or more deacylating reagents include an inorganic Bronsted acid.

In one embodiment, the one or more deacylating reagents include a hydrohalic acid, for example, hydrochloric acid (HCl), hydrobromic acid (HBr), or hydroiodic acid (HI).

In one embodiment, the one or more deacylating reagents include hydrochloric acid.

For example, in one embodiment, the deacylating step is by reaction with hydrochloric acid (HCl).

In one embodiment, the deacylation step conditions include a reaction temperature for a reaction time.

In one embodiment, the reaction temperature is about 60-100° C.

In one embodiment, the reaction temperature is about 70-90° C.

In one embodiment, the reaction temperature is about 80° C.

In one embodiment, the reaction time is about 10 minutes to 6 hours.

In one embodiment, the reaction time is about 20 minutes to 3 hours.

In one embodiment, the reaction time is about 1 hour.

In one embodiment, the deacylating step conditions include the use of a deacylating step solvent.

In one embodiment, the deacylating step solvent is water.

For example, in one embodiment, the acylated reagent compound (~3 mmol), water (~10 cm³), and hydrochloric acid (~10 M, ~3 cm³) are combined, and the resulting mixture is heated at ~80° C. for ~1 hour with stirring. The resulting reaction product mixture contains the deacylated product.

For example, in one embodiment, the acylated reagent compound (~20 mmol), water (~14 cm³), and hydrochloric acid (~10 M, ~6.6 cm³) are combined, and the resulting solution is treated with activated charcoal (1 g), filtered, and the reaction mixture is heated at ~80° C. for ~1 hour with stirring. The resulting reaction product mixture contains the deacylated product.

The Oxidizing (OX) Step

The oxidizing (OX) step may be performed using any suitable oxidizing reagents and/or conditions.

In one embodiment, the oxidizing (OX) step is by reaction with one or more oxidizing reagents, under oxidizing step conditions.

In one embodiment, the one or more oxidizing reagents include a Lewis acid.

In one embodiment, the one or more oxidizing reagents include $FeCl_3$, provided for example, as a hydrate, for example, as $FeCl_3.6H_2O$.

In one embodiment, the one or more oxidizing reagents include a nitrite.

In one embodiment, the one or more oxidizing reagents include a $C_{1-6}$alkyl nitrite.

In one embodiment, the one or more oxidizing reagents include isoamyl nitrite.

In one embodiment, the one or more oxidizing reagents include t-butyl nitrite.

In one embodiment, the one or more oxidizing reagents include an Amberlite resin I. R. 120 (an anion exchange resin), which, in the present case, acts as an oxidizing agent.

In one embodiment, the oxidizing step conditions include a reaction temperature for a reaction time.

In one embodiment, the reaction temperature is about 1-25° C.

In one embodiment, the reaction temperature is about 1-15° C.

In one embodiment, the reaction temperature is about 1-10° C.

In one embodiment, the reaction temperature is about 1-10° C.

In one embodiment, the reaction temperature is about 2-10° C.

In one embodiment, the reaction temperature is about 1-9° C.

In one embodiment, the reaction temperature is about 2-9° C.

In one embodiment, the reaction temperature is about 1-8° C.

In one embodiment, the reaction temperature is about 2-8° C.

In one embodiment, the reaction temperature is about 1-7° C.

In one embodiment, the reaction temperature is about 2-7° C.

In one embodiment, the reaction temperature is about 1-6° C.

In one embodiment, the reaction temperature is about 2-6° C.

In one embodiment, the reaction temperature is about 1-5° C.

In one embodiment, the reaction temperature is about 2-5° C.

In one embodiment, the reaction temperature is about 5° C.

Without wishing to be bound by any particular theory, the inventors believe that by employing a relatively low oxidizing step temperature (e.g., below ~10° C.; e.g., below ~5° C.), the production of undesired by-products (including, e.g., the reintroduction of Azure B, etc.) can be minimized and the purity of the final product can be maximized.

In one embodiment, the reaction time is about 5 minutes to 3 hours.

In one embodiment, the reaction time is about 15 minutes to 2 hours.

In one embodiment, the reaction time is about 30 minutes.

In one embodiment, the oxidizing step conditions include the use of an oxidizing step solvent.

In one embodiment, the oxidizing step solvent is water.

For example, in one embodiment, the reaction product mixture obtained by the deacylating (DAC) step and containing the deacylated product (~3 mmol) is cooled to ~5° C., and a cooled aqueous solution of $FeCl_3$ (~3 mmol $FeCl_3.6H_2O$ in ~10 cm³ water, at ~5° C.) is added. The resulting mixture is held at ~5° C. for ~30 minutes with stirring. The resulting reaction product mixture contains the diaminophenothiazinium compound.

For example, in one embodiment, the reaction product mixture obtained by the deacylating (DAC) step and containing the deacylated product (~20 mmol) is cooled to ~5° C., and a cooled aqueous solution of $FeCl_3$ (~40 mmol $FeCl_3.6H_2O$ in ~80 cm³ water, at ~5° C.) is added. The resulting mixture is held at ~5° C. for ~30 minutes with stirring. The resulting reaction product mixture contains the diaminophenothiazinium compound.

Optional Additional Purification Steps

Each of the optional additional purification steps ($PUR^{RED-AC}$, $PUR^{DA-OX}$, $PUR^{OX}$, and $PUR^{AC2-CON}$), if present, may be performed using any suitable means of purification.

In one embodiment, one or more or all of the optional additional purification steps ($PUR^{RED-AC}$, $PUR^{DA-OX}$, $PUR^{OX}$, $PUR^{AC2-CON}$), if present, is as defined above under the heading "The Purification (PUR) Step."

In one embodiment, one or both of the optional additional purification steps $PUR^{RED-AC}$ and $PUR^{DA-OX}$, if present, is as defined above under the heading "The Purification (PUR) Step."

Optional Additional Purification: $PUR^{OX}$

In one embodiment, after said oxidizing (OX) step, said diaminophenothiazinium compound obtained in said oxidizing (OX) step is purified ($PUR^{OX}$).

In one embodiment, the purifying ($PUR^{OX}$) step is, or comprises, recrystallisation.

In one embodiment, the recrystallisation comprises adding the compound to a suitable solvent (e.g., water); heating the mixture to dissolve (preferably fully dissolve) the compound; cooling the heated mixture or allowing the heated mixture to cool so as to allow the compound to precipitate; and collection of the precipitate (e.g., by filtration).

In one embodiment, the recrystallisation includes a step of adjusting the pH of the mixture of compound and suitable solvent (e.g., water) to be about 0.5 to about 2.5 (e.g., about 1 to about 2), for example, using HCl. This additional step may be performed, for example, before cooling the heated mixture or allowing the heated mixture to cool, or, more preferably, before heating the mixture to dissolve the compound.

In one embodiment, the recrystallisation comprises adding the compound to a suitable solvent (e.g., water); adjusting the pH of the mixture to be about 0.5 to about 2.5 (e.g., about 1 to about 2) using HCl; heating the mixture to dissolve (preferably fully dissolve) the compound; cooling the heated mixture or allowing the heated mixture to cool so as to allow the compound to precipitate; and collection of the precipitate (e.g., by filtration).

Optionally, the recrystallisation further comprises the subsequent step of washing of the precipitate one or more (e.g., 1, 2, 3, 4) times, for example, with a suitable washing solvent, for example, the same solvent used to dissolve the compound.

Optionally, the recrystallisation further comprises, after collection of the precipitate and/or after washing of the precipitate, a step of drying the precipitate or washed precipitate, for example, drying in an oven and/or drying under vacuum.

For example, in one embodiment, the recrystallisation is performed by adding the compound (e.g., methylthioninium chloride) (~1 g, ~3 mmol) to water (~40 cm³), adjusting the pH of the mixture to be ~1.7 using aqueous hydrochloric acid (HCl, 5 M), heating the mixture to ~80° C. until all of the compound has dissolved, allowing the mixture to cool naturally to ~25° C. while stirring so as to allow the compound to precipitate, filtering the mixture to collect the precipitate, and drying in an oven at ~60° C. for ~18 hours.

For example, in one embodiment, the recrystallisation is performed by adding the compound (e.g., methylthioninium chloride) (~1 g, ~3 mmol) to water (~20 cm³), adjusting the pH of the mixture to be ~1 to ~2 using aqueous hydrochloric acid (HCl, 10 M, 0.33 cm³), heating the mixture to ~80° C. until all of the compound has dissolved, allowing the mixture to cool naturally to ~25° C. while stirring so as to allow the compound to precipitate, filtering the mixture to collect the precipitate, and drying in an oven at ~60° C. for ~18 hours.

Purity

The methods described herein yield diaminophenothiazinium compounds as defined herein and including, for example, methylthioninium chloride (MTC), at a purity that, until now, has been unavailable worldwide.

For example, many of the methods described herein yield very high purity MTC with extremely low levels of both organic impurities (e.g., of Azure B, Azure A, Azure C, and Methylene Violet Bernthsen (MVB)) and metal impurities (e.g., meeting or exceeding the European Pharmacopoeia (EP) limits).

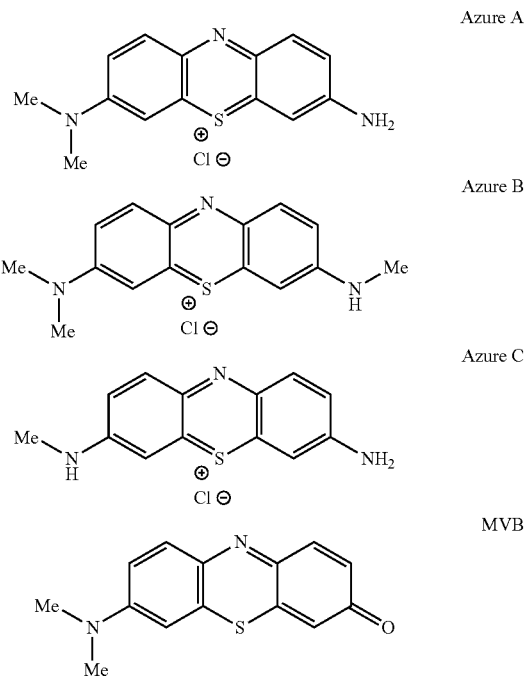

Azure A

Azure B

Azure C

MVB

Thus, one aspect of the present invention pertains to a diaminophenothiazinium compound as defined herein and including, for example, methylthioninium chloride (MTC), that has a purity as defined herein.

In one embodiment, the present invention pertains to methylthioninium chloride (MTC) that has a purity as defined herein.

Another aspect of the present invention pertains to a diaminophenothiazinium compound as defined herein and including, for example, methylthioninium chloride (MTC), that is obtained by, or is obtainable by, a method of synthesis and/or purification as described herein, and that has a purity as defined herein.

In one embodiment, the present invention pertains to methylthioninium chloride (MTC) that is obtained by, or is obtainable by, a method of synthesis and/or purification as described herein, and that has a purity as defined herein.

In one embodiment, the compound (e.g., MTC) has a purity of 99.7% or greater.

In one embodiment, the compound (e.g., MTC) has a purity of 99.6% or greater.

In one embodiment, the compound (e.g., MTC) has a purity of 99.5% or greater.

In one embodiment, the compound (e.g., MTC) has a purity of 99% or greater.

In one embodiment, the compound (e.g., MTC) has a purity of 98% or greater.

In one embodiment, the compound has less than 0.1% Azure B as impurity.

In one embodiment, the compound has less than 0.5% Azure B as impurity.

In one embodiment, the compound has less than 1% Azure B as impurity.

In one embodiment, the compound has less than 2% Azure B as impurity.

In one embodiment, the compound has less than 0.05% Azure A as impurity.

In one embodiment, the compound has less than 0.10% Azure A as impurity.

In one embodiment, the compound has less than 0.15% Azure A as impurity.

In one embodiment, the compound has less than 0.05% Azure C as impurity.

In one embodiment, the compound has less than 0.10% Azure C as impurity.

In one embodiment, the compound has less than 0.15% Azure C as impurity.

In one embodiment, the compound has less than 0.02% MVB as impurity.

In one embodiment, the compound has less than 0.05% MVB as impurity.

(All Percentage Purities Recited Herein are Weight/Weight Unless Otherwise Specified.)

In one embodiment, the compound (e.g., MTC) has an elementals purity (e.g., for each of Al, Cr, Zn, Cu, Fe, Mn, Hg, Ni, Mo, Cd, Sn, and Pb) that is equal to or better than the values mentioned in column "Version EP4" in Table 1 below (believed to be the European Pharmacopoeia (EP) limits for Version EP4 set in 2002).

In one embodiment, the compound (e.g., MTC) has an elementals purity (e.g., for each of Al, Cr, Zn, Cu, Fe, Mn, Hg, Ni, Mo, Cd, Sn, and Pb) that is equal to or better than the values mentioned in column "Version EP5.4" in Table 1 below (believed to be the European Pharmacopoeia (EP) limits for Version EP5.4 set in 2006).

The term "elementals purity" referred to herein pertains to the amounts of the twelve (12) metals specified by the European Pharmacopoeia: Al, Cr, Zn, Cu, Fe, Mn, Hg, Ni, Mo, Cd, Sn, and Pb.

TABLE 1

| Element | Elementals Purity ($\mu$g/g) | |
|---|---|---|
| | Version EP4 | Version EP5.4 |
| Aluminium (Al) | 100 | 100 |
| Cadmium (Cd) | 1 | 1 |
| Chromium (Cr) | 10 | 100 |
| Copper (Cu) | 100 | 300 |
| Tin (Sn) | 10 | 10 |
| Iron (Fe) | 100 | 200 |
| Manganese (Mn) | 10 | 10 |
| Mercury (Hg) | 1 | 1 |
| Molybdenum (Mo) | 10 | 10 |
| Nickel (Ni) | 10 | 10 |
| Lead (Pb) | 10 | 10 |
| Zinc (Zn) | 10 | 100 |

In one embodiment, the compound (e.g., MTC) has an elementals purity that is equal to or better than 0.9 times the values quoted for "Version EP4" in Table 1.

In one embodiment, the compound (e.g., MTC) has an elementals purity that is equal to or better than 0.9 times the values quoted for "Version EP5.4" in Table 1.

In one embodiment, the compound (e.g., MTC) has an elementals purity that is equal to or better than 0.8 times the values quoted for "Version EP4" in Table 1.

In one embodiment, the compound (e.g., MTC) has an elementals purity that is equal to or better than 0.8 times the values quoted for "Version EP5.4" in Table 1.

In one embodiment, the compound (e.g., MTC) has an elementals purity that is equal to or better than 0.7 times the values quoted for "Version EP4" in Table 1.

In one embodiment, the compound (e.g., MTC) has an elementals purity that is equal to or better than 0.7 times the values quoted for "Version EP5.4" in Table 1.

In one embodiment, the compound (e.g., MTC) has an elementals purity that is equal to or better than 0.5 times the values quoted for "Version EP4" in Table 1.

In one embodiment, the compound (e.g., MTC) has an elementals purity that is equal to or better than 0.5 times the values quoted for "Version EP5.4" in Table 1.

(For example, 0.5 times the values quoted for "Version EP4" in Table 1 are 50 $\mu$g/g Al, 0.5 $\mu$g/g Cd, 5 $\mu$g/g Cr, etc.)

In one embodiment, the compound (e.g., MTC) has a chromium purity that is equal to or better than 10 $\mu$g/g.

In one embodiment, the compound (e.g., MTC) has a chromium purity that is equal to or better than 100 $\mu$g/g.

In one embodiment, the compound (e.g., MTC) has a copper purity that is equal to or better than 10 $\mu$g/g.

In one embodiment, the compound (e.g., MTC) has an iron purity that is equal to or better than 100 $\mu$g/g.

All plausible and compatible combinations of the above purity grades are disclosed herein as if each individual combination was specifically and explicitly recited.

Compositions

One aspect of the present invention pertains to a composition comprising a diaminophenothiazinium compound, as defined herein and including, for example, methylthioninium chloride (MTC), that is obtained by, or is obtainable by, a method of synthesis and/or purification as described herein, and/or that has a purity as defined herein.

One aspect of the present invention pertains to a composition comprising a diaminophenothiazinium compound, as defined herein and including, for example, methylthioninium chloride (MTC), that is obtained by, or is obtainable by, a method of synthesis and/or purification as described herein.

One aspect of the present invention pertains to a composition comprising a diaminophenothiazinium compound, as defined herein and including, for example, methylthioninium chloride (MTC), that has a purity as defined herein.

One aspect of the present invention pertains to a composition comprising a diaminophenothiazinium compound, as defined herein and including, for example, methylthioninium chloride (MTC), that is obtained by, or is obtainable by, a method of synthesis and/or purification as described herein, and that has a purity as defined herein.

In one embodiment, the composition is a pharmaceutical composition.

In one embodiment, the pharmaceutical composition further comprises a pharmaceutically acceptable carrier, diluent, or excipient.

Compositions and formulations are discussed in more detail below.

Methods of Inactivating Pathogens

One aspect of the present invention pertains to the use of a diaminophenothiazinium compound, as defined herein and including, for example, methylthioninium chloride (MTC), that is obtained by, or is obtainable by, a method of synthesis and/or purification as described herein, and/or that has a purity as defined herein, in a method of inactivating a pathogen in a sample (for example a blood or plasma sample), for example, in vitro, the method comprising the steps of introducing the compound into the sample, and subsequently exposing the sample to light.

Another aspect of the present invention pertains to a method of inactivating a pathogen in a sample, for example, in vitro, comprising the steps of introducing an effective amount of a compound into the sample, and subsequently exposing the sample to light, wherein the compound is a diaminophenothiazinium compound, as defined herein and including, for example, methylthioninium chloride (MTC), that is obtained by, or is obtainable by, a method of synthesis and/or purification as described herein, and/or that has a purity as defined herein.

Use in Methods of Medical Treatment

One aspect of the present invention pertains to a diaminophenothiazinium compound, as defined herein and including, for example, methylthioninium chloride (MTC), that is obtained by, or is obtainable by, a method of synthesis and/or purification as described herein, and/or that has a purity as defined herein, for use in a method of treatment (e.g., a method of treatment or prophylaxis, e.g., a method of treatment or prophylaxis of a disease condition, as described herein) of the human or animal body by therapy.

One aspect of the present invention pertains to a diaminophenothiazinium compound, as defined herein and including, for example, methylthioninium chloride (MTC), that is obtained by, or is obtainable by, a method of synthesis and/or purification as described herein, for use in a method of treatment (e.g., a method of treatment or prophylaxis of a disease condition, as described herein) of the human or animal body by therapy.

One aspect of the present invention pertains to a diaminophenothiazinium compound, as defined herein and including, for example, methylthioninium chloride (MTC), that has a purity as defined herein, for use in a method of treatment (e.g., a method of treatment or prophylaxis of a disease condition, as described herein) of the human or animal body by therapy.

One aspect of the present invention pertains to a diaminophenothiazinium compound, as defined herein and including, for example, methylthioninium chloride (MTC), that is obtained by, or is obtainable by, a method of synthesis and/or purification as described herein, and that has a purity as defined herein, for use in a method of treatment (e.g., a method of treatment or prophylaxis of a disease condition, as described herein) of the human or animal body by therapy.

Use in the Manufacture of Medicaments

One aspect of the present invention pertains to the use of a diaminophenothiazinium compound, as defined herein and including, for example, methylthioninium chloride (MTC), that is obtained by, or is obtainable by, a method of synthesis and/or purification as described herein, and/or that has a purity as defined herein, in the manufacture of a medicament for use in the treatment or prophylaxis of a disease condition, as described herein.

One aspect of the present invention pertains to the use of a diaminophenothiazinium compound, as defined herein and including, for example, methylthioninium chloride (MTC), that is obtained by, or is obtainable by, a method of synthesis and/or purification as described herein, in the manufacture of a medicament for use in the treatment or prophylaxis of a disease condition, as described herein.

One aspect of the present invention pertains to the use of a diaminophenothiazinium compound, as defined herein and including, for example, methylthioninium chloride (MTC), that is obtained by, or is obtainable by, a method of synthesis and/or purification as described herein, and that has a purity as defined herein, in the manufacture of a medicament for use in the treatment or prophylaxis of a disease condition, as described herein.

Methods of Treatment

One aspect of the present invention pertains to a method of treatment or prophylaxis of a disease condition, as described herein, in a patient, comprising administering to said patient a therapeutically-effective amount or a prophylactically-effective amount of a diaminophenothiazinium compound, as defined herein and including, for example, methylthioninium chloride (MTC), that is obtained by, or is obtainable by, a method of synthesis and/or purification as described herein, and/or that has a purity as defined herein.

One aspect of the present invention pertains to a method of treatment or prophylaxis of a disease condition, as described herein, in a patient, comprising administering to said patient a therapeutically-effective amount or a prophylactically-effective amount of a diaminophenothiazinium compound, as defined herein and including, for example, methylthioninium chloride (MTC), that is obtained by, or is obtainable by, a method of synthesis and/or purification as described herein.

One aspect of the present invention pertains to a method of treatment or prophylaxis of a disease condition, as described herein, in a patient, comprising administering to said patient a therapeutically-effective amount or a prophylactically-effective amount of a diaminophenothiazinium compound, as defined herein and including, for example, methylthioninium chloride (MTC), that has a purity as defined herein.

One aspect of the present invention pertains to a method of treatment or prophylaxis of a disease condition, as described herein, in a patient, comprising administering to said patient a therapeutically-effective amount or a prophylactically-effective amount of a diaminophenothiazinium compound, as defined herein and including, for example, methylthioninium chloride (MTC), that is obtained by, or is obtainable by, a method of synthesis and/or purification as described herein, and that has a purity as defined herein.

One aspect of the present invention pertains to a method of regulating the aggregation of a tau protein in the brain of a mammal, which aggregation is associated with a disease statem as described herein, the treatment comprising administering to said mammal in need of said treatment, a prophylactically- or therapeutically-effective amount of an inhibitor of said aggregation, wherein the inhibitor is a diaminophenothiazinium compound, as defined herein and including, for example, methylthioninium chloride (MTC), that is obtained by, or is obtainable by, a method of synthesis and/or purification as described herein, and that has a purity as defined herein.

Disease Conditions

In one embodiment, the disease condition is a tauopathy.

In one embodiment, the disease condition is a disease of tau protein aggregation.

Diseases which are characterized primarily or partially by abnormal tau aggregation are referred to herein as "tauopathies" or "diseases of tau protein aggregation." Examples of such diseases are discussed in the article by Wischik et al. in *Neurobiology of Alzheimer's Disease*, 2nd Edition, 2000, Eds. Dawbarn, D. and Allen, S. J., The Molecular and Cellular Neurobiology Series, Bios Scientific Publishers, Oxford, UK.

In one embodiment, the disease condition is Alzheimer's disease (AD); Pick's disease; Progressive Supranuclear Palsy (PSP); fronto-temporal dementia (FTD); FTD and parkinsonism linked to chromosome 17 (FTDP-17); disinhibition-dementia-parkinsonism-amyotrophy complex (DDPAC);

pallido-ponto-nigral degeneration (PPND); Guam-ALS syndrome; pallido-nigro-luysian degeneration (PNLD); or cortico-basal degeneration (CBD).

In one embodiment, the disease condition is Alzheimer's disease (AD).

In one embodiment, the disease is a disease of tau protein aggregation, as described herein, and the effective amount is an amount sufficient to inhibit the aggregation of the tau protein associated with said disease state.

In one embodiment, the disease condition is mild cognitive impairment (MCI).

In one embodiment, the disease condition is skin cancer.

In one embodiment, the disease condition is melanoma.

In one embodiment, the disease condition is methemoglobinemia.

In one embodiment, the disease condition is a viral, bacterial, protozoal, or parasitic disease condition (e.g., a viral infection, a bacterial infection, a protozoal infection, a paraisitic infection).

In one embodiment, the disease condition is a viral infection.

In one embodiment, the disease condition is a bacterial infection.

In one embodiment, the disease condition is a protozoal infection.

In one embodiment, the disease condition is a parasitic infection.

In one embodiment, the disease condition is parasitic infection with a parasite of Trypanosoma, Leishmania, Eimeria, Neospora, Cyclospora, or Cryptosporidia family.

In one embodiment, the disease condition is infection with *Plasmodium vivax, Plasmodium falciparum, Plasmodium malariae, Plasmodium ovale, Trypanosoma protoza, Entamoeba histolytica, Trichomonas vaginalis, Giardia larnblia, Trypanosoma brucei gambiense, Trypanosoma brucei rhodesiense, Trypanosoma cruzi, Leishmania major, Leishmania tropica, Leishmania aethiopica, Leishmania infantum, Leishmania braiiliensis, Leishmania mexicana, Leishmania arnazonensis, Leishmania donovani-Leishmania infantum* complex, *Cryptosporidium parvum, Toxoplasma gondii, Encephalitozoon* species, *Nosema* species, or *Septata intestinalis*.

In one embodiment, the disease condition is malaria, visceral leishmaniasis (often known as kalaazar), African sleeping sickness, toxoplasmosis, giardiasis, or Chagas' disease.

In one embodiment, the disease condition is malaria (i.e., an example of a protozoal disease condition).

In this embodiment (i.e., the disease condition is malaria), the treatment may be in combination with one or more other antimicrobial agents, for example, one or more of chloroquine, atovaquone, quinine, primethamine, sulfadiazine, and primaquine.

In one embodiment, the disease condition is, or is caused by, Hepatitis C virus (HCV), human immunodeficiency virus (HIV), or West Nile virus (WNV).

In one embodiment, the disease condition is Hepatitis C virus (HCV) infection.

In one embodiment, the disease condition is human immunodeficiency virus (HIV) infection.

In one embodiment, the disease condition is West Nile virus (WNV) infection.

In one embodiment, the disease condition is a synucleinopathy.

As those skilled in the art will be aware, the term synucleinopathies is used to name a group of neurodegenerative disorders characterized by fibrillary aggregates of synuclein protein, particularly α-synuclein, in the cytoplasm of selective populations of neurons and glia, and in particular in which the presence of synuclein-containing inclusions are pathognomic for the disease. This should be distinguished from non-synucleinopathy disorders in which synuclein-containing inclusions may or may not be present in addition to other pathologies.

The synucleinopathies currently consist of the following disorders: Parkinson's disease (PD), dementia with Lewy bodies (DLB), multiple system atrophy (MSA), drug-induced parkinsonism (e.g. produced by 1-methyl-4-phenyl-1,2,3,6-tetrahydropyridine (MPTP) or pesticides such as rotenone), and pure autonomic failure (PAF).

In one embodiment, the disease condition is Parkinson's disease (PD).

In one embodiment, the disease condition is dementia with Lewy bodies (DLB).

In one embodiment, the disease condition is multiple system atrophy (MSA).

In one embodiment, the disease condition is drug-induced parkinsonism.

In one embodiment, the disease condition is pure autonomic failure (PAF).

Treatment

The term "treatment," as used herein in the context of treating a disease condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

The diaminophenothiazinium compound, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Suitable subjects for the methods involving Alzheimer's disease may be selected on the basis of conventional factors. Thus, the initial selection of a patient may involve any one or more of: rigorous evaluation by an experienced clinician; exclusion of non-Alzheimer's disease diagnosis as far as possible by supplementary laboratory and other investigations; and objective evaluation of level of cognitive function using neuropathologically validated battery.

In one embodiment, the subject/patient is not a human.

Formulations

While it is possible for the diaminophenothiazinium compound to be used (e.g., administered) alone, it is often preferable to present it as a composition or formulation.

In one embodiment, the composition is a pharmaceutical composition (e.g., formulation, preparation, medicament) comprising a diaminophenothiazinium compound, as described herein, and a pharmaceutically acceptable carrier, diluent, or excipient.

In one embodiment, the composition is a pharmaceutical composition comprising at least one diaminophenothiazinium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, New York, USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one diaminophenothiazinium compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Preferred Formulations

One aspect of the present invention pertains to a dosage unit (e.g., a pharmaceutical tablet or capsule) comprising 20 to 300 mg of a diaminophenothiazinium compound, as defined herein and including, for example, methylthioninium chloride (MTC), that is obtained by, or is obtainable by, a method as described herein, and/or that has a purity as defined herein, and a pharmaceutically acceptable carrier, diluent, or excipient.

One aspect of the present invention pertains to a dosage unit (e.g., a pharmaceutical tablet or capsule) comprising 20 to 300 mg of a diaminophenothiazinium compound, as defined herein and including, for example, methylthioninium chloride (MTC), that is obtained by, or is obtainable by, a method as described herein, and/or that has a purity as defined herein.

In one embodiment, the dosage unit is a tablet.
In one embodiment, the dosage unit is a capsule.
In one embodiment, the amount is 30 to 200 mg.
In one embodiment, the amount is about 25 mg.
In one embodiment, the amount is about 30 mg.
In one embodiment, the amount is about 35 mg.
In one embodiment, the amount is about 50 mg.
In one embodiment, the amount is about 60 mg.
In one embodiment, the amount is about 70 mg.
In one embodiment, the amount is about 100 mg.
In one embodiment, the amount is about 125 mg.
In one embodiment, the amount is about 150 mg.
In one embodiment, the amount is about 175 mg.
In one embodiment, the amount is about 200 mg.
In one embodiment, the amount is about 250 mg.

In one embodiment, the dosage unit further comprises a pharmaceutically acceptable carrier, diluent, or excipient.

In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Dosage

It will be appreciated by one of skill in the art that appropriate dosages of the diaminophenothiazinium compound, and compositions comprising the diaminophenothiazinium compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the diaminophenothiazinium compound is in the range of about 100 ng to about 25 mg (more typically about 1 to 10 mg) per kilogram body weight of the subject per day. Where the diaminophenothiazinium compound is a salt, an ester, an amide, a prodrug, or the like, the amount administered is calculated on the basis of the parent compound and so the actual weight to be used is increased proportionately.

In one embodiment, the diaminophenothiazinium compound (e.g., MTC) is administered to a human patient according to one of the following dosage regimes:

about 50 mg, 3 times daily;
about 50 mg, 4 times daily;
about 75 mg, 3 times daily;
about 75 mg, 4 times daily;
about 100 mg, 2 times daily;
about 100 mg, 3 times daily;
about 125 mg, 2 times daily;
about 125 mg, 3 times daily;
about 150 mg, 2 times daily;
about 200 mg, 2 times daily.

Combination Treatments and Therapies

Any of the medical uses or methods described herein may be used as part of a combination treatment or therapy, that is, a treatment or therapy in which two or more treatments or therapies are combined, for example, sequentially or simultaneously.

In one embodiment, a treatment (e.g., employing a diaminophenothiazinium compound as described herein) is in combination with one or more other antimicrobial agents, for example, chloroquine and atovaquone.

In one embodiment, a treatment (e.g., employing a diaminophenothiazinium compound as described herein) is in combination with a cholinesterase inhibitor such as Donepezil (Aricept™), Rivastigmine (Exelon™) or Galantamine (Reminyl™)

In one embodiment, a treatment (e.g., employing a diaminophenothiazinium compound as described herein) is in combination with an NMDA receptor antagonist such as Memantine (Ebixa™, Namenda™)

In one embodiment, a treatment (e.g. employing a diaminophenothiazinium compound as described herein) is in combination with a muscarinic receptor agonist.

In one embodiment, a treatment (e.g. employing a diaminophenothiazinium compound as described herein) is in combination with an inhibitor of amyloid precursor protein processing that leads to enhanced generation of beta-amyloid.

Kits

One aspect of the invention pertains to a kit comprising (a) a diaminophenothiazinium compound as described herein, or a composition comprising an diaminophenothiazinium compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

For example, in one embodiment, the kit is a drug product for the treatment of a disease in a mammal suffering therefrom, comprising a container labelled or accompanied by a label indicating that the drug product is for the treatment of said disease, the container containing one or more dosage units each comprising at least one pharmaceutically acceptable excipient and, as an active ingredient, a diaminophenothiazinium compound as described herein.

Ligands and Labels

The diaminophenothiazinium compounds discussed herein and that are capable of inhibiting the aggregation of tau protein will also be capable of acting as ligands or labels of tau protein (or aggregated tau protein). Thus, in one embodiment, the diaminophenothiazinium compound is a ligand of tau protein (or aggregated tau protein).

Such diaminophenothiazinium compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic or therapeutic application.

For example, in one embodiment, the diaminophenothiazinium compound is as defined above, but with the additional limitation that the compound incorporates, is conjugated to, is chelated with, or is otherwise associated with one or more (e.g., 1, 2, 3, 4, etc.) isotopes, radioisotopes, positron-emitting atoms, magnetic resonance labels, dyes, fluorescent markers, antigenic groups, or therapeutic moieties.

In one embodiment, the diaminophenothiazinium compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in one embodiment, the diaminophenothiazinium compound is as defined above, but with the additional limitation that the compound incorporates, is conjugated to, is chelated with, or is otherwise associated with, one or more (e.g., 1, 2, 3, 4, etc.) detectable labels.

Labelled diaminophenothiazinium compounds (e.g., when ligated to tau protein or aggregated tau protein) may be visualised or detected by any suitable means, and the skilled person will appreciate that any suitable detection means as is known in the art may be used.

For example, the diaminophenothiazinium compound (ligand-label) may be suitably detected by incorporating a positron-emitting atom (e.g., $^{11}$C) (e.g., as a carbon atom of one or more alkyl group substituents, e.g., methyl group substituents) and detecting the compound using positron emission tomography (PET) as is known in the art. Suitable methods for preparing these and similar $^{11}$C labelled diaminophenothiaziniums are shown, for example, in Wischik, C. M., et al., 2002b (see especially FIGS. 11a, 11b, 12 therein) and Schweiger, L. F., et al., 2005.

One aspect of the present invention pertains to a method of labelling tau protein (or aggregated tau protein) comprising the steps of: contacting the tau protein (or aggregated tau protein) with a diaminophenothiazinium compound, as described herein, that additionally incorporates, is conjugated to, is chelated with, or is otherwise associated with, one or more (e.g., 1, 2, 3, 4, etc.) detectable labels.

Another aspect of the present invention pertains to a method of detecting tau protein (or aggregated tau protein) comprising the steps of:

(i) contacting the tau protein (or aggregated tau protein) with a diaminophenothiazinium compound, as described herein, and that additionally incorporates, is conjugated to, is chelated with, or is otherwise associated with, one or more (e.g., 1, 2, 3, 4, etc.) detectable labels, and (ii) detecting the presence and/or amount of said compound bound to tau protein (or aggregated tau protein).

Another aspect of the present invention pertains to a method of diagnosis or prognosis of a tauopathy in a subject believed to suffer from the disease, comprising the steps of:

(i) introducing into the subject a diaminophenothiazinium compound capable of labelling tau protein or aggregated tau protein, particularly tau protein (e.g., a diaminophenothiazinium compound, as described herein, and that additionally incorporates, is conjugated to, is chelated with, or is otherwise associated with, one or more (e.g., 1, 2, 3, 4, etc.) detectable labels), (ii) determining the presence and/or amount of said compound bound to tau protein or aggregated tau protein in the brain of the subject, and (iii) correlating the result of the determination made in (ii) with the disease state of the subject.

Another aspect of the present invention pertains to a diaminophenothiazinium compound capable of labelling tau protein or aggregated tau protein (e.g., a diaminophenothiazinium compound, as described herein, and that additionally incorporates, is conjugated to, is chelated with, or is otherwise associated with, one or more (e.g., 1, 2, 3, 4, etc.) detectable labels), for use in a method of diagnosis or prognosis of a tauopathy.

In another aspect, the present invention provides use of a diaminophenothiazinium compound capable of labelling tau protein or aggregated tau protein, particularly tau protein (e.g., a diaminophenothiazinium compound, as described herein, that additionally incorporates, is conjugated to, is chelated with, or is otherwise associated with, one or more (e.g., 1, 2, 3, 4, etc.) detectable labels), in a method of manufacture of a diagnostic or prognostic reagent for use in the diagnosis or prognosis of a tauopathy.

The diaminophenothiazinium ligands/labels may be administered directly, or they may be administered in a precursor form, for conversion to the active form (e.g., ligating form, labelling form) by an activating agent present in, or administered to, the same subject.

The diaminophenothiazinium ligands/labels may be used as part of a method of diagnosis or prognosis. They may be used to select a patient for treatment, or to assess the effectiveness of a treatment or a therapeutic agent (e.g. an inhibitor of tau protein aggregation) administered to the subject.

EXAMPLES

The following examples are provided solely to illustrate the present invention and are not intended to limit the scope of the invention, as described herein.

Synthesis 1

3,7-Dimethylamino-10H-phenothiazine

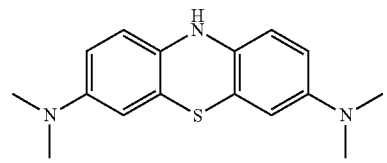

To a 250 cm$^3$ round bottom flask placed under an atmosphere of argon was added methylthioninium chloride (Medex™) (MTC.3H$_2$O, MW 373.90, 10 g, 26.7 mmol) and ethanol (75 cm$^3$). Sodium borohydride (NaBH$_4$, MW 37.83, 2.0 g, 52.9 mmol) was added in portions. The mixture was heated to 40° C. and stirred for 1 hour. The resulting yellow/green suspension was cooled to 5° C. using an ice-water bath and filtered by canular under argon, washed once with ethanol (20 cm$^3$), and dried under vacuum at room temperature to give the title compound as a light green solid. The product was used without further purification in Synthesis 2.

Synthesis 2

3,7-Dimethylamino-10-acetyl-phenothiazine

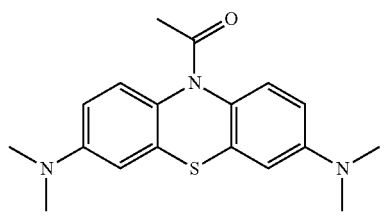

The 3,7-dimethylamino-10H-phenothiazine obtained in Synthesis 1 was placed in a 250 cm$^3$ round bottom flask and acetic anhydride (($H_3CCO)_2O$, 40 cm$^3$) and pyridine (10 cm$^3$) were added, and the resulting solution was heated at 120° C. for 18 hours with stirring. The reaction mixture was cooled to room temperature and then poured carefully into ice-water while stirring to give a light brown solid, which was filtered using a standard Buchner funnel apparatus with a water aspirator, washed once with water (100 cm$^3$), and dried in an oven at 60° C. for 3 hours to yield the title compound (MW 327.45, 4.63 g, 14.1 mmol, yield 53%), which was recrystallised from ethanol by dissolving it in hot ethanol (100 cm$^3$), adding activated charcoal (1 g), filtering to remove the charcoal, cooling the solution to 5° C. using an ice-water bath so that a precipitate formed (colourless crystals), and filtering using a standard Buchner filter with a water aspirator in order to collect the crystals. The crystals where then dried in an oven at 60° C. for 3 hours.

$\delta_H$ (250 MHz; CDCl$_3$): 2.16 (3H, s, CH$_3$), 2.93 (12H, s, NCH$_3$), 6.59-6.62 (2H, d, J 8.5, ArH), 6.69-6.71 (2H, d, J 2.7 5, ArH); 7.08-7.47 (2H, brd s, ArH); $\delta_C$ (62.9 MHz; CDCl$_3$): 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+H]$^+$), 350.1 (41%, [M+Na]$^+$).

Synthesis 3

Methylthioninium Chloride (MTC)

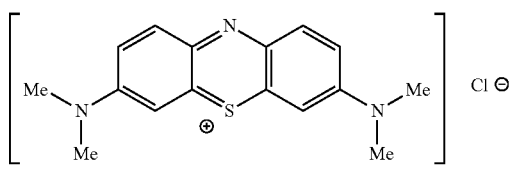

3,7-Dimethylamino-10-acetyl-phenothiazine obtained in the Synthesis 2 (MW 327.45, 1 g, 3.05 mmol) was placed in a 50 cm$^3$ round bottom flask, and water (10 cm$^3$) and hydrochloric acid (10 M, 3 cm$^3$) were added, and the resulting solution was heated at 80° C. for 1 hour with stirring to give a green solution. The reaction mixture was cooled to 5° C. using an ice-water bath, and cooled aqueous iron chloride hexahydrate (FeCl$_3$.6H$_2$O, MW 270.30, 0.82 g, 3.03 mmol, 10 cm$^3$) was added, giving an immediate deep blue colour. (The aqueous iron chloride hexahydrate was prepared by dissolving the solid iron chloride hexahydrate in water (10 cm$^3$) and cooling to 5° C. using an ice-water bath before being added to the reaction mixture.) The reaction mixture was stirred for a further 30 minutes at 5° C., filtered using a standard Buchner filter with a water aspirator, and dried in an oven at 60° C. for 18 hours to give the title compound (MW 319.86, 0.51 g, 1.59 mmol, yield 52%) as green needles.

$\delta_H$ (250 MHz; D$_2$O): 6.99 (2H, d, 9.25, ArH), 6.82 (2H, d, 8, ArH), 6.58 (2H, s, ArH), 2.98 (12H, s, NCH$_3$).

Synthesis 4

Methylthioninium Chloride (MTC)

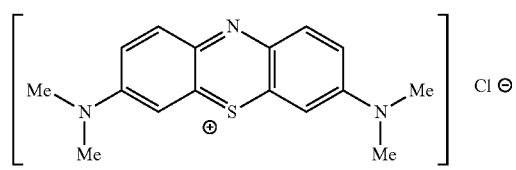

The product was prepared as described in Synthesis 3, except that the reaction mixture was cooled to 25° C. (instead of 5° C.) before the iron chloride hexahydrate was added.

Figure 2:
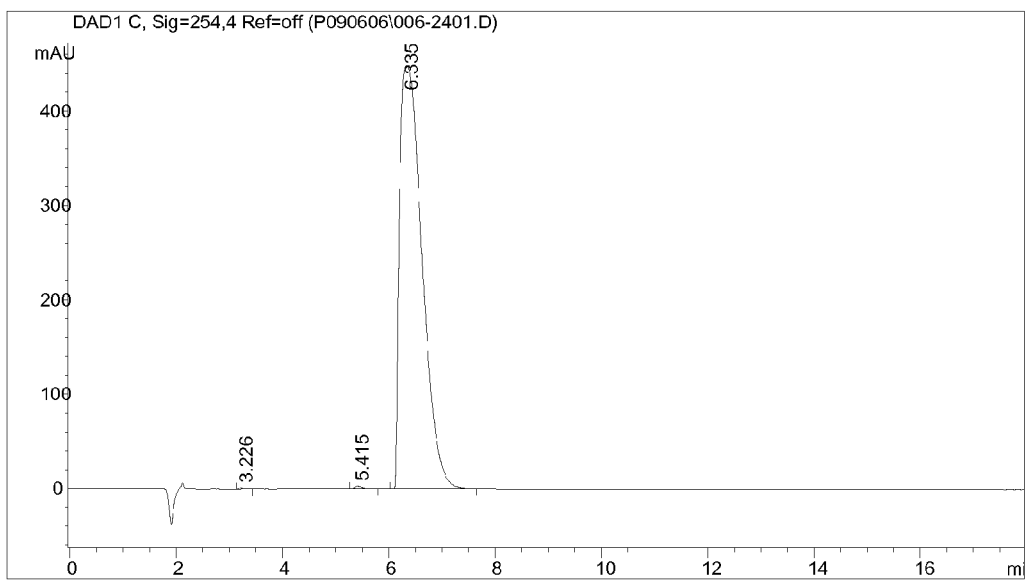
FIG. 2 is an HPLC chromatogram for high purity MTC-5° C. product obtained in Synthesis 4. Peaks at the following retention times were observed: 3.226, 5.415, and 6.335 minutes.

Samples of the Medex™ starting material and the products of Synthesis 3 (MTC-5° C.) and Synthesis 4 (MTC-25° C.) were compared using HPLC. Chromatograms for the Medex™ starting material and MTC-5° C. are shown in FIG. 1 and FIG. 2 respectively. The impurity levels are summarized in the following Table. Azure A, Azure, B, Azure C, and MVB (Methylene Violet Bernthsen) are common undesirable impurities typically found in samples of MTC.

TABLE 2

| Sample | MTC w/w % | Azure B w/w % | Azure A w/w % | Azure C w/w % | MVB w/w % | Other w/w % |
|---|---|---|---|---|---|---|
| Medex™ | 93.76 | 5.46 | 0.18 | 0.23 | 0.09 | 0.28 |
| MTC-25° C. | 98.98 | 0.92 | 0 | 0 | 0 | 0.10 |
| MTC-5° C. | 99.65 | 0.27 | 0 | 0 | 0 | 0.08 |

Synthesis 5

Methylthioninium Chloride (MTC)

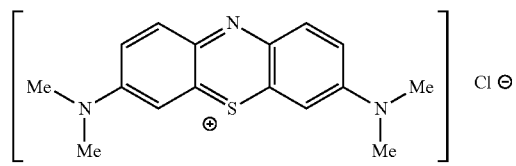

3,7-Dimethylamino-10-acetyl-phenothiazine obtained in Synthesis 2 (MW 327.45, 2.5 g, 7.63 mmol) was placed in a 50 cm$^3$ round bottom flask, and water (25 cm$^3$) and hydrochloric acid (10 M, 7.5 cm$^3$) were added, and the resulting solution was heated at 80° C. for 1 hour with stirring to give a green solution. The reaction mixture was cooled to 5° C. using an ice-water bath, and a cooled aqueous iron chloride hexahydrate solution (FeCl$_3$.$_6$H$_2$O, MW 270.30, 2.06 g, 7.62 mmol, 20 cm$^3$) was added, giving an immediate deep blue colour. (The aqueous iron chloride hexahydrate was prepared by dissolving the solid iron chloride hexahydrate in water (10 cm³) and cooling to 5° C. using an ice-water bath before being added to the reaction mixture.) The reaction mixture was stirred for a further 30 minutes at 5° C., filtered using a standard Buchner filter with a water aspirator, and dried in an oven at 60° C. for 18 hours to give the title compound (MW 319.86, 1.32 g, 4.12 mmol, 54%) as green needles. This material was recrystallised as described in the next synthesis.

Synthesis 6

Methylthioninium Chloride (MTC)

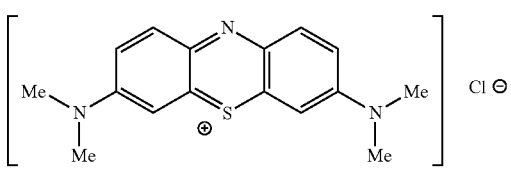

The product of Synthesis 5 was recrystallised by dissolving 1 g in water (40 cm³) and the pH was adjusted to 1.7 with 5 M aqueous hydrochloric acid (HCl). The suspension was then heated to 80° C. and allowed to cool to 25° C. naturally while stirring to give the highly pure title compound as fine green needles, which were dried in an oven at 60° C. for 18 hours (0.90 g, 90%).

$\delta_H$ (250 MHz; $D_2O$): 7.16 (2H, d, 9, ArH), 6.97 (2H, d, 9, ArH), 6.72 (2H, s, ArH), 3.08 (12H, s, $NCH_3$).

Figure 3:
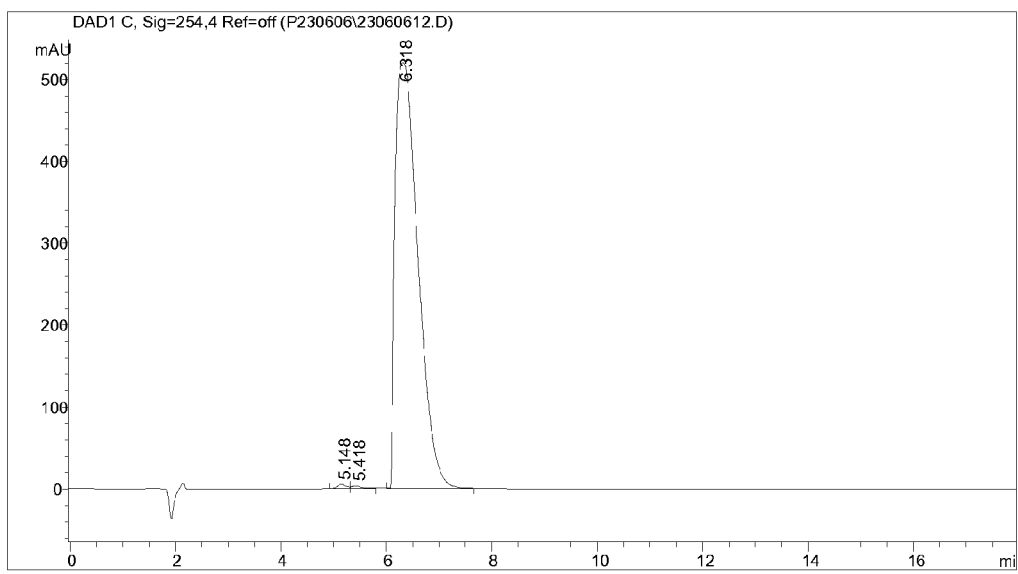
FIG. 3 is an HPLC chromatogram for the high purity MTC-5° C. crude product obtained in Synthesis 5. Peaks at the following retention times were observed: 5.148, 5.418, and 6.318 minutes.
Figure 4:
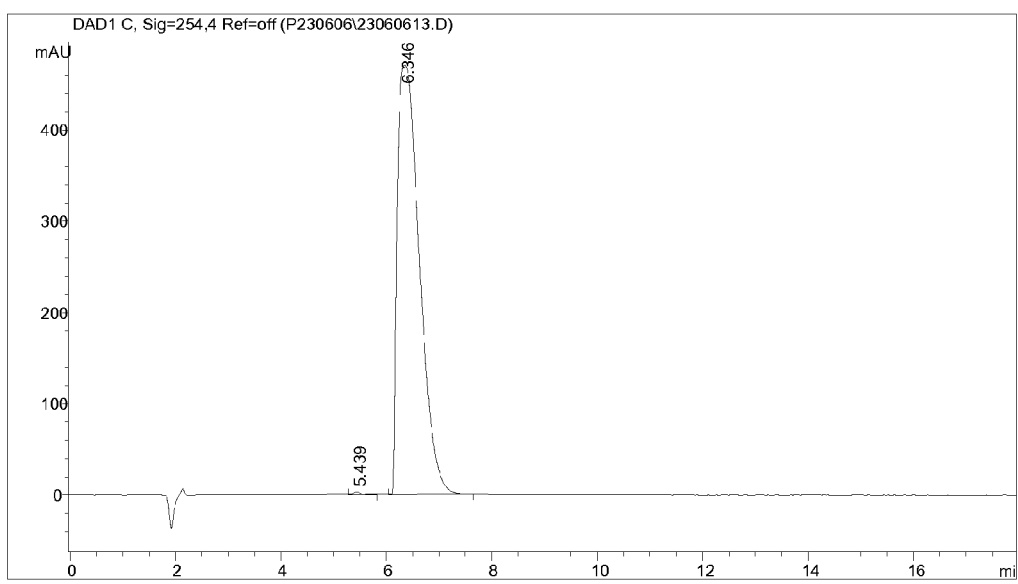
FIG. 4 is an HPLC chromatogram for high purity MTC-5° C.-recrystallised product obtained in Synthesis 6. Peaks at the following retention times were observed: 5.439 and 6.346 minutes.

Samples of the Medex™ starting material and the products of Synthesis 5 (MTC-5° C.-crude) and Synthesis 6 (MTC-5° C.-recrystallised) were compared using HPLC. Chromatograms for the MTC-5° C.-crude and MTC-5° C.-recrystallised are shown in FIG. 3 and FIG. 4, respectively. The impurity levels are summarized in the following Table. Azure A, Azure, B, Azure C, and MVB (Methylene Violet Bernthsen) are common undesirable impurities typically found in samples of MTC.

TABLE 3

| Sample | MTC w/w % | Azure B w/w % | Azure A w/w % | Azure C w/w % | MVB w/w % | Other w/w % |
|---|---|---|---|---|---|---|
| Medex ™ | 93.76 | 5.46 | 0.18 | 0.23 | 0.09 | 0.28 |
| MTC-5° C. (crude) | 99.35 | 0.31 | 0 | 0 | 0 | 0.34 |
| MTC-5° C. (recrystallised) | 99.73 | 0.27 | 0 | 0 | 0 | 0 |

Samples of the Medex™ starting material and the products of Synthesis 5 (MTC-5° C.-crude) and Synthesis 6 (MTC-5° C.-recrystallised) were analysed for metal content using ion-coupled plasma mass spectrometry (ICPMS). The metal contents are compared with the current European Pharmacopoeia (EP) limits in the following Table.

TABLE 4

| Element | EP Limits (µg/g) (Version EP5.4) | Medex ™ | MTC-5° C. (crude) | MTC-5° C. (recrystallised) |
|---|---|---|---|---|
| Aluminium (Al) | 100 | 8.0 | 8.3 | 2.1 |
| Cadmium (Cd) | 1 | <0.12 | <0.04 | <0.04 |
| Chromium (Cr) | 100 | 125 (*) | 3.7 | <0.76 |
| Copper (Cu) | 300 | 269 | 1.6 | <0.69 |
| Tin (Sn) | 10 | <0.90 | 1.0 (*) | 0.7 |
| Iron (Fe) | 200 | 92.2 | 687 (*) | 18.9 |
| Manganese (Mn) | 10 | <0.17 | 4.9 | 0.3 |
| Molybdenum (Mo) | 10 | <0.47 | 0.5 | 0.3 |
| Nickel (Ni) | 10 | <0.65 | <0.51 | <0.51 |
| Lead (Pb) | 10 | 1.0 | 0.3 | 0.4 |
| Zinc (Zn) | 100 | <1.25 | 10.5 (*) | 6.9 |

(*) denotes a failure to meet the European Pharmacopoeia (EP) limits.

Synthesis 7

3,7-Dimethylamino-10H-phenothiazine

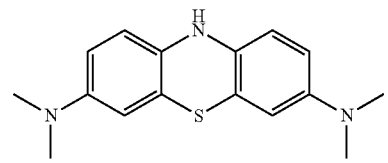

To a 250 cm³ round bottom flask placed under an atmosphere of argon was added methylthioninium chloride (Medex™) (MTC.$3H_2O$, MW 373.90, 10 g, 26.7 mmol) and ethanol (100 cm³). Hydrazine hydrate ($NH_2NH_2.H_2O$, MW 32.05, 3.0 cm³, 68.0 mmol) was added in portions. The mixture was heated to 40° C. and stirred for 30 minutes. The resulting green suspension was cooled to 5° C. using an ice-water bath and filtered by canular under argon, washed once with ethanol (20 cm³), and dried under vacuum at room temperature to give the title compound as a light green/grey solid. The product was used without further purification in Synthesis 8.

Synthesis 8

3,7-Dimethylamino-10-acetyl-phenothiazine

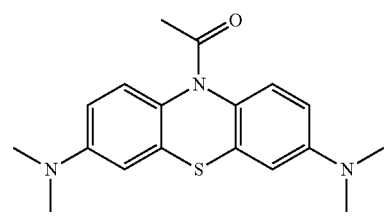

The 3,7-dimethylamino-10H-phenothiazine obtained in Synthesis 7 was placed in a 250 cm³ round bottom flask and acetic anhydride (($H_3CCO)_2O$, 40 cm³) and pyridine (10 cm³) were added, and the resulting solution was heated at 100° C. for 18 hours with stirring. The reaction mixture was cooled to room temperature and then poured carefully into ice-water while stirring to give a light brown solid, which was filtered using a standard Buchner funnel apparatus with a water aspirator, washed once with water (100 cm³), and dried in an oven at 60° C. for 3 hours to yield the title compound, which was recrystallised from ethanol by dissolving it in hot ethanol (100 cm³), adding activated charcoal (1 g), filtering to remove the charcoal, cooling the solution to 5° C. using an ice-water bath so that a precipitate formed (colourless crystals), and filtering using a standard Buchner filter with a water aspirator in order to collect the crystals. The crystals where then dried in an oven at 60° C. for 3 hours (MW 327.45, 4.25 g, 13.0 mmol, yield 49%).

$\delta_H$ (250 MHz; CDCl₃) 2.16 (3H, s, CH₃), 2.92 (12H, s, NCH₃), 6.60-6.62 (2H, d, ArH), 6.70-6.73 (2H, d, ArH), 7.08-7.47 (2H, brd s, ArH).

Synthesis 9

Methylthioninium Chloride (MTC)

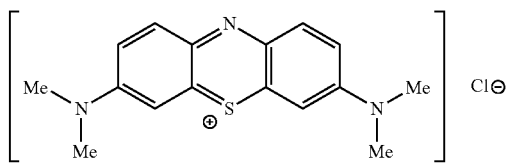

3,7-Dimethylamino-10-acetyl-phenothiazine obtained in Synthesis 8 (MW 327.45, 1 g, 3.05 mmol) was placed in a 50 cm³ round bottom flask, and water (10 cm³) and hydrochloric acid (10 M, 3 cm³) were added, and the resulting solution was heated at 80° C. for 1 hour with stirring to give a green solution. The reaction mixture was cooled to 5° C. using an ice-water bath, and divided into six fractions (6×2 cm³). Individual fractions (2 cm³) were used in each of the following synthesis methods.

Method A: To one fraction (2 cm³), aqueous iron chloride hexahydrate (FeCl₃.6H₂O, MW 270.30, 0.17 g, 0.63 mmol, 2 cm³) was added, giving an immediate deep blue colour. After 10 minutes, the mixture was filtered and the precipitate was washed with water (~2 cm³) and air-dried to give the title compound as a green powder (MW 319.86, 0.16 g, 0.51 mmol, 100%).

Method B: To one fraction (2 cm³), Amberlite resin I.R. 120 (0.1 g) was added, giving an immediate blue colour. The mixture was heated to 60° C. for 30 minutes, and then hot-filtered to remove the resin. Hydrochloric acid (10 M, 4 drops) was added, and the mixture was allowed to stand for 4 days. Then the mixture was filtered and the precipitate was washed with water (~2 cm³) and air-dried to give the title compound as green crystals (MW 319.86, 0.14 g, 0.44 mmol, 86%).

The purity levels for the products are summarized in the following Table. Note that the Medex™ starting material had a corresponding purity of 93.86%.

TABLE 5

| Method | Reagent | Purity (wt %) |
|---|---|---|
| A | Iron chloride hexahydrate | 99.09 |
| B | Amberlite Resin I.R. 120 | 98.94 |

Synthesis 10

3,7-Dimethylamino-10-acetyl-phenothiazine

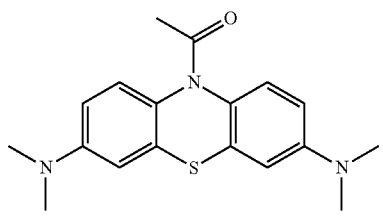

To a 250 cm³ round bottom flask placed under an atmosphere of argon was added methylthioninium chloride (Medex™) (MTC.3H₂O, MW 373.90, 10 g, 26.7 mmol) and acetonitrile (50 cm³). Hydrazine hydrate (NH₂NH₂.H₂O, MW 50.06, 2.85 cm³, 58.7 mmol) was added in portions. The mixture was heated to 65° C. and stirred for 20 minutes. The resulting brown suspension was cooled to 5° C. using an ice-water bath. Acetic anhydride ((H₃CCO)₂O, MW 102.09, 25 cm³, 267 mmol) and N,N-diisopropylethylamine (MW 129.24, 9.3 cm³, 53.6 mmol) were added, and the resulting solution was heated at 100° C. for 2 hours with stirring. The reaction mixture was cooled to 5° C. and had water (50 cm³) added while stirring to give a light green solid, which was filtered using a standard Buchner funnel apparatus with a water aspirator, washed with water (4×6 cm³), and dried in an oven at 60° C. for 3 hours to yield the title compound, which was purified from hot ethanol (27 cm³), cooling the solution to 5° C. using an ice-water bath so that a precipitate formed, and filtering using a standard Buchner filter with a water aspirator in order to collect the crystals. The crystals where then dried in an oven at 60° C. for 3 hours (MW 327.45, 5.68 g, 17.4 mmol, yield 65%).

$\delta_H$ (250 MHz; CDCl₃) 2.16 (3H, s, CH₃), 2.92 (12H, s, NCH₃), 6.60-6.62 (2H, d, ArH), 6.70-6.73 (2H, d, ArH), 7.08-7.47 (2H, brd s, ArH).

Synthesis 11

Methylthioninium Chloride (MTC)

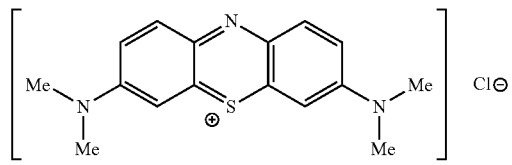

3,7-Dimethylamino-10-acetyl-phenothiazine obtained in Synthesis 10 (MW 327.45, 5 g, 15.27 mmol) was placed in a 50 cm³ round bottom flask, and water (10 cm³) and hydrochloric acid (10 M, 5 cm³) were added, and the resulting solution was heated at 80° C. for 1 hour with stirring to give a green solution. The reaction mixture was cooled to 5° C. using an ice-water bath, and divided into four even fractions (4×4 cm³). One fraction (4 cm³) was used in each of the following synthesis methods.

Method A: To one fraction (4 cm³, 3.82 mmol), aqueous iron chloride hexahydrate (FeCl₃.6H₂O, MW 270.30, 2.06 g, 7.63 mmol, 15 cm³) solution was added, giving an immediate deep blue colour. After 30 minutes, the mixture was filtered and the precipitate was washed with filtrate (~5 cm³) and air-dried to give the title compound as a green powder (MW 319.86, 1.22 g, 3.82 mmol, 100%).

Method B: To one fraction (4 cm³, 3.82 mmol), isoamyl nitrite (MW 117.5, 0.45 g, 3.82 mmol, in 8 cm³ of ethanol) was added, giving an immediate deep blue colour. After 30 minutes, the mixture was filtered and the precipitate was washed with filtrate (~5 cm³) and air-dried to give the title compound as a green powder (MW 319.86, 0.64 g, 1.98 mmol, 52%).

Method C: To one fraction (4 cm³, 3.82 mmol), tert-butylamyl nitrite (MW 103.1, 0.39 g, 3.82 mmol, in 8 cm³ of ethanol) was added, giving an immediate deep blue colour. After 30 minutes, the mixture was filtered and the precipitate was washed with filtrate (~5 cm³) and air-dried to give the title compound as a green powder (MW 319.86, 0.67 g, 2.10 mmol, 55%).

Method D: To one fraction (4 cm³, 3.82 mmol), Amberlite resin I.R. 120 (1.25 g) was added, giving an immediate blue colour. The mixture was heated to 60° C. for 30 minutes, and then hot-filtered to remove the resin. Hydrochloric acid (10 M, 1 cm³) was added, and the mixture was allowed to stand for 4 days. Then the mixture was filtered and the precipitate was washed with filtrate (~5 cm³) and air-dried to give the title compound as green crystals (MW 319.86, 1.05 g, 3.29 mmol, 86%).

The purity levels for the products are summarized in the following Table. Note that the Medex™ starting material had a corresponding purity of 93.86%.

TABLE 5

| Method | Reagent | Purity (wt %) |
|---|---|---|
| A | Iron chloride hexahydrate | 99.09 |
| B | Isoamyl nitrite | 98.89 |
| C | tert-Butyl nitrite | 99.27 |
| D | Amberlite Resin I.R. 120 | 98.94 |

Synthesis 12

3,7-Dimethylamino-10-acetyl-phenothiazine

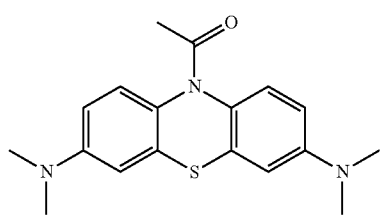

To a 1000 cm³ round bottom flask placed under an atmosphere of argon was added methylthioninium chloride (Medex™) (MTC.3H₂O, MW 373.90, 50 g, 134 mmol) and acetonitrile (250 cm³). Methylhydrazine (MeNHNH₂, MW 46.07, 14.26 cm³, 268 mmol) was added in portions. The mixture was heated to 35° C. and stirred for 20 minutes. The resulting brown suspension was cooled to 5° C. using an ice-water bath. Acetic anhydride ((H₃CCO)₂O, MW 102.09, 101 cm³, 1.0 mol) and N,N-diisopropylethylamine (MW 129.24, 46.7 cm³, 268 mmol) were added, and the resulting solution was heated at 100° C. for 2 hours with stirring. The reaction mixture was cooled to 5° C. and then had water (250 cm³) added while stirring to give a light green solid, which was filtered using a standard Buchner funnel apparatus with a water aspirator, washed with water (4×30 cm³), and dried in an oven at 60° C. for 3 hours to yield the title compound, which was purified from hot ethanol (120 cm³) by cooling the solution to 5° C. using an ice-water bath so that a precipitate formed and filtering using a standard Buchner filter with a water aspirator in order to collect the crystals. The crystals were then dried in an oven at 60° C. for 3 hours (MW 327.45, 30.71 g, 93.8 mmol, yield 70%).

δ$_H$ (250 MHz; CDCl₃) 2.16 (3H, s, CH₃), 2.92 (12H, s, NCH₃), 6.60-6.62 (2H, d, ArH), 6.70-6.73 (2H, d, ArH), 7.08-7.47 (2H, brd s, ArH).

Synthesis 13

Methylthioninium Chloride (MTC)

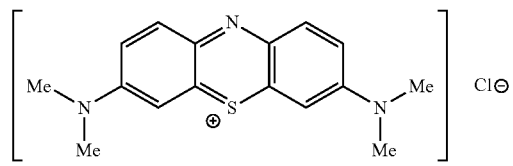

3,7-Dimethylamino-10-acetyl-phenothiazine obtained in Synthesis 9 (MW 327.45, 24.5 g, 75 mmol) was placed in a 500 cm³ round bottom flask, and water (50 cm³) and hydrochloric acid (10 M, 25 cm³) were added, and the resulting solution was heated at 80° C. for 1 hour with stirring to give a green solution. The reaction mixture was cooled to 5° C. using an ice-water bath. A cooled (5° C.) aqueous iron chloride hexahydrate solution (FeCl₃.6H₂O, MW 270.30, 40.6 g, 150 mmol, 300 cm³) was added, giving an immediate deep blue colour. After 30 minutes stirring, the suspension was filtered and the precipitate was washed with filtrate (~25 cm³) and air-dried for 30 minutes to give the crude title compound as a purple solid. This material was dissolved in a mixture of water (480 cm³) and hydrochloric acid (10 M, 7.9 cm³) by heating to reflux before cooling to 25° C. The fine green needles were filtered, washed with filtrate (50 cm³), and oven dried at 60° C. for 18 hours to give the title compound containing 9% water (MW 319.86, 23.46 g, 74 mmol, 98%). (The reported yield has been adjusted to represent anhydrous MTC). The mass of purified product that was obtained was 25.78 g, which contained 9% water. The characterisation data was the same as reported above for Synthesis 6.

Synthesis 14

3,7-Dinitrophenothiazine

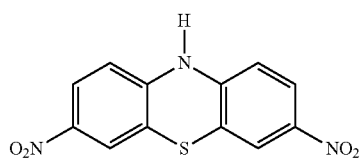 [SMILES: O=[N+]([O-])c1ccc2c(c1)Sc1cc([N+](=O)[O-])ccc1N2]

Phenothiazine (MW 199.28, 20.00 g, 100 mmol), dichloromethane (100 cm³) and acetic acid (40 cm³) had sodium nitrite (MW 69.00, 20.7 g, 300 mmol) added and the mixture was stirred for 10 minutes at room temperature. Additional acetic acid (40 cm$^3$), dichloromethane (100 cm$^3$), and sodium nitrite (MW 69.00, 20.7 g, 300 mmol) were then added. A further 120 cm$^3$ of acetic acid was added to try to break up the thick reaction mixture. The mixture was stirred for 2 hours. The suspension was filtered and washed with 100 cm$^3$ of each of ethanol, water, and finally ethanol to give a purple/brown solid. The residue was stirred in hot DMF (100 cm$^3$) and allowed to cool before filtering to give the title dinitro product, which was washed with ethanol (150 cm$^3$) and dried (MW 289.27, 24.88 g, 86.0 mmol, 86%) to give a brown solid.

$\nu_{max}$ (KBr)/cm$^{-1}$ 3331 (NH), 3294 (NH), 3229 (NH), 3101 (CH), 3067 (CH), 1602 (NO$_2$), 1558 (NO$_2$); $\delta_H$ (250 MHz; DMSO) 6.73-6.76 (2H, d, J 9, ArH), 7.78 (2H, s, ArH), 7.89-7.85 (2H, d, J 9, ArH).

Synthesis 15

3,7-Dinitro-10-acetyl-phenothiazine

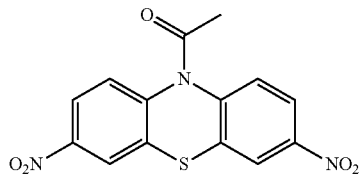 [SMILES: CC(=O)N1c2ccc([N+](=O)[O-])cc2Sc2cc([N+](=O)[O-])ccc21]

A solution of 3,7-dinitrophenothiazine (MW 289.27, 24.0 g, 82.96 mmol), acetic anhydride (MW 102.09, 151 g, 1.48 mol) and pyridine (100 cm$^3$) was stirred at reflux for 18 hours. The warm solution was then cooled to room temperature and poured carefully over ice water. The precipitate formed was filtered to give the title compound (MW 331.26, 21.14 g, 63.81 mmol, 77%) as a sand coloured solid which was recrystallised from acetone to give light yellow needles.

$\nu_{max}$ (KBr)/cm$^{-1}$ 3091 (CH), 3063 (CH), 1680 (C=O), 1575 (NO$_2$), 1510 (NO$_2$); $\delta_H$ (250 MHz; CDCl$_3$) 2.28 (3H, s, CH$_3$), 7.65-7.69 (2H, d, J 9, ArH), 8.22-8.26 (2H, dd, J 2.75, 8.75, ArH), 8.33-8.32 (2H, d, J 2.5, ArH); $\delta_C$ (62.9 MHz; CDCl$_3$) 168.2 (C=O), 146.3 (ArC), 143.3 (ArC), 133.6 (ArC), 127.8 (ArC), 123.4 (ArC), 122.9 (ArC), 23.1 (CH$_3$); m/z (ES) 331.0 (80%, [M]$^+$).

Synthesis 16

3,7-diamino-10-acetyl-phenothiazine dihydrochloride

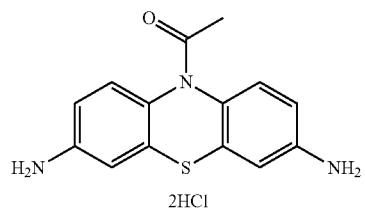 [SMILES: CC(=O)N1c2ccc(N)cc2Sc2cc(N)ccc21]

A mixture of 3,7-dinitro-10-acetyl-phenothiazine (MW 331.26, 2 g, 6.04 mmol), palladium 10% on dry carbon (0.2 g) and tetrahydrofuran (20 cm$^3$) was heated to 60° C. under an atmosphere of hydrogen and stirred at this temperature for 18 hours. The mixture was cooled to room temperature, poured over celite filter aid, and washed with tetrahydrofuran (10 cm$^3$). The THF filtrate was acidified with hydrochloric acid (10 M, 4 cm$^3$) to precipitate the product as a solid. The suspension was filtered to give the title compound as a light green solid, which was dried at 60° C. for 3 hours (MW 344.26, 4.3 mmol, 1.49 g, 72%).

$\delta_H$ (250 MHz; DMSO-d6) 2.12 (3H, s, CH$_3$), 7.30 (2H, d, J 8.25, ArH), 7.45 (2H, s, ArH), 7.66 (2H, d, J 8.25, ArH); $\delta_C$ (62.9 MHz; CDCl$_3$) 168.6 (C=O), 136.1 (ArC), 133.6 (ArC), 132.8 (ArC), 128.1 (ArC), 120.8 (ArC), 22.6 (CH$_3$).

Synthesis 17

3,7-Dimethylamino-10-acetyl-phenothiazine

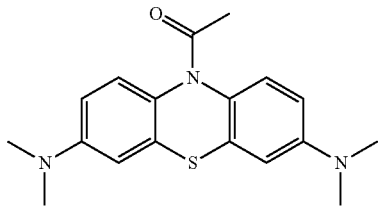

3,7-diamino-10-acetyl-phenothiazine dihydro chloride (MW 344.26, 2.59 g, 7.55 mmol) was dissolved in water (7.5 cm$^3$) in a conical flask (25 cm$^3$) and to this solution was added sodium hydroxide solution (10%) to obtain a precipitate. The solid was filtered to give the free amine 3,7-diamino-10-acetyl-phenothiazine (MW 271.34, 2.05 g, 7.55 mmol) which was dissolved in acetic acid (20 cm$^3$) and p-formaldehyde (MW 30.03, 4.53 g, 151 mmol) and sodium cyanoborohydride (MW 62.84, 4.74 g, 75.5 mmol) was added. The mixture was stirred at 50° C. for 2 hours, after which water (50 cm$^3$) was added and the solid filtered to give crude product. This material was crystallized from ethanol (17 cm$^3$) to give the title compound (MW 327.45, 0.75 g, 30%) as a colourless solid.

Mp 137° C.; $\nu_{max}$ (KBr)/cm$^{-1}$ 2910 (CH), 2876 (CH), 2856 (CH), 2799 (CH), 1659 (C=O), 1596 (NO$_2$), 1502 (NO$_2$); $\delta_H$ (250 MHz; CDCl$_3$) 2.16 (3H, s, CH$_3$), 2.93 (12H, s, NCH$_3$), 6.59-6.62 (2H, d, J 8.5, ArH), 6.69-6.71 (2H, d, J 2.75, ArH), 7.08-7.47 (2H, brd s, ArH); $\delta_C$ (62.9 MHz; CDCl$_3$) 170.3 (C=O), 148.9 (ArC), 127.2 (ArC), 127.1 (ArC), 127.0 (ArC), 110.9 (ArC), 110.7 (ArC), 40.7 (NCH$_3$), 22.9 (CH$_3$); m/z (ES) 284.2 (100%, [M−OAc]$^+$), 328.1 (15%, [M+H]$^+$), 350.1 (41%, [M+Na]$^+$).

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Badische Anilin-und Soda-Fabrik, 1877, "Verfahren Zur Darstellung Blauer Farbstoffe Aus Dimethyl-Anilin Und Anderen Tertiaren Aromatischen Monaminen," German Patent No. 1886, published 15 Dec. 1877.

Bernthsen, August, 1885a, "Studien in der Methylenblaugruppe," Justus Liebig's Annalen der Chemie, Band 230, pp. 73-136.

Bernthsen, August, 1885b, "Studien in der Methylenblaugruppe," Justus Liebig's Annalen der Chemie, Band 230, pp. 137-211.

Bernthsen, August, 1889, "Studien in der Methylenblaugruppe," Justus Liebig's Annalen der Chemie, Band 251, pp. 1-96.

Cohn, G., 1899, "Verfahren zur Darstellung von Acetylleukomethylenblau und -athyleneblau," Chem. Zentralblatt, Vol. 70, II, p. 503.

Cohn, G., 1900, "Zur Kenntniss des Leukomethyleneblaus," Chemische Berichte, Vol. 33, pp. 1567-1568.

Colour Index, Vol. 4 (3rd Edition, 1971), p. 4470, Entry Number 52015.

Drew, H. D. K., Head, F. S. H., 1933, "Derivatives of Methylene-blue," Journal of the Chemical Society, pp. 248-253.

Fierz-David and Blangley, 1949, "F. Oxazine and Thiazine Dyes," in: Fundamental Processes of Dye Chemistry, published by Interscience (London, UK), pp. 308-314.

Gilman, H., et al., "Some Derivatives of Phenothiazine," Journal of the American Chemical Society, 1944, Vol. 66, pp. 888-893.

Guttmann P, Ehrlich P. Über die Wirkung des Methylenblau bei Malaria. Berl Klin Wochenschr 1891; 28: 953-956.

Leventis, N., et al., "Synthesis of Substituted Phenothiazine Analogues to Methylene Blue by Electrophilic and Nucleophilic Aromatic Substitutions in Tandem, A Mechanistic Perspective," Tetrahedron, 1997, Vol. 53, No. 29, pp. 10083-10092.

Leventis, N., et al., 1997, "Synthesis of Substituted Phenothiazines Analogous to Methylene Blue by Electrophilic and Nucleophilic Aromatic Substitutions in Tandem. A Mechanistic Perspective," Tetrahedron, Vol. 53, No. 29, pp. 10083-10092.

Lillie, R. D., et al., 1979, "Zinc Chloride Methylene Blue, I. Biological Stain History, Physical Characteristics and Approximation of Azure B Content of Commercial Samples," Stain Technology, Vol. 54, No. 1, pp. 33-39.

Lohr, W., Grubhoffer, N., Sohmer, I., Wittekind, D., 1975, "The azure dyes: their purification and physiochemical properties. Purification of Azure B," Stain Technology, Vol. 50 (3), pp. 149-156.

Marshall, P. N., Lewis, S. M., 1975a, "The purification of Methylene Blue and Azure B by solvent extraction and crystallisation," Stain Technology, Vol. 50(6), pp. 375-381.

Marshall, P. N., Lewis, S. M., 1975b, "Metal contaminants in commercial dyes," Stain Technology, Vol. 50 (3), pp. 143-147.

Masuya, Hirotomo, 1992, "Phenothiazine Derivatives, Their Production and Use," European Patent Publication No 0 510 668 A2, published 28 Oct. 1992.

Rengelshausen, J., Burhenne, J., Frohlich, M., Tayrouz, Y., Singh, S. K., Riedel, K.-D., Muller, O., Hoppe-Tichy, T., Haefeli, W. E., Mikus, G. & Walter-Sack, I. (2004) Pharmacokinetic interaction of chloroquine and methylene blue combination against malaria. European Journal of Clinical Pharmacology 60, 709-715.

Schirmer, H., Coulibaly, B., Stich, A., Scheiwein, M., Merkle, H., Eubel, J., Becker, K., Becher, H., Müller, O., Zich, T., Schiek, W. & Kouyaté, B. (2003) Methylene blue as an antimalarial agent. Redox Report 8, 272-275.

Schweiger, L. F., et al., 2005, "Methods of [11C]-Radiolabelling Phenothiazine and Phenothiazone-like Compounds," published international (PCT) patent application publication number WO 2005/030676 published 7 Apr. 2005.

Storey, J. M. D., et al., 2006, "Methods of Chemical Synthesis and Purification of Diaminophenothiazinium Compounds Including Methylthioninium Chloride (MTC)," published international (PCT) patent application publication number WO 2006/032879 published 30 Mar. 2006.

Tomilin, O. B., et al., "Synthesis and Properties of Phenothiazine Derivatives," Chemistry of Heterocyclic Compounds, 1996, Vol. 32, No. 9, pp. 1105-1108.

Wischik, C. M., et al., 1996, "Inhibition of Tau-Tau-Association," published international (PCT) patent application publication number WO 96/30766 published 3 Oct. 1996.

Wischik, C. M., et al., 2002a, "Materials and Methods Relating to Protein Aggregation in Neurodegenerative Disease," published international (PCT) patent application publication number WO 02/055720 published 18 Jul. 2002.

Wischik, C. M., et al., 2002b, "Neurofibrillary Labels," published international (PCT) patent application publication number WO 02/075318 published 26 Sep. 2002.

The invention claimed is:

1. A method for the synthesis of a high purity diaminophenothiazinium compound (DAPTC) of the following formula:

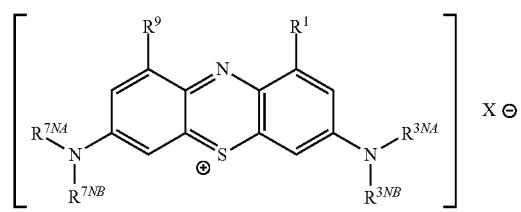

wherein:

each of $R^1$ and $R^9$ is independently selected from: —H; $C_{1-4}$alkyl; $C_{2-4}$alkenyl; and halogenated $C_{1-4}$alkyl;

each of $R^{3NA}$ and $R^{3NB}$ is independently selected from: $C_{1-4}$alkyl; $C_{2-4}$alkenyl; and halogenated $C_{1-4}$alkyl;

each of $R^{7NA}$ and $R^{7NB}$ is independently selected from: $C_{1-4}$alkyl; $C_{2-4}$alkenyl; and halogenated $C_{1-4}$alkyl; and X is one or more anionic counter ions to achieve electrical neutrality;

wherein the diaminophenothiazinium compound (DAPTC) is characterised by:

a purity of greater than 98%;

less than 1% Azure B as impurity;

less than 0.15% Azure A as impurity;

less than 0.15% Azure C as impurity; and less than 0.05% Methylene Violet Bernthsen (MVB) as impurity which method comprises at least the following steps, in order:

purifying (PUR) a corresponding acylated reagent compound (ARC) of the following formula wherein $R^{10}$ is independently saturated aliphatic $C_{1-5}$alky, phenyl, p-methoxyphenyl, or p-nitrophenyl:

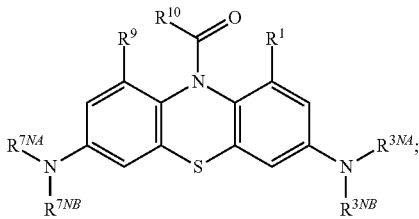

deacylating (DAC) said acylated reagent compound (ARC) to give a corresponding deacylated compound of the following formula

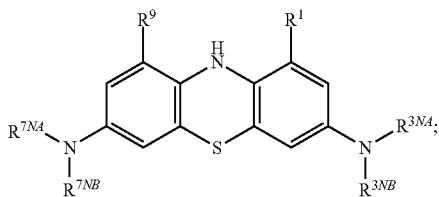

optionally purifying (PUR$^{DAC-OX}$) said deacylated compound;

oxidizing (OX) said deacylated compound at a temperature below 10° C. to give said diaminophenothiazinium compound (DAPTC); and purifying (PUR$^{OX}$) said diaminophenothiazinium compound (DAPTC) by recrystallization, wherein said recrystallization includes a step of adjusting the pH of the mixture to be about 0.5 to 2.5.

2. A method according to claim 1, wherein each of $R^1$ and $R^9$ is independently —H, -Me, -Et, or —CF$_3$.

3. A method according to claim 1, wherein each of $R^1$ and $R^9$ is independently —H, -Me, or -Et.

4. A method according to claim 1, wherein each of $R^1$ and $R^9$ is independently —H.

5. A method according to claim 1, wherein the groups —N($R^{3NA}$)($R^{3NB}$) and —N($R^{7NA}$)($R^{7NB}$) are independently selected from: —NMe$_2$, —NEt$_2$, —N(nPr)$_2$, —N(Bu)$_2$, —NMeEt, —NMe(nPr), and —N(CH$_2$CH=CH$_2$)$_2$.

6. A method according to claim 1, wherein the groups —N($R^{3NA}$)($R^{3NB}$) and —N($R^{7NA}$)($R^{7NB}$) are independently selected from: —NMe$_2$ and —Net$_2$).

7. A method according to claim 1, wherein each of the groups —N($R_{3NA}$)($R_{3NB}$) and —N($R_{7NA}$)($R^{7NB}$) is independently —NMe$_2$.

8. A method according to claim 1, wherein X$^-$ is independently Cl$^-$, Br$^-$, or I$^-$, or NO$_3^-$.

9. A method according to claim 1, wherein X$^-$ is independently Cl$^-$.

10. A method according to claim 1, wherein one or more or all of the carbon atoms of one or more or all of the groups $R^{3NA}$, $R^{3NB}$, $R^{7NA}$ and $R^{7NB}$ is $^{13}$C.

11. A method according to claim 1, wherein the diaminophenothiazinium compound (DAPTC) has a purity of greater than 99%.

12. A method according to claim 1, wherein the diaminophenothiazinium compound has a purity of greater than 99.5%.

13. A method according to claim 1, wherein the diaminophenothiazinium compound has a purity of greater than 99.6%.

14. A method according to claim 1, wherein the diaminophenothiazinium compound has a purity of greater than 99.7%.

15. A method according to claim 1, wherein the diaminophenothiazinium compound has less than 0.5% Azure B as impurity.

16. A method according to claim 1, wherein the diaminophenothiazinium compound has less than 0.10% Azure A as impurity.

17. A method according to claim 1, wherein the diaminophenothiazinium compound has less than 0.05% Azure A as impurity.

18. A method according to claim 1, wherein the diaminophenothiazinium compound has less than 0.10% Azure C as impurity.

19. A method according to claim 1, wherein the diaminophenothiazinium compound has less than 0.05% Azure C as impurity.

20. A method according to claim 1, wherein the diaminophenothiazinium compound has less than 0.02% MVB as impurity.

21. A method according to claim 1, wherein the diaminophenothiazinium compound has:
less than 100 μg/g Aluminium (Al);
less than 1 μg/g Cadmium (Cd);
less than 100 μg/g Chromium (Cr);
less than 300 μg/g Copper (Cu);
less than 10 μg/g Tin (Sn);
less than 200 μg/g Iron (Fe);
less than 10 μg/g Manganese (Mn);
less than 1 μg/g Mercury (Hg);
less than 10 μg/g Molybdenum (Mo);
less than 10 μg/g Nickel (Ni);
less than 10 μg/g Lead (Pb); and
less than 100 μg/g Zinc (Zn).

22. A method according to claim 1, wherein the diaminophenothiazinium compound has:
less than 50 μg/g Aluminium (Al);
less than 0.5 μg/g Cadmium (Cd);
less than 50 μg/g Chromium (Cr);
less than 150 μg/g Copper (Cu);
less than 5 μg/g Tin (Sn);
less than 100 μg/g Iron (Fe);
less than 5 μg/g Manganese (Mn);
less than 0.5 μg/g Mercury (Hg);
less than 5 μg/g Molybdenum (Mo);
less than 5 μg/g Nickel (Ni);
less than 5 μg/g Lead (Pb); and
less than 50 μg/g Zinc (Zn).

23. A method according to claim 1 wherein the diaminothiazinium compound is methylthioninium chloride (MTC).

24. A method according to claim 1, wherein $R^{10}$ is independently saturated aliphatic $C_{1-5}$alkyl.

25. A method according to claim 1, wherein $R^{10}$ is independently -Me, -Et, -Pr, -nBu, or -nPe.

26. A method according to claim 1, wherein $R^{10}$ is independently -Me.

27. A method according to claim 1, which method comprises at least the following steps, in order:
acylating (AC1) a corresponding non-acylated precursor of a corresponding acylated reagent compound (NAPARC) to give a corresponding acylated reagent compound (ARC) of the following formula, wherein $R^{10}$ is independently saturated aliphatic $C_{1-5}$alkyl, phenyl, p-methoxyphenyl, or p-nitrophenyl:

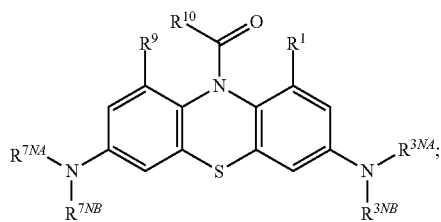

purifying (PUR) said acylated reagent compound (ARC);

deacylating (DAC) said acylated reagent compound (ARC) to give a corresponding deacylated compound of the following formula:

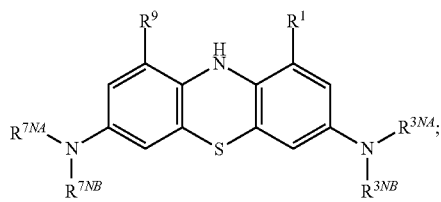

optionally purifying (PUR$^{DAC-OX}$) said deacylated compound;

oxidizing (OX) said deacylated compound at a temperature of below 10° C. to give said diaminophenothiazinium compound of the following formula:

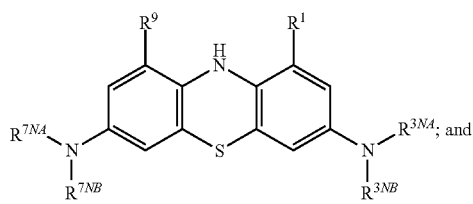

purifying (PUR$^{OX}$) said diaminophenothiazinium compound (DAPTC) by recrystallization.

28. A method according to claim 1, which method comprises at least the following steps, in order:

reducing (RED) under an inert atmosphere a corresponding oxidized precursor of a corresponding non-acylated precursor of a corresponding acylated reagent compound (OPNAPARC) of the following formula, wherein $X^a$ is as defined for X, and may be the same as or different than X:

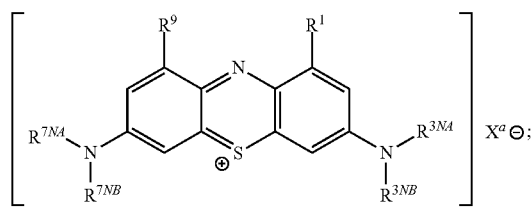

to give said corresponding non-acylated precursor of said acylated reagent compound (NAPARC) which is a compound of the following formula:

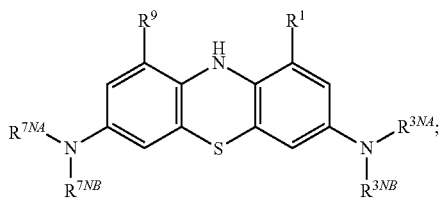

optionally purifying (PUR$^{RED-AC1}$) said non-acylated precursor (NAPARC);

acylating (AC1) said non-acylated precursor (NAPARC) to give said acylated reagent compound (ARC) of the following formula, wherein $R^{10}$ is independently saturated aliphatic $C_{1-5}$alkyl, phenyl, p-methoxyphenyl, or p-nitrophenyl:

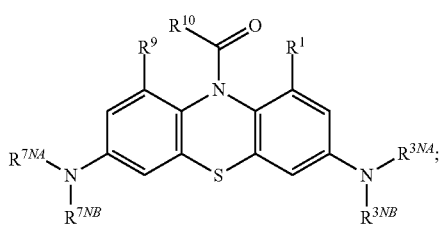

purifying (PUR) said acylated reagent compound (ARC);

deacylating (DAC) said acylated reagent compound (ARC) to give a corresponding deacylated compound of the following formula:

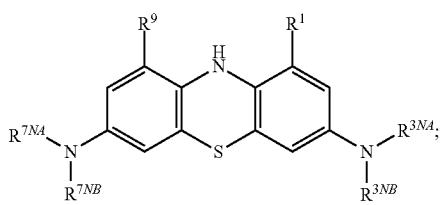

optionally purifying (PUR$^{DAC-OX}$) said deacylated compound;

oxidizing (OX) said deacylated compound at a temperature of below 10° C. to give said diaminophenothiazinium compound; and purifying (PUR$^{OX}$) said diaminophenothiazinium compound (DAPTC) by recrystallization.

29. A method according to claim 1, which method comprises at least the following steps, in order:

converting (CON) a corresponding acylated upstream precursor of a corresponding acylated reagent compound (AUPARC) of the following formula, wherein $R^{10}$ independently saturated aliphatic $C_{1-5}$alkyl, phenyl, p-methoxyphenyl, or p-nitrophenyl:

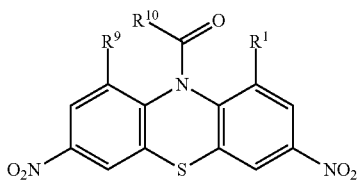

to said acylated reagent compound (ARC), which is a compound of the following formula:

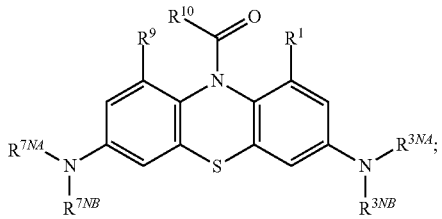

purifying (PUR) said acylated reagent compound (ARC);
deacylating (DAC) said acylated reagent compound (ARC) to give a corresponding deacylated compound of the following formula:

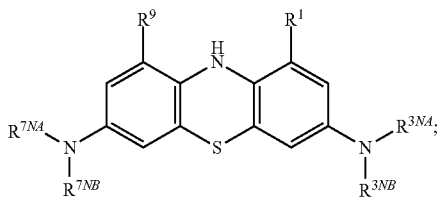

optionally purifying ($PUR^{DAC-OX}$) said deacylated compound;
oxidizing (OX) said deacylated compound to give said diaminophenothiazinium compound; and
optionally purifying ($PUR^{OX}$) said diaminophenothiazinium compound (DAPTC).

30. A method according to claim 1, which method comprises at least the following steps, in order:
acylating (AC2) a corresponding non-acylated upstream precursor of a corresponding acylated reagent compound (NAUPARC) of the formula:

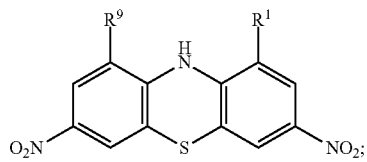

to give said acylated upstream precursor of said acylated reagent compound (AUPARC) which is a compound of the following formula. wherein $R^{10}$ is independently saturated all hatic $C_{1-5}$alkyl, phenyl, p-methoxyphenyl, or p-nitrophenyl:

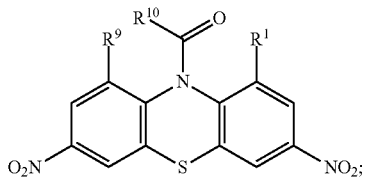

optionally purifying ($PUR^{AC2-CON}$) said acylated upstream precursor (AUPARC);
converting (CON) said acylated upstream precursor (AUPARC) to said acylated reagent compound (ARC) of the following formula:

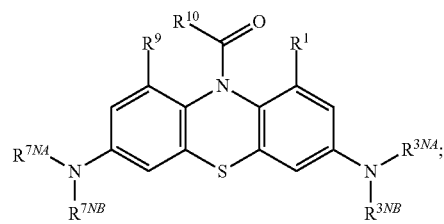

purifying (PUR) said acylated reagent compound (ARC);
deacylating (DAC) said acylated reagent compound (ARC) to give a corresponding deacylated compound of the following formula:

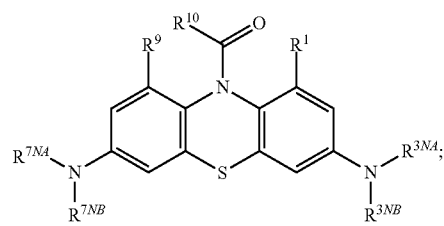

optionally purifying ($PUR^{DAC-OX}$) said deacylated compound;
oxidizing (OX) said deacylated compound to give said diaminophenothiazinium compound; and
optionally purifying ($PUR^{OX}$) said diaminophenothiazinium compound (DAPTC).

* * * * *